United States Patent
Chari et al.

(10) Patent No.: US 7,473,796 B2
(45) Date of Patent: Jan. 6, 2009

(54) CYTOTOXIC AGENTS COMPRISING NEW MAYTANSINOIDS

(75) Inventors: Ravi V. J. Chari, Newton, MA (US); Wayne C. Widdison, Somerville, MA (US)

(73) Assignee: Immunogen Inc., Waltham, MA (US)

( * ) Notice: Subject to any disclaimer, the term of this patent is extended or adjusted under 35 U.S.C. 154(b) by 0 days.

(21) Appl. No.: 11/778,464

(22) Filed: Jul. 16, 2007

(65) Prior Publication Data

US 2007/0270585 A1 Nov. 22, 2007

Related U.S. Application Data

(62) Division of application No. 10/849,136, filed on May 20, 2004, now Pat. No. 7,276,497.

(60) Provisional application No. 60/493,457, filed on Aug. 8, 2003, provisional application No. 60/471,739, filed on May 20, 2003.

(51) Int. Cl.
*C07C 229/00* (2006.01)
*C07C 315/00* (2006.01)
*C07D 267/22* (2006.01)

(52) U.S. Cl. ............... 560/41; 562/556; 540/456

(58) Field of Classification Search ............ None
See application file for complete search history.

(56) References Cited

U.S. PATENT DOCUMENTS

| | | | | |
|---|---|---|---|---|
| 6,333,410 | B1 * | 12/2001 | Chari et al. | 540/456 |
| 6,441,163 | B1 * | 8/2002 | Chari et al. | 540/458 |
| 6,570,024 | B2 * | 5/2003 | Eldridge et al. | 548/542 |
| 6,573,074 | B2 | 6/2003 | Fulston et al. | |
| 6,716,821 | B2 * | 4/2004 | Zhao et al. | 514/34 |
| 6,884,874 | B2 * | 4/2005 | Eldridge et al. | 530/391.9 |
| 7,276,497 | B2 * | 10/2007 | Chari et al. | 514/229.5 |
| 7,301,019 | B2 * | 11/2007 | Widdison et al. | 540/456 |
| 2003/0157669 | A1 | 8/2003 | Fulston | |
| 2004/0241174 | A1 | 12/2004 | Amphlett et al. | |
| 2005/0176780 | A1 * | 8/2005 | Polla | 514/352 |

* cited by examiner

*Primary Examiner*—Daniel M Sullivan
*Assistant Examiner*—Louisa Lao
(74) *Attorney, Agent, or Firm*—Sughrue Mion, PLLC

(57) ABSTRACT

New thiol and disulfide-containing maytansinoids bearing a mono or di-alkyl substitution on the α-carbon atom bearing the sulfur atom are disclosed. Also disclosed are methods for the synthesis of these new maytansinoids and methods for the linkage of these new maytansinoids to cell-binding agents. The maytansinoid-cell-binding agent conjugates are useful as therapeutic agents, which are delivered specifically to target cells and are cytotoxic. These conjugates display vastly improved therapeutic efficacy in animal tumor models compared to the previously described agents.

13 Claims, 20 Drawing Sheets

(May = maytansinoid)

Y = (CR$_7$R$_8$)$_l$(CR$_5$R$_6$)$_m$(CR$_3$R$_4$)$_n$CR$_1$R$_2$SZ

DM3 (4a): R$_1$, R$_5$, R$_6$, R$_7$, R$_8$ = H; R$_2$ = CH$_3$
l = 1, m = 1, n = 0
Z = H

DM3-SMe (4c): R$_1$, R$_5$, R$_6$, R$_7$, R$_8$ = H; R$_2$ = CH$_3$
l = 1, m = 1, n = 0
Z = SCH$_3$

DM4 (4b): R$_5$, R$_6$, R$_7$, R$_8$ = H; R$_1$, R$_2$ = CH$_3$
l = 1, m = 1, n = 0
Z = H

DM4-SMe (4e): R$_5$, R$_6$, R$_7$, R$_8$ = H; R$_1$, R$_2$ = CH$_3$
l = 1, m = 1, n = 0
Z = SCH$_3$

FIG. 4a   *In vitro* Cytotoxicity towards A-375 cells
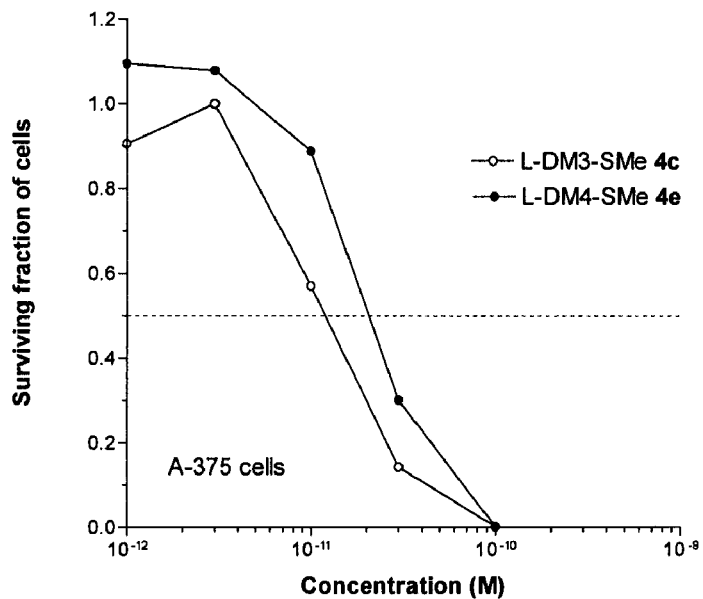
FIG. 4b   *In vitro* Cytotoxicity towards SK-Br-3 cells
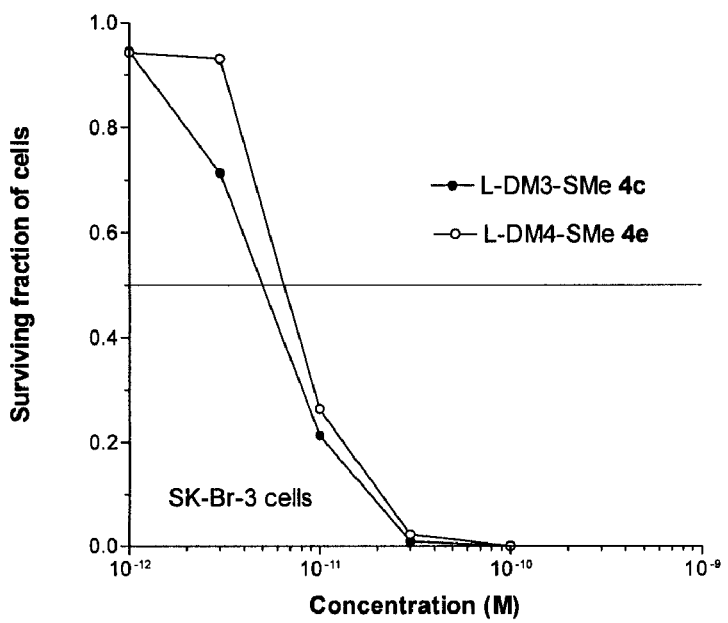

FIG. 4c  *In vitro* Cytotoxicity towards KB cells
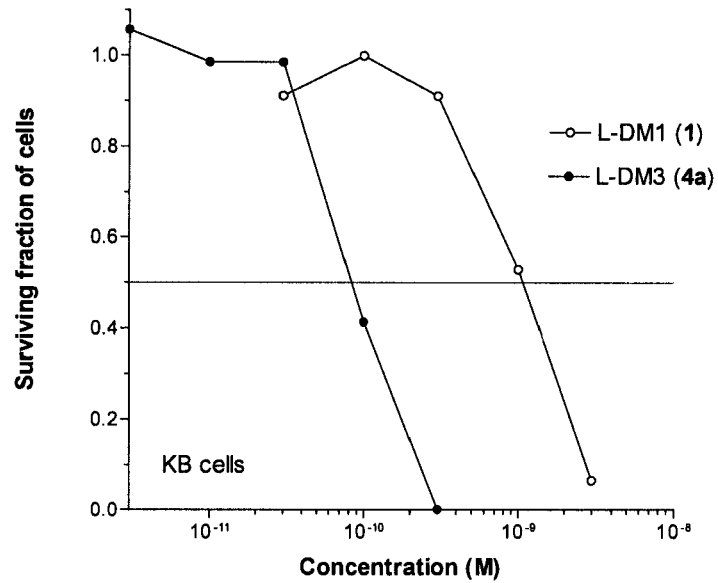
FIG. 4d  *In vitro* Cytotoxicity towards SK-Br-3 cells
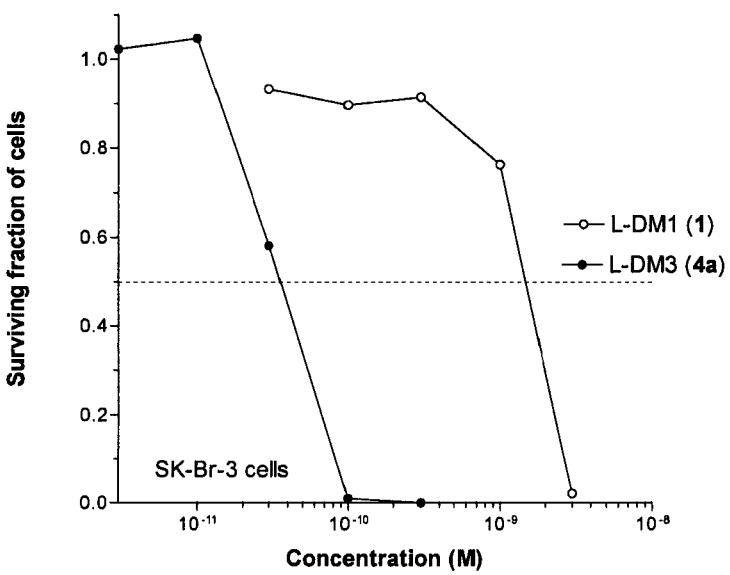

Antibody-DM3 Conjugate: R = H
Antibody-DM4 Conjugate: R = Me

Antibody-DM3 Conjugate: R = H
Antibody-DM4 Conjugate: R = Me

FIG. 6  *In Vitro* Cytotoxicity and Specificity of huC242-DM3 and huC242-DM4 Conjugates
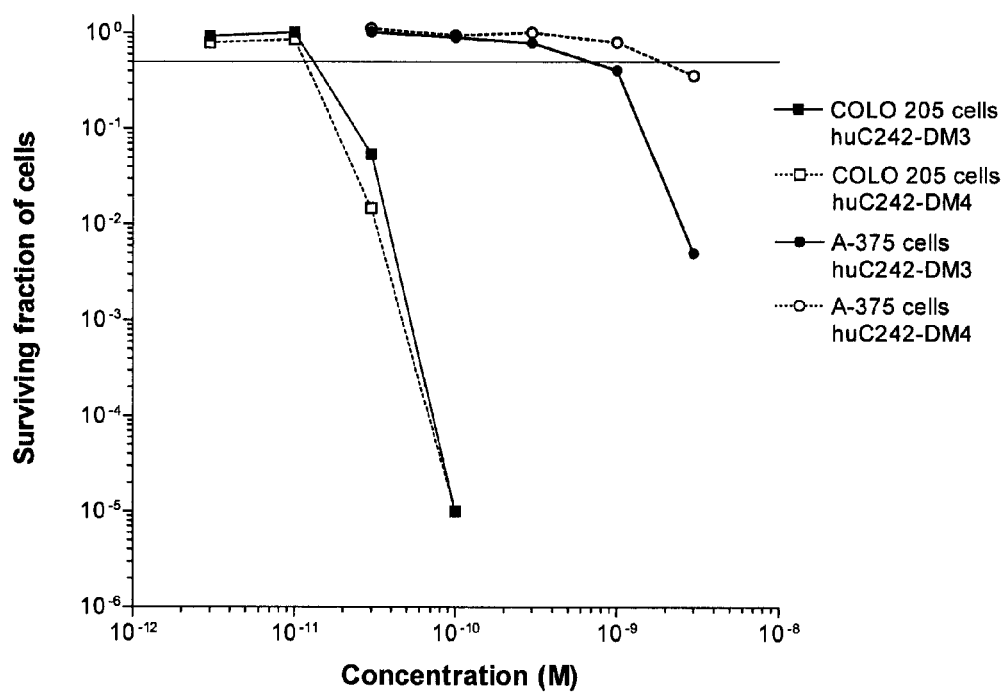

FIG. 7    *In vivo* Efficacy of huC242-Maytansinoid Conjugates (HT-29 Xenografts)
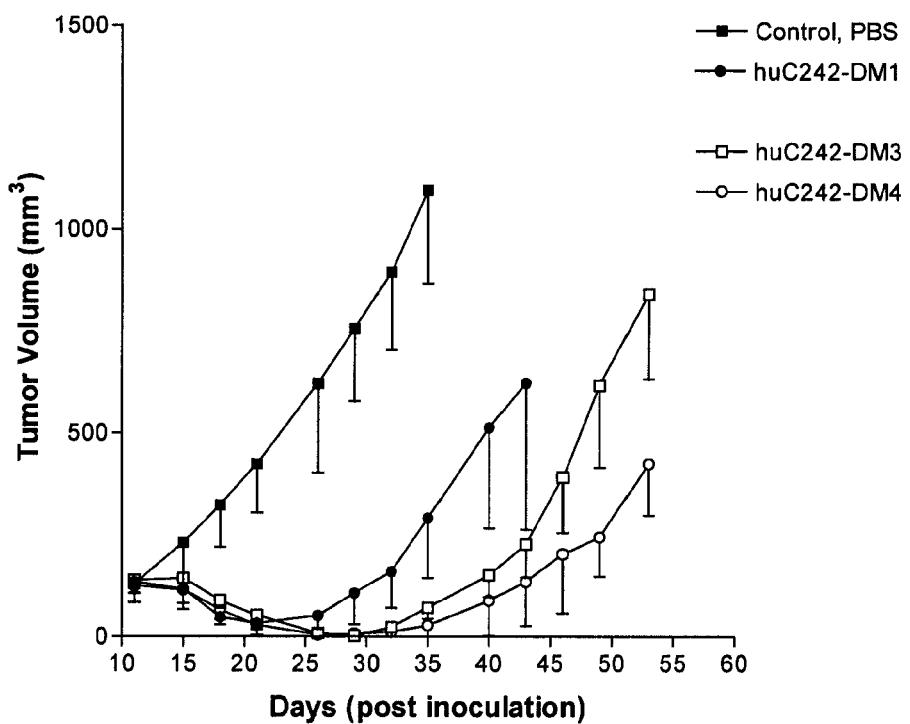

FIG. 8  *In vivo* Efficacy of huC242-Maytansinoid Conjugates (COLO-205 Xenografts)
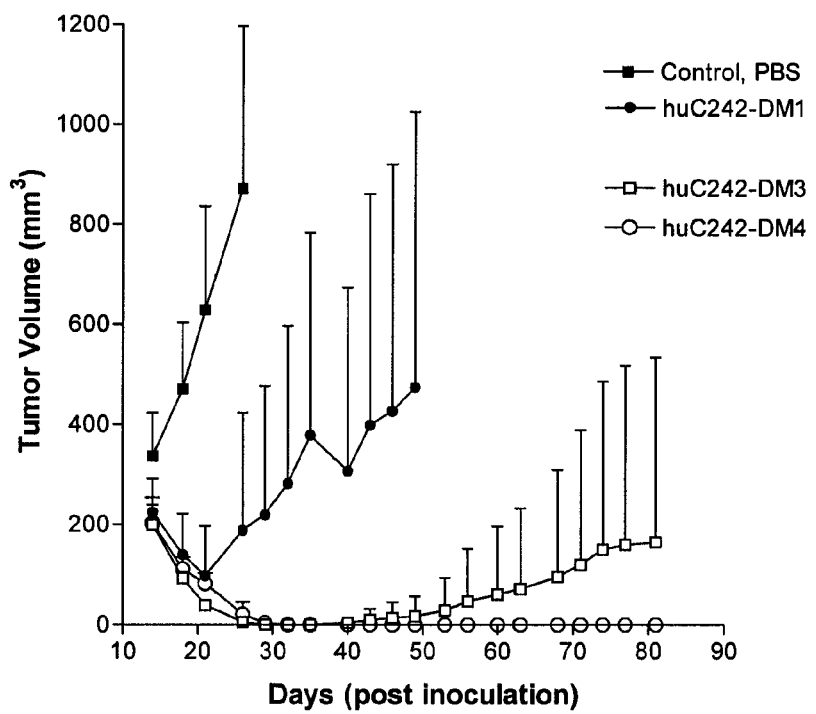

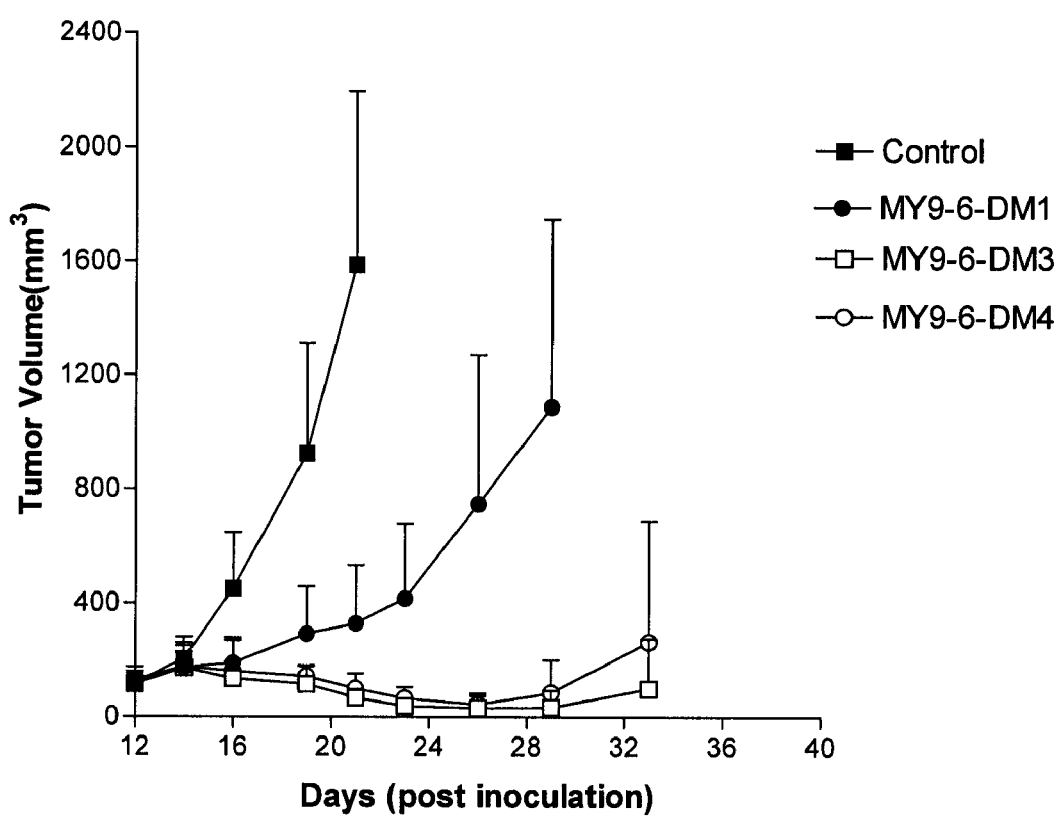
FIG. 9 Efficacy of MY-9-6-Maytansinoid Conjugates (HL60 xenografts)

FIG. 10  In vitro cytotoxicity analysis: HuMy9-6-DM4 activity toward antigen-positive HL-60 cells and antigen-negative Namalwa cells.
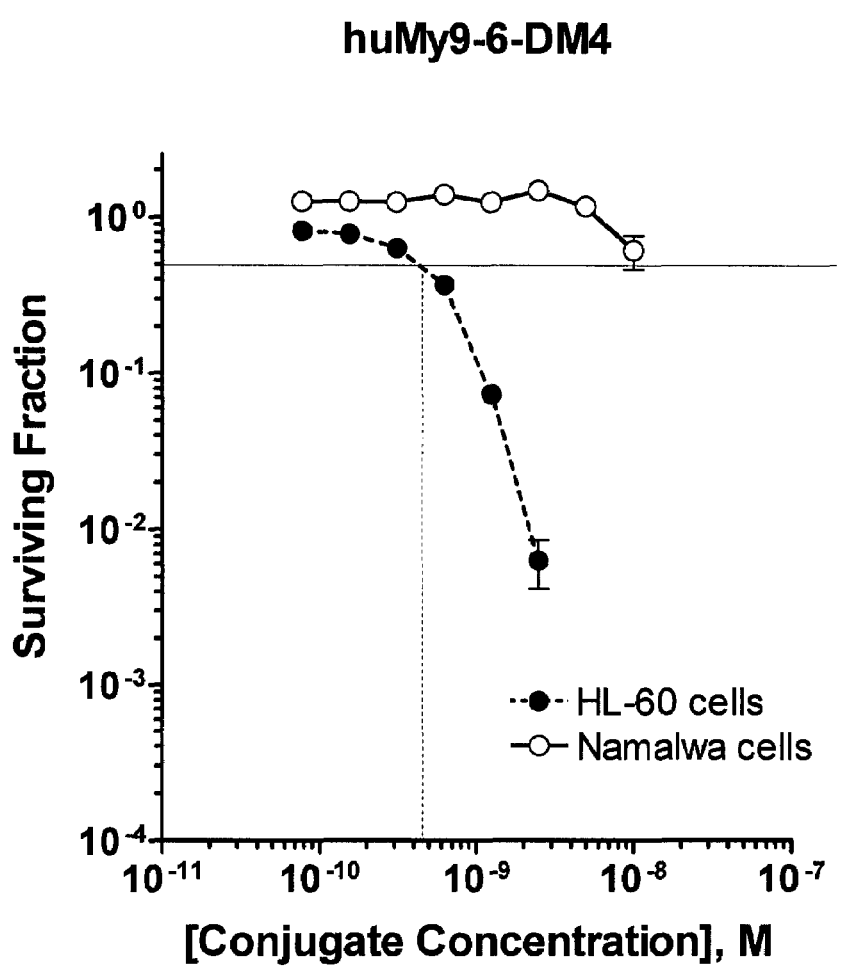

FIG. 11 Comparison of in vivo efficacy of huMy9-6-DM4 and huMy9-6-DM1 conjugates against HL-60 human tumor xenografts in SCID mice.
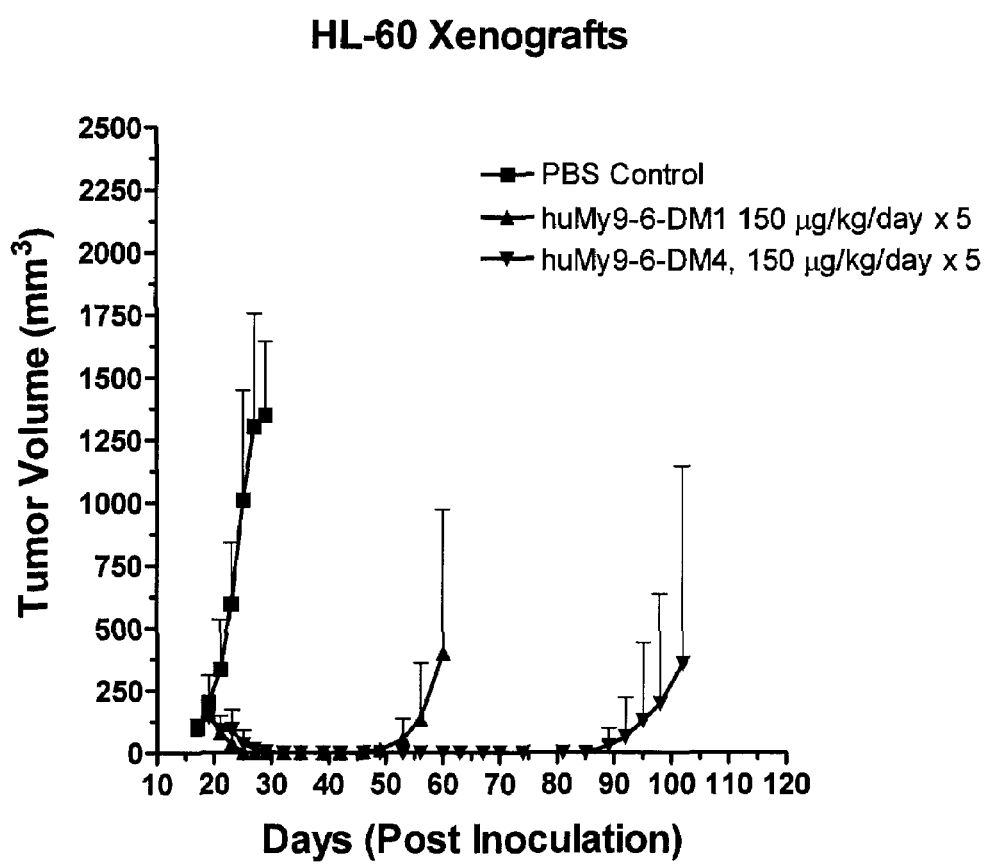

FIG. 12. *In vitro* cytotoxicity analysis of huB4-DM4
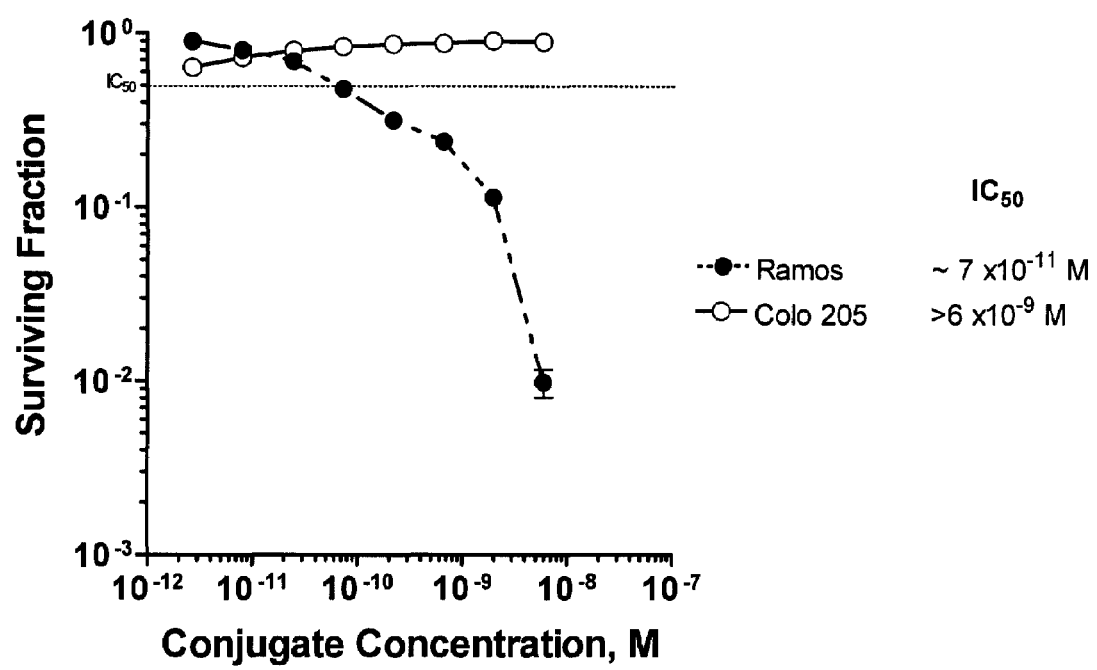

Figure 13a. *In vivo* efficacy of huB4-DM4 conjugate against Ramos xenografts in SCID mice
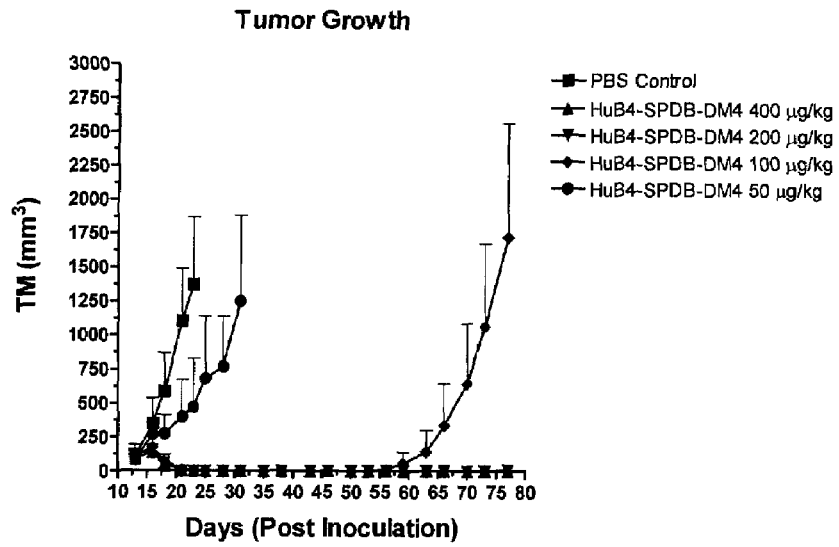
Figure 13b. *In vivo* efficacy of huB4-DM4 conjugate against Ramos xenografts in SCID mice: body weight changes in treated animals
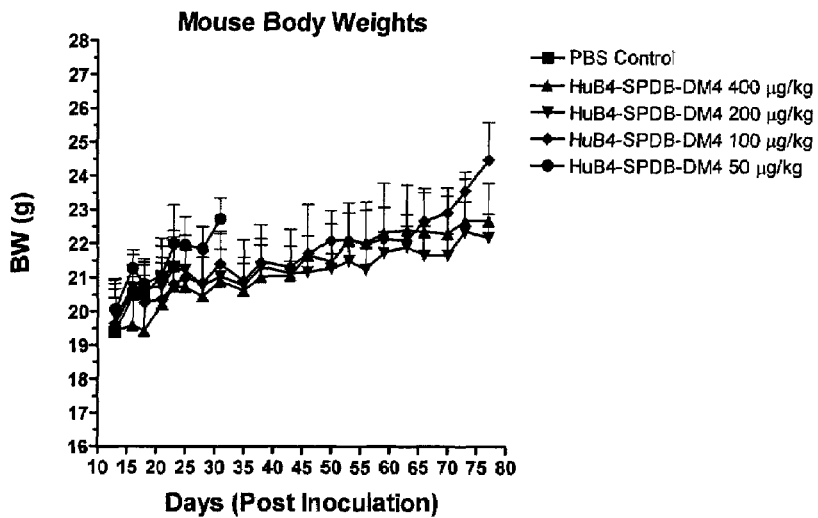

CYTOTOXIC AGENTS COMPRISING NEW MAYTANSINOIDS

This application is a divisional of pending U.S. application Ser. No. 10/849,136 (Confirmation No. 8145) filed May 20, 2004 (allowed), which claims benefit of Provisional Application No. 60/471,739, filed May 20, 2003, and Provisional Application No. 60/493,457, filed Aug. 8, 2003, the disclosure of each of which is incorporated herein by reference in its entirety.

FIELD OF THE INVENTION

The present invention relates to a method for preparing improved cytotoxic conjugates comprising maytansinoids and cell-binding agents. These conjugates have therapeutic use as they are delivered to a specific cell population in a targeted fashion. The present invention also relates to a method for preparing maytansinoids having a thiol moiety, which may be used in the preparation of cytotoxic conjugates. The present invention further relates to novel maytansinoids, and to novel intermediates in the synthesis of the novel maytansinoids.

BACKGROUND OF THE INVENTION

Many reports have appeared on the attempted specific targeting of tumor cells with monoclonal antibody-drug conjugates (Sela et al. in *Immunoconjugates* 189-216 (C. Vogel, ed. 1987); Ghose et al, in *Targeted Drugs* 1-22 (E. Goldberg, ed. 1983); Diener et al, in *Antibody Mediated Delivery Systems* 1-23 (J. Rodwell, ed. 1988); Pietersz et al, in *Antibody Mediated Delivery Systems* 25-53 (J. Rodwell, ed. 1988); Bumol et al, in *Antibody Mediated Delivery Systems* 55-79 (J. Rodwell, ed. 1988). Cytotoxic drugs such as methotrexate, daunorubicin, doxorubicin, vincristine, vinblastine, melphalan, mitomycin C, and chlorambucil have been conjugated to a variety of murine monoclonal antibodies. In some cases, the drug molecules were linked to the antibody molecules through an intermediary carrier molecule such as serum albumin (Garnett et al. *Cancer Res.* 46:2407-2412 (1986); Ohkawa et al. *Cancer Immumol. Immunother.* 23:81-86 (1986); Endo et al. *Cancer Res.* 47:1076-1080 (1980)), dextran (Hurwitz et al. *Appl. Biochem.* 2:25-35 (1980); Manabi et al. *Biochem. Pharmacol.* 34:289-291 (1985); Dillman et al. *Cancer Res.* 46:4886-4891 (1986); Shoval et al. *Proc. Natl. Acad. Sci.* 85:8276-8280 (1988)), or polyglutamic acid (Tsukada et al. *J. Natl. Canc. Inst.* 73:721-729 (1984); Kato et al. *J. Med. Chem.* 27:1602-1607 (1984); Tsukada et al. *Br. J. Cancer* 52:111-116 (1985)).

A wide array of linker technologies has been employed for the preparation of such immunoconjugates, and both cleavable and non-cleavable linkers have been investigated. In most cases, the full cytotoxic potential of the drugs could only be observed, however, if the drug molecules could be released from the conjugates in unmodified form at the target site.

One of the cleavable linkers that has been employed for the preparation of antibody-drug conjugates is an acid-labile linker based on cis-aconitic acid that takes advantage of the acidic environment of different intracellular compartments such as the endosomes encountered during receptor mediated endocytosis and the lysosomes. Shen and Ryser introduced this method for the preparation of conjugates of daunorubicin with macromolecular carriers (*Biochem. Biophys. Res. Commun.* 102:1048-1054 (1981)). Yang and Reisfeld used the same technique to conjugate daunorubicin to an anti-melanoma antibody (*J. Natl. Canc. Inst.* 80:1154-1159 (1988)). Recently, Dillman et al. also used an acid-labile linker in a similar fashion to prepare conjugates of daunorubicin with an anti-T cell antibody (*Cancer Res.* 48:6097-6102 (1988)).

An alternative approach, explored by Trouet et al. involved linking daunorubicin to an antibody via a peptide spacer arm (*Proc. Natl. Acad. Sci.* 79:626-629 (1982)). This was done under the premise that free drug could be released from such a conjugate by the action of lysosomal peptidases.

In vitro cytotoxicity tests, however, have revealed that antibody-drug conjugates rarely achieved the same cytotoxic potency as the free unconjugated drugs. This suggested that mechanisms by which drug molecules are released from the antibodies are very inefficient. In the area of immunotoxins, conjugates formed via disulfide bridges between monoclonal antibodies and catalytically active protein toxins were shown to be more cytotoxic than conjugates containing other linkers. See, Lambert et al. *J. Biol. Chem.* 260:12035-12041 (1985); Lambert et al. in *Immunotoxins* 175-209 (A. Frankel, ed. 1988); Ghetie et al. *Cancer Res.* 48:2610-2617 (1988). This was attributed to the high intracellular concentration of glutathione contributing to the efficient cleavage of the disulfide bond between an antibody molecule and a toxin. Despite this, there are only a few reported examples of the use of disulfide bridges for the preparation of conjugates between drugs and macromolecules. Shen et al. described the conversion of methotrexate into a mercaptoethylamide derivative followed by conjugation with poly-D-lysine via a disulfide bond (*J. Biol. Chem.* 260:10905-10908 (1985)). In addition, a few reports described the preparation of conjugates of the trisulfide-containing toxic drug calicheamicin with antibodies (Hinman et al, 53 *Cancer Res.* 3336-3342 (1993), Hamann et al., *Bioconjugate Chem.*, 13, 40-46 (2002), Hamann et al., *Bioconjugate Chem.*, 13, 47-58 (2002)).

One reason for the lack of disulfide linked antibody-drug conjugates is the unavailability of cytotoxic drugs that bear a sulfur atom containing moiety that can be readily used to link the drug to an antibody via a disulfide bridge. Furthermore, chemical modification of existing drugs is difficult without diminishing their cytotoxic potential.

Maytansinoids are highly cytotoxic drugs. Maytansine was first isolated by Kupchan et al. from the east African shrub *Maytenus serrata* and shown to be 100 to 1000 fold more cytotoxic than conventional cancer chemotherapeutic agents like methotrexate, daunorubicin, and vincristine (U.S. Pat. No. 3,896,111). Subsequently, it was discovered that some microbes also produce maytansinoids, such as maytansinol and C-3 esters of maytansinol (U.S. Pat. No. 4,151,042). Synthetic C-3 esters of maytansinol and analogues of maytansinol have also been reported (Kupchan et al. *J. Med. Chem.* 21:31-37 (1978); Higashide et al. *Nature* 270:721-722 (1977); Kawai et al. *Chem. Pharm. Bull.* 32:3441-3451 (1984)). Examples of analogues of maytansinol from which C-3 esters have been prepared include maytansinol with modifications on the aromatic ring (e.g. dechloro) or at the C-9, C-14 (e.g. hydroxylated methyl group), C-15, C-18, C-20 and C-4,5.

The naturally occurring and synthetic C-3 esters of maytansinol can be classified into two groups:

(a) C-3 esters with simple carboxylic acids (U.S. Pat. Nos. 4,248,870; 4,265,814; 4,308,268; 4,308,269; 4,309,428; 4,317,821; 4,322,348; and 4,331,598), and (b) C-3 esters with derivatives of N-methyl-L-alanine (U.S. Pat. Nos. 4,137,230; 4,260,608; 5,208,020; and *Chem. Pharm. Bull.* 12:3441 (1984)).

Esters of group (b) were found to be much more cytotoxic than esters of group (a).

Maytansine is a mitotic inhibitor. Treatment of L11210 cells in vivo with maytansine has been reported to result in 67% of the cells accumulating in mitosis. Untreated control cells were reported to demonstrate a mitotic index ranging from between 3.2 to 5.8% (Sieber et al. 43 *Comparative Leukemia Research* 1975, Bibl. Haemat. 495-500 (1976)). Experiments with sea urchin eggs and clam eggs have suggested that maytansine inhibits mitosis by interfering with the formation of microtubules through the inhibition of the polymerization of the microtubule protein, tubulin (Remillard et al. *Science* 189:1002-1005 (1975)).

In vitro, P388, L1210, and LY5178 murine leukemic cell suspensions have been found to be inhibited by maytansine at doses of $10^{-3}$ to $10^{-1}$ μg/μl with the P388 line being the most sensitive. Maytansine has also been shown to be an active inhibitor of in vitro growth of human nasopharyngeal carcinoma cells, and the human acute lymphoblastic leukemia line CEM was reported inhibited by concentrations as low as $10^{-7}$ μg/ml (Wolpert-DeFillippes et al. *Biochem. Pharmacol.* 24:1735-1738 (1975)).

In vivo, maytansine has also been shown to be active. Tumor growth in the P388 lymphocytic leukemia system was shown to be inhibited over a 50- to 100-fold dosage range, which suggested a high therapeutic index; also significant inhibitory activity could be demonstrated with the L1210 mouse leukemia system, the human Lewis lung carcinoma system and the human B-16 melanocarcinoma system (Kupchan, *Ped. Proc.* 33:2288-2295 (1974)). Maytansinoids used in conjugates with cell-binding agents are described in U.S. Pat. Nos. 5,208,020 and 5,416,064 and in Chari et al., *Cancer Res.*, 52: 127-131 (1992) and Liu et al., *Proc. Natl. Acad. Sci.*, 93: 8618-8623 (1996). In these conjugates, the cell-binding agent is linked via disulfide bonds to the maytansinoid DM1 [$N^{2'}$-deacetyl-$N^{2'}$-(3-mercapto-1-oxopropyl)-maytansine, 1, CAS Number: 139504-50-0, FIG. 1]

In the above patents, the maytansinoid drugs bearing acylated N-methyl-L-alanine side chains are of the formula 2a,b:

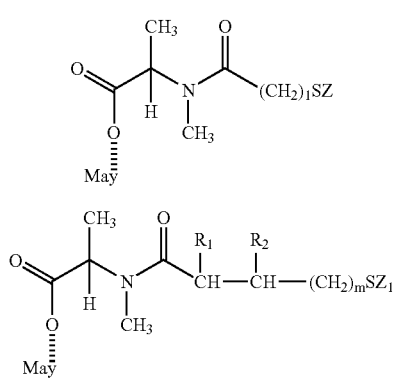

In formula 2a, l represents an integer from 1 to 10. Thus maytansinoids of the formula 2a have the sulfur atom connected to an unsubstituted methylene group (—CH$_2$—S—). It is said that a sulfhydryl group in such a maytansinoid compound or a disulfide group in a disulfide-linked cell-binding agent-maytansinoid conjugate with such a maytansinoid is "non-hindered," since there are no bulky substituents on the α-carbon next to the sulfhydryl or disulfide group, which cause steric hindrance. In formula 2b, m represents 0, 1, 2 or 3. Therefore, maytansinoids of the formula 2b also have the sulfur atom connected to an unsubstituted methylene group, except in the case where m=0, and R$_2$=CH$_3$ or CH$_2$CH$_3$. If m=0, then the maytansinoid bears one substituent on the carbon bearing the thiol functionality or a disulfide functionality after conjugation to a cell-binding agent via a disulfide bond. However, because in this case the sulfur atom is in the β position relative to a carbonyl group, these maytansinoids and conjugates of such maytansinoids with cell-binding agents via a disulfide bond were found to be unstable due to their propensity to undergo β-elimination.

SUMMARY OF THE INVENTION

The present invention is based on the unexpected finding that the linkage of maytansinoids, bearing a sterically hindered thiol group (possessing one or two substituents on the α-carbon bearing the thiol functionality), to cell-binding agents gives conjugates that have vastly improved anti-tumor activity in vivo as compared to conjugates prepared with the previously described maytansinoids that did not possess a substituent on the α-carbon atom bearing the disulfide bond. Another unexpected finding was that improved biological activity is obtained when the steric hindrance is optimally on the maytansinoid side of the disulfide bond in the conjugates. In addition, the acyl group of the acylated amino acid side chain of the maytansinoid bearing the sulfhydryl group has to possess a linear chain length of at least three carbon atoms between the carbonyl group of the amide and the sulfur atom.

These findings show that disulfide-linked cell-binding agent-maytansinoid conjugates can be constructed such that substitutions on the two α-carbon atoms bearing the disulfide bond can lead to varying degrees of steric hindrance on either side of the disulfide bond.

Accordingly, the present invention describes the synthesis of new, sterically hindered thiol and disulfide-containing maytansinoids, which bear one or two alkyl substituents on the α-carbon atom bearing the sulfur atom. In addition, the acyl group of the acylated amino acid side chain possesses a linear chain length of at least three carbon atoms between the carbonyl group of the amide and the sulfur atom.

The preparation and biological evaluation of cell-binding agent conjugates of these new maytansinoids is also described.

In one embodiment of the invention, new thiol and disulfide-containing maytansinoids bearing a mono or di-alkyl substitution on the carbon atom bearing the sulfur atom are described.

In a second embodiment, the present invention discloses methods for the synthesis of these new maytansinoids.

In a third embodiment, methods for the linkage of these new maytansinoids to cell-binding agents are described. These conjugates are useful as therapeutic agents, which are delivered specifically to target cells and are cytotoxic. These conjugates display vastly improved therapeutic efficacy in animal tumor models compared to the previously described agents.

More specifically, the present invention provides:

A maytansinoid having, at C-3, C-14 hydroxymethyl, C-15 hydroxy, or C-20 desmethyl, an acylated amino acid side chain with an acyl group bearing a hindered sulfhydryl group, wherein the carbon atom of the acyl group bearing the thiol functionality has one or two substituents, said substituents being CH$_3$, C$_2$H$_5$, linear or branched alkyl or alkenyl having from 1 to 10 carbon atoms, cyclic alkyl or alkenyl having from 3 to 10 carbon atoms, phenyl, substituted phenyl, or heterocyclic aromatic or heterocyclic radical, and in addition one of the substituents can be H, and wherein the acyl group has a linear chain length of at least three carbon atoms between the carbonyl functionality and the sulfur atom;

A compound represented by formula 4':

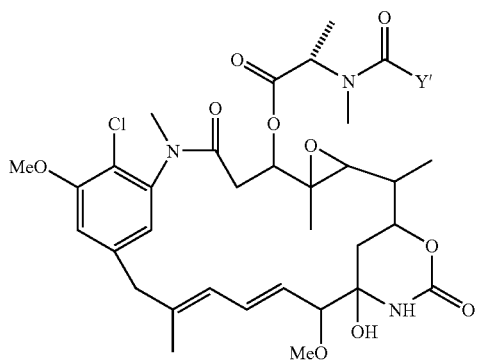

4' wherein:

Y' represents $(CR_7R_8)_l(CR_9=CR_{10})_p(C\equiv C)_qA_o (CR_5R_6)_m D_u(CR_{11}=CR_{12})_r(C\equiv C)_sB_t(CR_3R_4)_nCR_1R_2SZ$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

A, B, D are cycloalkyl or cycloalkenyl having 3-10 carbon atoms, simple or substituted aryl or heterocyclic aromatic or heterocyclic radical;

$R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m, n, o, p, q, r, s, t and u are each independently 0 or an integer of from 1 to 5, provided that at least two of l, m, n, o, p, q, r, s, t and u are not zero at any one time.

Z is H, SR or —COR, wherein R is linear alkyl or alkenyl having 1 to 10 carbon atoms, branched or cyclic alkyl or alkenyl having from 3 to 10 carbon atoms, or simple or substituted aryl or heterocyclic aromatic or heterocyclic radical.

A compound represented by formula 4', wherein $R_1$ is H, $R_2$ is methyl and Z is H.

A compound represented by formula 4', wherein $R_1$ and $R_2$ are methyl and Z is H.

A compound represented by formula 4', wherein $R_1$ is H, $R_2$ is methyl, and Z is —$SCH_3$.

A compound represented by formula 4', wherein $R_1$ and $R_2$ are methyl, and Z is —$SCH_3$.

A compound represented by formula (I-L), (I-D), or (I-D, L):

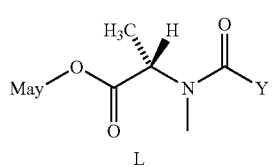

(I)

L

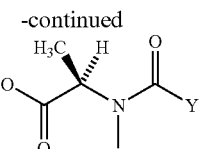

D

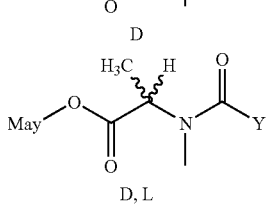

D, L wherein:

Y represents $(CR_7R_8)_l(CR_5R_6)_m(CR_3R_4)_nCR_1R_2SZ$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocyclic radical;

l, m and n are each independently an integer of from 1 to 5, and in addition n can be 0;

Z is H, SR or —COR wherein R is linear or branched alkyl or alkenyl having from 1 to 10 carbon atoms, cyclic alkyl or alkenyl having from 3 to 10 carbon atoms, or simple or substituted aryl or heterocyclic aromatic or heterocyclic radical; and May represents a maytansinoid which bears the side chain at C-3, C-14 hydroxymethyl, C-15 hydroxy or C-20 desmethyl;

The above-described compound, wherein $R_1$ is H, $R_2$ is methyl, $R_5$, $R_6$, $R_7$, and $R_8$ are each H, l and m are each 1, n is 0, and Z is H;

The above-described compound, wherein $R_1$ and $R_2$ are methyl, $R_5$, $R_6$, $R_7$, $R_8$ are each H, l and m are 1, n is 0, and Z is H;

The above-described compound, wherein $R_1$ is H, $R_2$ is methyl, $R_5$, $R_6$, $R_7$, and $R_8$ are each H, l and m are each 1, n is 0, and Z is —$SCH_3$;

The above-described compound, wherein $R_1$ and $R_2$ are methyl, $R_5$, $R_6$, $R_7$, $R_8$ are each H, l and m are 1, n is 0, and Z is —$SCH_3$;

A compound represented by formula 4:

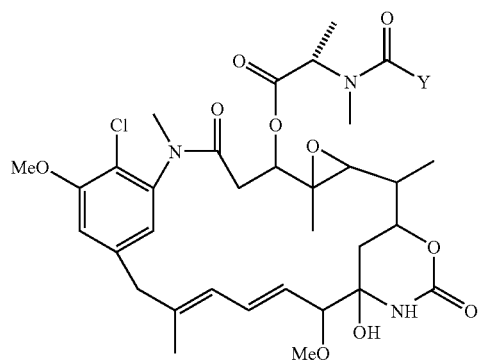

4 wherein:

Y represents $(CR_7R_8)_l(CR_5R_6)_m(CR_3R_4)_nCR_1R_2SZ$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocyclic radical;

l, m and n are each independently an integer of from 1 to 5, and in addition n can be 0; and Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical;

The compound of formula 4, wherein R1 is H, R2 is methyl, R5, R6, R7, and R8 are each H; l and m are each 1; n is 0; and Z is H;

The compound of formula 4, wherein $R_1$ and $R_2$ are methyl; $R_5$, $R_6$, $R_7$, $R_8$ are each H, l and m are 1; n is 0; and Z is H;

The compound of formula 4, wherein $R_1$ is H, $R_2$ is methyl, $R_5$, $R_6$, $R_7$, and $R_8$ are each H, l and m are each 1, n is 0, and Z is —$SCH_3$;

The compound of formula 4, wherein $R_1$ and $R_2$ are methyl, $R_5$, $R_6$, $R_7$, $R_8$ are each H, l and m are 1, n is 0, and Z is —$SCH_3$;

A maytansinoid-cell-binding agent conjugate comprising at least one maytansinoid linked to the cell-binding agent, wherein the maytansinoid is any of the above-described compounds;

Any of the above-described maytansinoid-cell-binding agent conjugates, wherein the cell-binding agent comprises at least one binding site of an antibody, preferably humanized or resurfaced MY9, humanized or resurfaced anti-B4, or humanized or resurfaced C242;

A pharmaceutical composition comprising an effective amount of any of the above-described maytansinoid-cell-binding agent conjugates, a pharmaceutically acceptable salt or solvate thereof, and a pharmaceutically acceptable carrier, diluent or excipient;

A method of esterification of a maytansinoid at C-3, C-14 hydroxymethyl, C-15 hydroxy, or C-20 desmethyl, with an acylated amino acid side chain where the acyl group bears a protected sulfhydryl functionality, wherein the carbon atom of the acyl group bearing the protected thiol functionality has one or two substituents, said substituents being $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition one of the substituents can be H, and wherein the acyl group has a linear chain length of at least three carbon atoms between the carbonyl functionality and the sulfur atom, said method comprising reacting a maytansinoid at C-3, C-14 hydroxymethyl, C-15 hydroxy, or C-20 desmethyl, with the acylated amino acid where the acyl group bears a protected sulfhydryl group;

A method of esterification of a maytansinoid to produce a maytansinoid ester represented by formula (IV-L), (IV-D), or (IV-D,L):

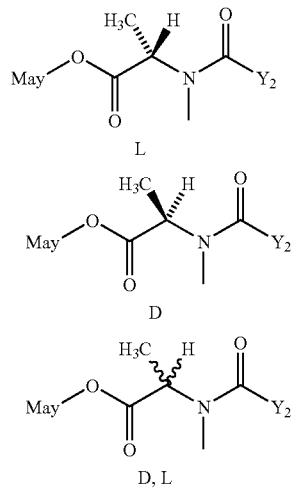

wherein:

$Y_2$ represents $(CR_7R_8)_l(CR_5R_6)_m(CR_3R_4)_nCR_1R_2SZ_2$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear cyclic alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0;

$Z_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical; and May is a maytansinoid; said method comprising reacting said May at C-3, C-14 hydroxymethyl, C-15 hydroxy, or C-20 desmethyl, with a compound of formula (III-L), (III-D), or (III-D,L):

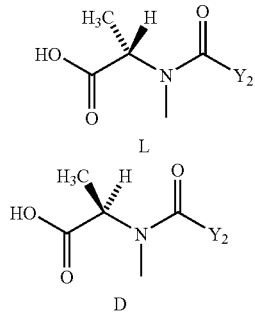

-continued

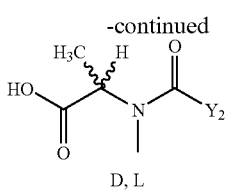

D, L wherein:

Y$_2$ represents (CR$_7$R$_8$)$_l$(CR$_5$R$_6$)$_m$(CR$_3$R$_4$)$_n$CR$_1$R$_2$SZ$_2$, wherein:

R$_1$ and R$_2$ are each independently CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition R$_2$ can be H;

R$_3$, R$_4$, R$_5$, R$_6$, R$_7$ and R$_8$ are each independently H, CH$_3$, C$_2$H$_5$, linear or branched alkyl or alkenyl having from 1 to 10 carbon atoms, cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0; and Z$_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical;

The above-described method, wherein R$_1$ is H, R$_2$ is methyl, R$_5$, R$_6$, R$_7$ and R$_8$ are each H; l and m are each 1; and n is 0;

The above-described method, wherein the compound of formula (III) is represented by formula (III-L);

The above-described method, wherein the compound of formula (III-L) is compound 15a(S,S), 15b(S,R) or a mixture of 15a(S,S) and 15b(S,R);

The above-described method, wherein the compound of formula (III-D) is compound 15(R,S), 15(R,R), or a mixture of 15(R,S) and 15(R,R);

The above-described method, wherein the compound of formula (III-D,L) is racemic N-methylalanine acylated with a carboxylic group bearing a protected thiol functionality, in which the carbon center bearing the sulfur atom is either racemic or of the R or S chirality to give compounds of the structure of 15;

The above-described method, wherein the mixture of 15a (S,S) and 15b(S,R) is made by a process comprising:

(1) reacting 4-mercaptopentanoic acid (12) with methyl methanethiolsulfonate to give compound 13;

(2) converting compound 13 into its N-hydroxysuccinimide ester 14;

(3) reacting compound 14 with N-methyl-L-alanine to give said mixture of compounds 15a(S,S) and 15b(S,R);

The above-described method, wherein compound 15a(S,S) is made by a method comprising:

(1) converting (R)-1,3-butanediol into (S)-4-(methydithio) pentanoic acid 19;

(2) converting compound 19 into its N-hydroxysuccinimide ester (20); and (3) reacting compound 20 with N-methyl-L-alanine to give said compound 15a(S,S).

The above-described method, wherein compound 15b(S, R) is made by a method comprising:

(1) converting (S)-1,3-butanediol into (R)-4-(methydithio) pentanoic acid 24;

(2) converting compound 24 into its N-hydroxysuccinimide ester (25); and (3) reacting compound 25 with N-methyl-L-alanine to give said compound 15b(S,R).

The above described method, wherein the mixture of compounds 15(R,S) and 15(R,R) is made by a process comprising:

(1) reacting 4-mercaptopentanoic acid (12) with methyl methanethiolsulfonate to give compound 13;

(2) converting compound 13 into its N-hydroxysuccinimide ester 14, (3) reacting compound 14 with N-methyl-D-alanine to give said mixture of compounds 15(R,S) and 15(R,R).

The above-described method, wherein racemic N-methylalanine acylated with a carboxylic group bearing a protected thiol functionality, in which the carbon center bearing the sulfur atom is either racemic or of the R or S chirality to give compounds of the structure of 15 is made by a process comprising:

(1) reacting 4-mercaptopentanoic acid (12) with methyl methanethiolsulfonate to give compound 13;

(2) converting compound 13 into its N-hydroxysuccinimide ester 14;

(3) reacting compound 14 with racemic N-methylalanine to give the racemic N-methylalanine acylated with a carboxylic group bearing a protected thiol functionality, in which the carbon center bearing the sulfur atom is either racemic or of the R or S chirality to give compounds of the structure 15.

The above-described method, wherein R$_1$ and R$_2$ are methyl; R$_5$, R$_6$, R$_7$ and R$_8$ are each H; l and m are each 1; and n is 0;

The above-described method, wherein the compound of formula (III-L) is compound 10(S) containing N-methyl-L-alanine;

The above-described method, wherein the compound of formula (III-D) is compound 10(R) containing N-methyl-D-alanine;

The above-described method, wherein the compound of formula (III-D,L) is compound 10(S,R) containing racemic N-methylalanine;

The above-described method, wherein the compound 10 containing N-methyl-L-alanine, N-methyl-D-alanine or racemic N-methylalanine is made by a process comprising:

(1) reacting isobutylene sulfide (5) with the anion of acetonitrile to give compound 6;

(2) hydrolyzing compound 6 to give 4-mercapto-4-methylpentanoic acid (7);

(3) converting compound 7 into disulfide 8 by reaction with methyl methanethiolsulfonate;

(4) converting compound 8 into its N-hydroxysuccinimide ester 9; and (5) reacting compound 9 with N-methyl-L-alanine, N-methyl-D-alanine, or racemic N-methylalanine to give said compound 10 containing N-methyl-L-alanine, N-methyl-D-alanine, or racemic N-methylalanine;

A method of making a maytansinoid by the method of any one of the above-described methods, separating diastereomers, if present, and purifying the maytansinoid by HPLC on cyano-bonded silica;

A method of making a maytansinoid-cell-binding agent conjugate comprising making a purified maytansinoid by any of the above-described methods, and reacting the purified maytansinoid with a cell-binding agent comprising a reactive dithio group or a sulfhydryl group.

The above-described method of making a maytansinoid-cell-binding agent conjugate, wherein the reactive dithio group is a dithiopyridyl group or a substituted dithiopyridyl group;

A method of making a maytansinoid-cell-binding agent conjugate comprising making a purified maytansinoid by any of the above-described methods, and reacting the purified maytansinoid with a cell-binding agent comprising a maleimido group or a haloacetyl group;

A method of esterification of maytansinol to give a maytansinoid of the formula $4_2'$:

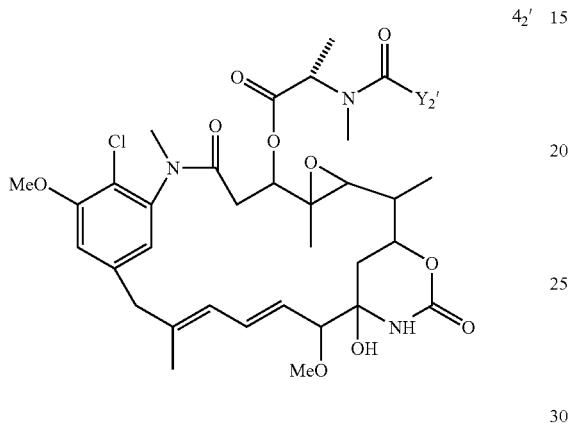

$4_2'$ wherein:

$Y_2'$ represents $(CR_7R_8)_l(CR_9\!=\!CR_{10})_p(C\!\equiv\!C)_qA_o(CR_5R_6)_mD_u(CR_{11}\!=\!CR_{12})_r(C\!\equiv\!C)_sB_t(CR_3R_4)_nCR_1R_2SZ_2$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

A, B, and D each independently is cycloalkyl or cycloalkenyl having 3 to 10 carbon atoms, simple or substituted aryl, or heterocyclic aromatic or heterocyclic radical;

$R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m, n, o, p, q, r, s, t and u are each independently 0 or an integer of from 1 to 5, provided that at least two of l, m, n, o, p, q, r, s, t and u are not zero at any one time; and $Z_2$ is SR or —COR, wherein R is linear alkyl or alkenyl having from 1 to 10 carbon atoms, branched or cyclic alkyl or alkenyl having from 3-10 carbon atoms, or simple or substituted aryl or heterocyclic aromatic or heterocyclic radical, said method comprising reacting maytansinol of the structure 11 at the C-3:

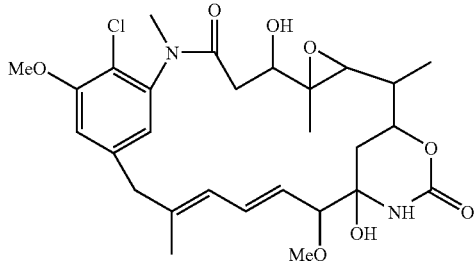

11 with a compound of formula (III'-L), (III'-D), or (III'-D, L):

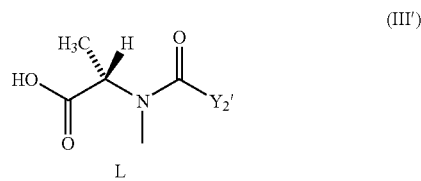

(III')

L

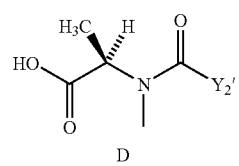

D

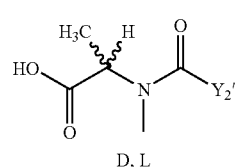

D, L wherein:

$Y_{2'}$ represents $(CR_7R_8)_l(CR_9\!=\!CR_{10})_p(C\!\equiv\!C)_qA_o(CR_5R_6)_mD_u(CR_{11}\!=\!CR_{12})_r(C\!\equiv\!C)_sB_t(CR_3R_4)_nCR_1R_2SZ_2$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

A, B, and D each, independently is cycloalkyl or cycloalkenyl having 3-10 carbon atoms, simple or substituted aryl, or heterocyclic aromatic or heterocyclic radical;

$R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m, n, o, p, q, r, s, t and u are each independently 0 or an integer of from 1 to 5, provided that at least two of l, m, n, o, p, q, r, s, t and u are not zero at any one time; and $Z_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical.

The method of esterification of maytansinol to give a maytansinoid of the formula $4_2'$, wherein the compound of formula (I) is represented by formula (I-L).

The method of esterification of maytansinol to give a maytansinoid of the formula $4_2'$, wherein $R_1$ is H and $R_2$ is methyl, A method of esterification of maytansinol to give a maytansinoid of the formula $4_2$:

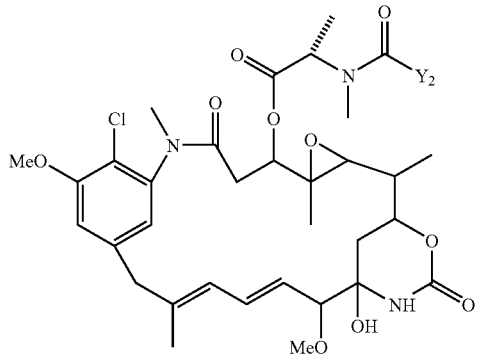

wherein:

$Y_2$ represents $(CR_7R_8)_l(CR_5R_6)_m(CR_3R_4)_nCR_1R_2SZ_2$, wherein:

$R_1$ and $R_2$ are each independently $CH_3$, $C_2H_5$, linear alkyl or alkenyl having from 1 to 10 carbon atoms, cyclic alkyl or alkenyl having from 3 to 10 carbon atoms, phenyl, substituted phenyl, or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0;

$Z_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical, said method comprising reacting maytansinol of the structure 11:

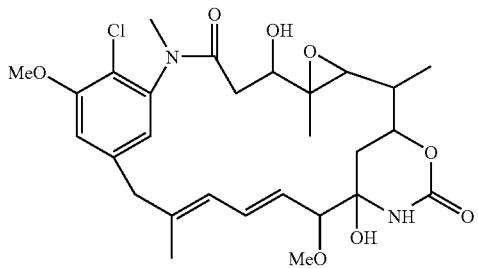

at the C-3 position with a compound of formula (III-L), (III-D), or (III-D, L):

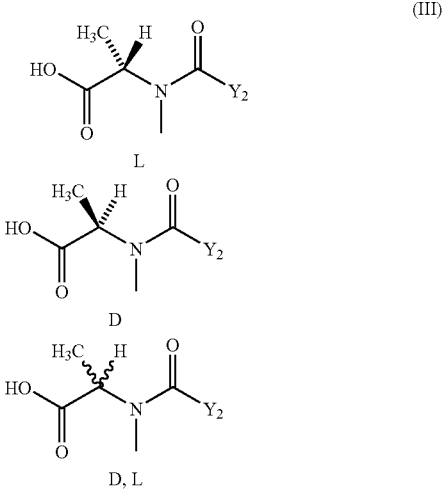

wherein:

$Y_2$ represents $(CR_7R_8)_l(CR_5R_6)_m(CR_3R_4)_nCR_1R_2SZ_2$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0;

$Z_2$ is SR or COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical;

The above-described method of esterification of maytansinol to give the maytansinoid of formula 4a, wherein the compound of formula (III) is represented by formula (III-L);

The above-described method of esterification of maytansinol to give maytansinoids of formula 4a, wherein said compound of formula (III-L) is compound 15a(S,S), 15b(S,R) or a mixture of 15a(S,S) and 15b(S,R);

The above-described method of esterification of maytansinol to give maytansinoids of formula 4a, wherein said compound of formula (III-D) is compound 15(R,S), 15(R,R), or a mixture of 15(R,S) and 15(R,R);

The above-described method of esterification of maytansinol to give maytansinoids of formula 4a, wherein said compound of formula (III-D,L) is racemic N-methylalanine acylated with a carboxylic group bearing a protected thiol functionality, in which the carbon center bearing the sulfur atom is either racemic or of R or S chirality to give compounds of the structure of 15;

The above-described method of esterification of maytansinol to give maytansinoids of formula 4a, wherein the mixture of 15a(S,S) and 15b(S,R) is made by a process comprising:

(1) reacting 4-mercaptopentanoic acid (12) with methyl methanethiolsulfonate to give compound 13;

(2) converting compound 13 into its N-hydroxysuccinimide ester 14;

(3) reacting compound 14 with N-methyl-L-alanine to give said mixture of compounds 15a(S,S) and 15b(S,R);

The above-described method of esterification of maytansinol, wherein said compound 15a(S,S) is made by a method comprising:

(1) converting (R)-1,3-butanediol into (S)-4-(methydithio)pentanoic acid 19;

(2) converting compound 19 into its N-hydroxysuccinimide ester (20); and (3) reacting compound 20 with N-methyl-L-alanine to give the compound 15a(S,S).

The above-described method of esterification of maytansinol, wherein said compound 15b(S,R) is made by a method comprising:

(1) converting (S)-1,3-butanediol into (R)-4-(methydithio)pentanoic acid 24;

(2) converting compound 24 into its N-hydroxysuccinimide ester (25); and (3) reacting compound 25 with N-methyl-L-alanine to give the compound 15b(S,R);

The above-described method of esterification of maytansinol to give maytansinoids of formula 4a, wherein the mixture of compounds 15(R,S) and 15(R,R) can be made by a process comprising:

(1) reacting 4-mercaptopentanoic acid (12) with methyl methanethiolsulfonate to give compound 13;

(2) converting compound 13 into its N-hydroxysuccinimide ester 14;

(3) reacting compound 14 with N-methyl-D-alanine to give said mixture of compounds 15(R,S) and 15(R,R,).

The above-described method of esterification of maytansinol to give maytansinoids of formula 4a, wherein racemic N-methylalanine acylated with a carboxylic group bearing a protected thiol functionality, in which the carbon center bearing the sulfur atom is either racemic or of the R or S chirality to give compounds of the structure of 15 is made by a process comprising:

(1) reacting 4-mercaptopentanoic acid (12) with methyl methanethiolsulfonate to give compound 13;

(2) converting compound 13 into its N-hydroxysuccinimide ester 14;

(3) reacting compound 14 with racemic N-methylalanine to give the racemic N-methylalanine acylated with a carboxylic group bearing a protected thiol functionality, in which the carbon center bearing the sulfur atom is either racemic or of the R or S chirality to give compounds of the structure 15.

The above-described method of esterification of maytansinol to give maytansinoids of formula 4b, wherein $R_1$ and $R_2$ are methyl; $R_5$, $R_6$, $R_7$, $R_8$ are each H; l and m are 1; and n is 0;

The above-described method of esterification of maytansinol to give maytansinoids of formula 4b, wherein said compound of formula (III-L) is compound 10 containing N-methyl-L-alanine;

The above-described method of esterification of maytansinol to give maytansinoids of formula 4b, wherein said compound of formula (III-D) is compound 10 containing N-methyl-D-alanine;

The above-described method of esterification of maytansinol to give maytansinoids of formula 4b, wherein said compound of formula (III-D,L) is compound 10 containing racemic N-methylalanine;

The above-described method of esterification of maytansinol to give maytansinoids of formula 4b, wherein the compound 10 containing N-methyl-L-alanine, N-methyl-D-alanine or racemic N-methylalanine is made by a process comprising:

(1) reacting isobutylene sulfide (5) with the anion of acetonitrile to give compound 6;

(2) hydrolyzing compound 6 to give 4-mercapto-4-methylpentanoic acid (7);

(3) converting compound 7 into the disulfide 8 by reaction with methyl methanethiolsulfonate;

(4) converting compound 8 into its N-hydroxysuccinimide ester 9; and (5) reacting compound 9 with N-methyl-L-alanine, N-methyl-D-alanine, or racemic N-methylalanine to give compound 10 containing N-methyl-L-alanine, N-methyl-D-alanine or racemic N-methylalanine;

The above-described method of esterification of maytansinol with 10, followed by separating diastereomers, if present, and purifying the maytansinoid by HPLC on cyano-bonded silica, further comprising reduction of the disulfide bond, to give maytansinoids of formula 4b;

A method of making a maytansinoid-cell-binding agent conjugate comprising making a purified maytansinoid by any of the above-described methods of esterification of maytansinol to give maytansinoids of formula 4b, and reacting the maytansinoid with a cell-binding agent comprising a sulfhydryl group or a reactive dithio group, preferably, a dithiopyridyl group or a substituted dithiopyridyl group;

A method of making a maytansinoid-cell-binding agent conjugate comprising making a purified maytansinoid by any of the above-described methods of esterification of maytansinol to give maytansinoids of formula 4b, and reacting the maytansinoid with a cell-binding agent comprising a maleimido or an haloacetyl group.

Methods of therapy using the above-described conjugates.

Compounds of formula (III):

wherein:

$Y_2$ represents $(CR_7R_8)_l(CR_5R_6)_m(CR_3R_4)_nCR_1R_2SZ_2$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0; and $Z_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical.

Compounds 10 (S), 10 (R) or racemic 10;

A method of making compound 10 containing N-methyl-L-alanine, N-methyl-D-alanine, or racemic N-methylalanine comprising:

(1) reacting isobutylene sulfide (5) with the anion of acetonitrile to give compound 6;

(2) hydrolyzing compound 6 to give 4-mercapto-4-methylpentanoic acid (7);

(3) converting compound 7 into disulfide 8 by reaction with methylmethanethiolsulfonate;

(4) converting compound 8 into its N-hydroxysuccinimide ester 9; and (5) reacting compound 9 with N-methyl-L-alanine, N-methyl-D-alanine, or racemic N-methylalanine to give said compound 10 containing N-methyl-L-alanine, N-methyl-D-alanine, or racemic N-methylalanine.

A mixture of compounds 15a(S,S) and 15b(S,R);

A method of making a mixture of compounds 15a(S,S) and 15b(S,R), comprising:

(1) reacting 4-mercaptopentanoic acid (12) with methylmethanethiolsulfonate to give compound 13;

(2) converting compound 13 into its N-hydroxysuccinimide ester (14); and (3) reacting compound 14 with N-methyl-L-alanine to give said mixture of compounds 15a(S,S) and 15b(S,R);

A mixture of compounds 15(R,S) and 15(R,R).

A method of making a mixture of compounds 15(R,S) and 15(R,R) comprising:

(1) reacting 4-mercaptopentanoic acid (12) with methyl methanethiolsulfonate to give compound 13;

(2) converting compound 13 into its N-hydroxysuccinimide ester 14;

(3) reacting compound 14 with N-methyl-D-alanine to give said mixture of compounds 15(R,S) and 15(R,R).

Racemic N-methylalanine acylated with a carboxylic group bearing a protected thiol functionality, in which the carbon center bearing the sulfur atom is either racemic or of the R or S chirality to give compounds of the structure of 15.

A method of making racemic N-methylalanine acylated with a carboxylic group bearing a protected thiol functionality, in which the carbon center bearing the sulfur atom is either racemic or of R or S chirality to give compounds of the structure 15, comprising:

(1) reacting 4-mercaptopentanoic acid (12) with methyl methanethiolsulfonate to give compound 13;

(2) converting compound 13 into its N-hydroxysuccinimide ester 14;

(3) reacting compound 14 with racemic N-methylalanine to give the racemic N-methylalanine acylated with a carboxylic group bearing a protected thiol functionality, in which the carbon center bearing the sulfur atom is either racemic or of the R or S chirality to give compounds of the structure 15.

Compound 15a(S,S);

Compound 15b(S,R);

A method of making compound 15a(S,S) comprising:

(1) converting (R)-1,3-butanediol into (S)-4-(methydithio) pentanoic acid 19;

(2) converting compound 19 into its N-hydroxysuccinimide ester (20); and (3) reacting compound 20 with N-methyl-L-alanine to give said compound 15a(S,S);

A method of making compound 15b(S,R) comprising:

(1) converting (S)-1,3-butanediol into (R)-4-(methydithio) pentanoic acid 24;

(2) converting compound 24 into its N-hydroxysuccinimide ester (25); and (3) reacting compound 25 with N-methyl-L-alanine to give said compound 15b(S,R).

A pharmaceutical composition comprising an effective amount of any of the above-described maytansinoid compounds, a pharmaceutically acceptable salt or solvate thereof, and a pharmaceutically acceptable carrier, diluent or excipient;

The above-described pharmaceutical composition comprising a maytansinoid compound, further comprising an antibody.

A method for inducing cell death in selected cell populations comprising contacting target cells or tissue containing target cells with an effective amount of any of the above-described maytansinoid-cell-binding agents, salts or solvates thereof.

BRIEF DESCRIPTION OF THE FIGURES

FIGS. 4a,b are graphs that show the in vitro potency of new maytansinoids of the present invention.

FIGS. 4c,d are graphs that compare the in vitro potency of new maytansinoids of the present invention with those previously described.

FIG. 6 is a graph that shows the in vitro potency of cell-binding agent-maytansinoid conjugates of the present invention.

FIG. 7 is a graph that compares the in vivo anti-tumor efficacy of huC242-maytansinoids of the present invention with huC42 conjugates of previously described maytansinoids, against HT-29 human colon tumor xenografts.

FIG. 8 is a graph that compares the in vivo anti-tumor efficacy of huC242-maytansinoids of the present invention with huC242 conjugates of previously described maytansinoids, against COLO 205 human colon tumor xenografts.

FIG. 9 is a graph that compares the in vivo anti-tumor efficacy of MY9-6-maytansinoids of the present invention with MY9-6 conjugates of previously described maytansinoids, against HL60 promyelocytic myeloid leukemia xenografts.

FIG. 10 shows the result of the in vitro cytotoxicity evaluation of the conjugate huMy9-6-DM4 with target HL-60 cells and non-target Namalwa cells.

FIG. 11 shows the in vivo efficacy evaluation of the conjugate huMy9-6-DM4 against human HL-60 xenograft tumors in SCID mice and compares it with that of a huMy9-6 conjugate of a previously described maytansinoid (huMy9-6-DM1).

FIG. 12 shows the result of the in vitro cytotoxicity evaluation of the conjugate huB4-DM4 with target Ramos cells and non-target Colo 205 cells.

FIG. 13a shows the in vivo efficacy evaluation of the conjugate huB4-DM4 against human Ramos xenograft tumors in SCID mice, and FIG. 13b shows the changes in the body weights of the animals during the test period.

DETAILED DESCRIPTION OF THE INVENTION

Figure 1:
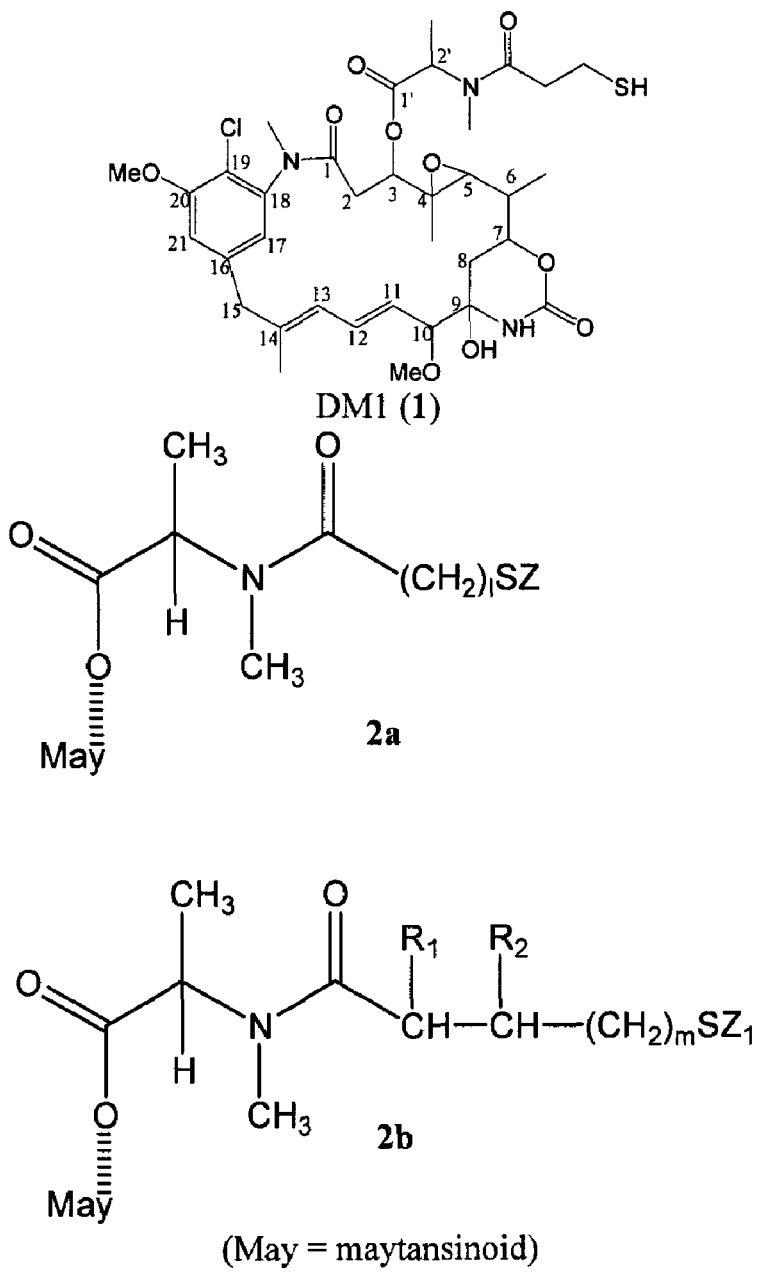
FIG. 1 shows the structures of previously described maytansinoids.

This invention discloses new, sterically hindered thiol and disulfide-containing maytansinoids in which the α-carbon atom bearing the sulfur atom bears one or two alkyl substituents. The invention also discloses a process for the synthesis of these novel maytansinoids. Novel compounds that are useful as intermediates in the synthesis of the new maytansinoids are further disclosed. In addition, this invention discloses the preparation of conjugates of these novel maytansinoids with cell-binding agents.

The art reveals that it is extremely difficult to modify existing drugs without diminishing their cytotoxic potential. The disclosed invention overcomes this problem by teaching a method of synthesizing new maytansinoid molecules containing a sterically hindered thiol or disulfide moiety. The disclosed novel maytansinoids preserve, and in some cases even enhance, the cytotoxic potency of the previously described maytansinoids.

The maytansinoid-cell-binding agent conjugates permit the full measure of the cytotoxic action of the maytansinoids to be applied in a targeted fashion against unwanted cells only, thereby avoiding side effects due to damage to non-targeted healthy cells. Thus, the invention provides useful agents, and novel methods for making the same, for the elimination of diseased or abnormal cells that are to be killed or lysed, such as tumor cells (particularly solid tumor cells), virus infected cells, microorganism infected cells, parasite infected cells, autoimmune cells (cells that produce autoantibodies), activated cells (those involved in graft rejection or graft vs. host disease), or any other type of diseased or abnormal cells, while exhibiting a minimum of side effects.

Thus, this invention teaches a method for the production of improved cytotoxic conjugates comprising novel maytansinoids and cell-binding agents, with vastly improved biological activity as compared to previously described maytansinoids and cell-binding agents. The invention further teaches a method for the synthesis of maytansinoid derivatives that possess a sterically hindered thiol or disulfide moiety that allows chemical linkage to a cell-binding agent while displaying high cytotoxicity either in bound form or in released form or in both states. The cytotoxic conjugate according to the present invention comprises one or more maytansinoids linked to a cell-binding agent. In order to link the maytansinoid to a cell-binding agent, the maytansinoid must first be modified.

Maytansinoids that can be used in the present invention to produce the maytansinoids that are capable of being linked to a cell-binding agent are well known in the art and can be isolated from natural sources according to known methods or prepared synthetically according to known methods.

Examples of suitable maytansinoids include maytansinol and maytansinol analogues. Examples of suitable maytansinol analogues include those having a modified aromatic ring and those having modifications at other positions.

Specific examples of suitable analogues of maytansinol having a modified aromatic ring include:

(1) C-19-dechloro (U.S. Pat. No. 4,256,746) (prepared by LAH reduction of ansamitocin P2);

(2) C-20-hydroxy (or C-20-demethyl)+/−C-19-dechloro (U.S. Pat. Nos. 4,361,650 and 4,307,016) (prepared by demethylation using *Streptomyces* or *Actinomyces* or dechlorination using LAH); and (3) C-20-demethoxy, C-20-acyloxy (—OCOR), +/−dechloro (U.S. Pat. No. 4,294,757) (prepared by acylation using acyl chlorides).

Specific examples of suitable analogues of maytansinol having modifications of other positions include:

(1) C-9-SH (U.S. Pat. No. 4,424,219) (prepared by the reaction of maytansinol with $H_2S$ or $P_2S_5$);

(2) C-14-alkoxymethyl (demethoxy/$CH_2OR$) (U.S. Pat. No. 4,331,598);

(3) C-14-hydroxymethyl or acyloxymethyl ($CH_2OH$ or $CH_2OAc$) (U.S. Pat. No. 4,450,254) (prepared from *Nocardia*);

(4) C-15-hydroxy/acyloxy (U.S. Pat. No. 4,364,866) (prepared by the conversion of maytansinol by *Streptomyces*);

(5) C-15-methoxy (U.S. Pat. Nos. 4,313,946 and 4,315,929) (isolated from *Trewia nudiflora*);

(6) C-18-N-demethyl (U.S. Pat. Nos. 4,362,663 and 4,322,348) (prepared by the demethylation of maytansinol by *Streptomyces*); and (7) 4,5-deoxy (U.S. Pat. No. 4,371,533) (prepared by the titanium trichloride/LAH reduction of maytansinol).

In order to link the maytansinoid to the cell-binding agent, the maytansinoid comprises a linking moiety. The linking moiety contains a chemical bond that allows for the release of fully active maytansinoids at a particular site. Suitable chemical bonds are well known in the art and include disulfide bonds, acid labile bonds, photolabile bonds, peptidase labile bonds and esterase labile bonds. Preferred are disulfide bonds.

The disclosure of U.S. Pat. No. 5,208,020, incorporated herein by reference, teaches the production of maytansinoids bearing such bonds.

According to the present invention, the linking moiety comprises a sterically hindered thiol or disulfide moiety.

Particularly preferred maytansinoids comprising a linking moiety that contains a reactive chemical group are C-3 esters of maytansinol and its analogs where the linking moiety contains a sterically hindered thiol or disulfide bond.

Many positions on maytansinoids can serve as the position to chemically link the linking moiety. For example, the C-3 position having a hydroxyl group, the C-14 position modified with hydroxymethyl, the C-15 position modified with hydroxy and the C-20 position having a hydroxy group are all expected to be useful. However the C-3 position is preferred and the C-3 position of maytansinol is especially preferred.

Further, while the synthesis of esters of maytansinol having a linking moiety is described below in terms of a disulfide bond containing linking moieties at the C-3 position, one of skill in the art will understand that linking moieties with other chemical bonds, as described above, can also be used with the present invention, as can other maytansinoids and other linking positions, as described above.

Figure 2:
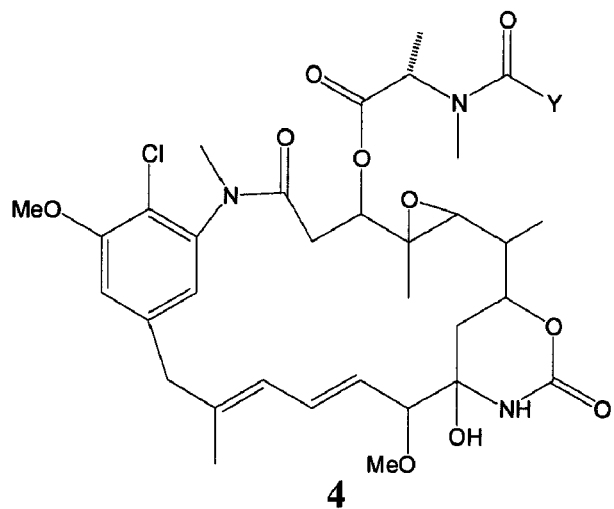
FIG. 2 shows the structures of some of the maytansinoids of the present invention.

The structures of various maytansinoids of the present invention are represented in FIG. 2. The synthesis of maytansinoids having a sterically hindered thiol or disulfide moiety can be described by reference to FIG. 3. Many of the exemplified methods below utilize the thiol-containing maytansinoids $N^{2'}$-deacetyl-$N^{2'}$-(4-mercapto-1-oxopentyl)-maytansine (termed DM3) and $N^{2'}$-deacetyl-$N^{2'}$-(4-methyl-4- mercapto-1-oxopentyl)-maytansine (termed DM4). DM3 (4a) and DM4 (4b) are represented by the following structural formulae:

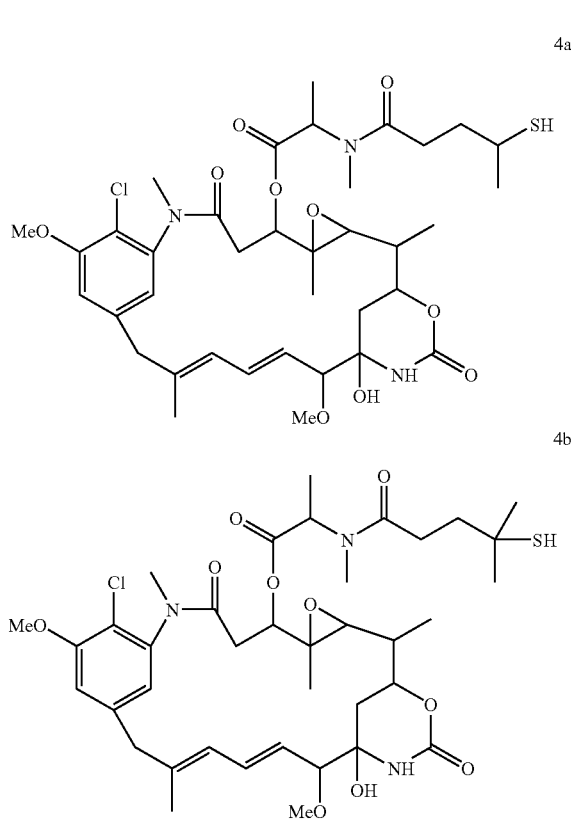

The in vitro cytotoxicity of the new sterically hindered thiol and disulfide-containing maytansinoids of the invention can be evaluated for their ability to suppress proliferation of various unwanted cell lines in vitro (FIG. 4). For example, cell lines such as the human breast carcinoma line SK-Br-3, or the human epidermoid carcinoma cell line KB, can be used for the assessment of cytotoxicity of these new maytansinoids. Cells to be evaluated can be exposed to the compounds for 72 hours and the surviving fractions of cells measured in direct assays by known methods. $IC_{50}$ values can then be calculated from the results of the assays.

Production of Maytansinoids Having a Sterically Hindered Thiol or Disulfide Moiety The novel maytansinoids of the invention are those having, at C-3, C-14 hydroxymethyl, C-15 hydroxy, or C-20 desmethyl, an acylated amino acid side chain with an acyl group bearing a hindered sulfhydryl group, wherein the carbon atom of the acyl group bearing the thiol functionality has one or two substituents, said substituents being $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition one of the substituents can be H, and wherein the acyl group has a linear chain length of at least three carbon atoms between the carbonyl functionality and the sulfur atom.

Preferably, the maytansinoid compounds are represented by formula 4':

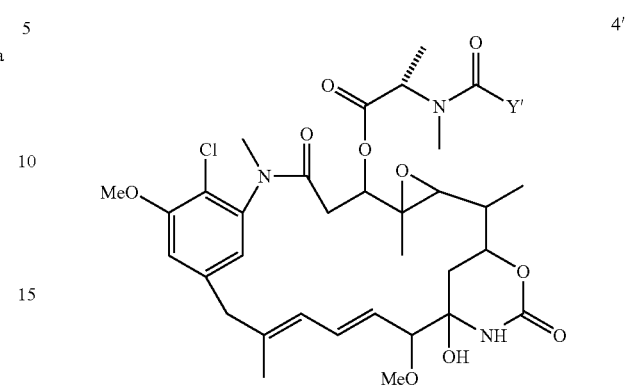

wherein:

Y' represents $(CR_7R_8)_l(CR_9\!=\!CR_{10})_p(C\!\equiv\!C)_qA_o(CR_5R_6)_m\ D_u(CR_{11}\!=\!CR_{12})_r(C\!\equiv\!C)_sB_t(CR_3R_4)_nCR_1R_2SZ$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H; A, B, D are cycloalkyl or cycloalkenyl having 3-10 carbon atoms, simple or substituted aryl or heterocyclic aromatic or heterocyclic radical;

$R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m, n, o, p, q, r, s, t and u are each independently 0 or an integer of from 1 to 5, provided that at least two of l, m, n, o, p, q, r, s, t and u are not zero at any one time;

Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical.

In a preferred embodiments of the compound represented by formula 4', $R_1$ is H, $R_2$ is methyl and Z is H; $R_1$ and $R_2$ are methyl and Z is H; $R_1$ is H, $R_2$ is methyl, and Z is —$SCH_3$; or $R_1$ and $R_2$ are methyl, and Z is —$SCH_3$.

More preferably, the maytansinoids are compounds represented by formula (I-L), (I-D), or (I-D,L):

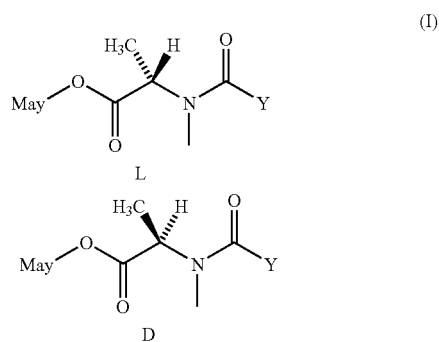

-continued

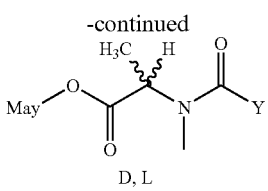
D, L wherein:

Y represents $(CR_7R_8)_l(CR_5R_6)_m(CR_3R_4)_nCR_1R_2SZ$, wherein:

$R_1$ and $R_2$ are each independently $CH_3$, $C_2H_5$, linear alkyl or alkenyl having from 1 to 10 carbon atoms, cyclic alkyl or alkenyl having from 3 to 10 carbon atoms, phenyl, substituted phenyl, or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0;

Z is H, SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical; and May represents a maytansinoid which bears the side chain at C-3, C-14 hydroxymethyl, C-15 hydroxy or C-20 desmethyl.

More preferred is the C-3 ester, which is a compound represented by formula 4:

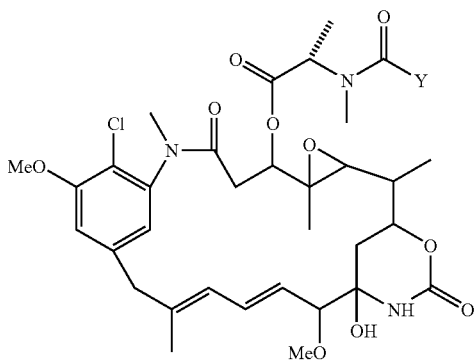

4 wherein the substituents are as defined above.

Especially preferred are any of the above-described compounds, wherein $R_1$ is H, $R_2$ is methyl, $R_5$, $R_6$, $R_7$ and $R_8$ are each H, l and m are each 1, n is 0, and Z is H; those compounds wherein $R_1$ and $R_2$ are methyl, $R_5$, $R_6$, $R_7$, $R_8$ are each H, l and m are 1, n is 0, and Z is H; those compounds wherein $R_1$ is H, $R_2$ is methyl, $R_5$, $R_6$, $R_7$, and $R_8$ are each H, l and m are each 1, n is 0, and Z is —SCH$_3$; and those compounds $R_1$ and $R_2$ are methyl, $R_5$, $R_6$, $R_7$, $R_8$ are each H, l and m are 1, n is 0, and Z is —SCH$_3$. Further, the L-alanyl stereoisomer is preferred as it is the most useful for the conjugates of the invention.

Preferred embodiments of formula 4 include DM3 and DM4, i.e., the maytansinoid of formula 4 where Z is H, $R_1$ is H, $R_2$ is methyl, $R_5$, $R_6$, $R_7$, and $R_8$ are each H, and l and m are 1, and n is 0 (DM3, compound 4a); the maytansinoid of formula 4 where Z is H, $R_1$ and $R_2$ are both methyl, $R_5$, $R_6$, $R_7$, and $R_8$ are each H, l and m are 1, and n is 0 (DM4. compound 4b); the maytansinoid of formula 4 wherein $R_1$ is H, $R_2$ is methyl, $R_5$, $R_6$, $R_7$, and $R_8$ are each H, l and m are each 1, n is 0, and Z is —SCH$_3$; and the maytansinoid of formula 4 wherein $R_1$ and $R_2$ are methyl, $R_5$, $R_6$, $R_7$, $R_8$ are each H, l and m are 1, n is 0, and Z is —SCH$_3$.

Examples of linear alkyls or alkenyls having from 1 to 10 carbon atoms include, but are not limited to, methyl, ethyl, propyl, butyl, pentyl, hexyl, propenyl, butenyl and hexenyl.

Examples of branched alkyls or alkenyls having from 3 to 10 carbon atoms include, but are not limited to, isopropyl, isobutyl, sec.-butyl, tert.-butyl, isopentyl, 1-ethyl-propyl, isobutenyl and isopentenyl.

Examples of cyclic alkyls or alkenyls having from 3 to 10 carbon atoms include, but are not limited to, cyclopropyl, cyclobutyl, cyclopentyl, cyclohexyl, cyclopentenyl, and cyclohexenyl.

Simple aryls include aryls having 6 to 10 carbon atoms, and substituted aryls include aryls having 6 to 10 carbon atoms bearing at least one alkyl substituent containing from 1 to 4 carbon atoms, or alkoxy substituent such as methoxy, ethoxy, or a halogen substituent or a nitro substituent.

Examples of simple aryl that contain 6 to 10 carbon atoms include phenyl and naphthyl.

Examples of substituted aryl include nitrophenyl, dinitrophenyl.

Heterocyclic aromatic radicals include groups that have a 3 to 10-membered ring containing one or two heteroatoms selected from N, O or S.

Heterocyclic alkyl radicals include cyclic compounds, comprising 3 to 10-membered ring systems, containing one or two heteroatoms, selected form N, O or S.

Examples of heterocyclic aromatic radicals include pyridyl, nitro-pyridyl, pyrollyl, oxazolyl, thienyl, thiazolyl, and furyl.

Examples of heteroalkyl radicals include dihydrofuryl, tetrahydrofuryl, tetrahydropyrollyl, piperidinyl, piperazinyl, and morpholino.

Novel maytansinoids having a sterically hindered thiol or disulfide moiety may be prepared by the following newly disclosed methods:

Synthesis of Maytansinoids.

Figure 3A:
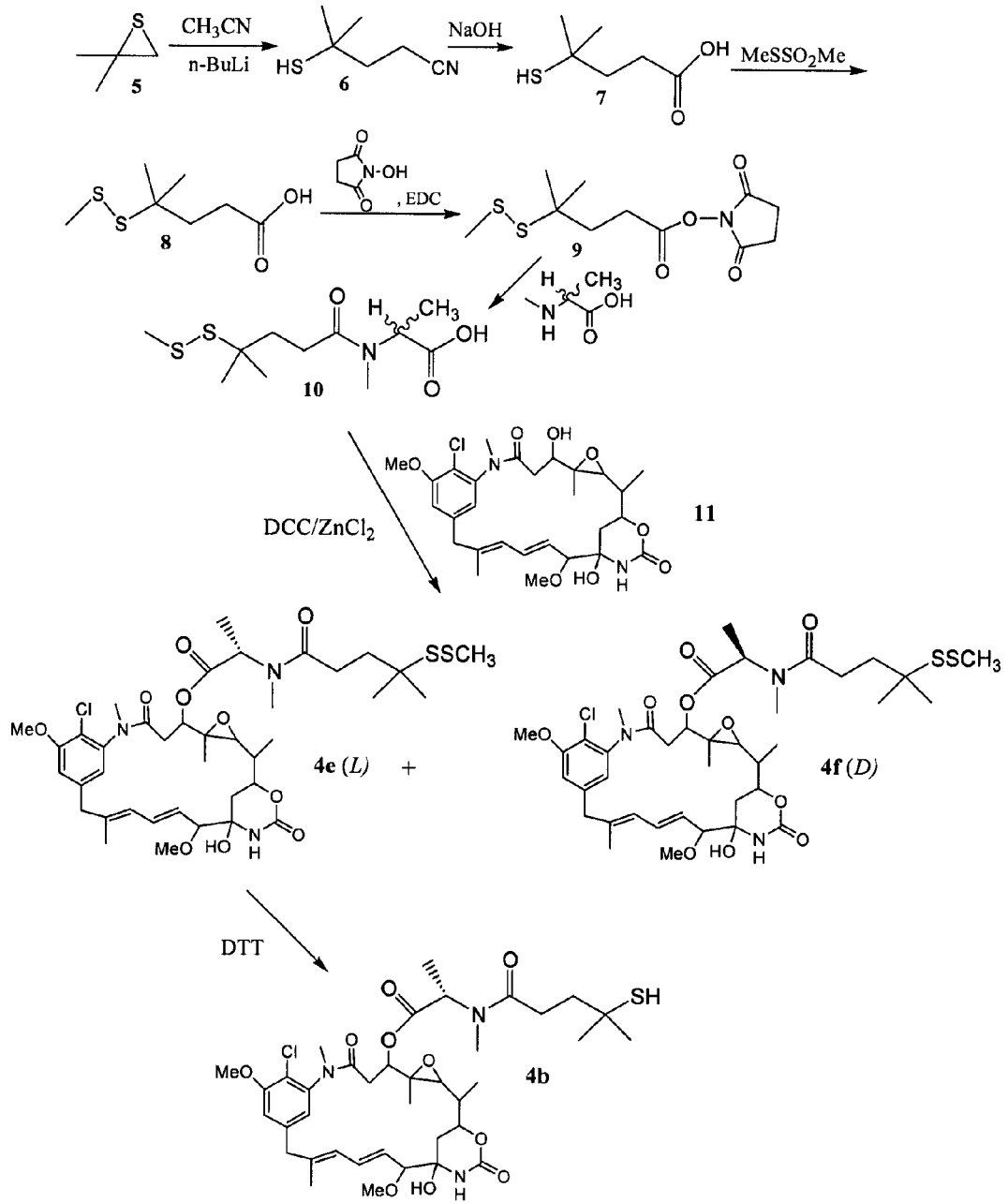
FIGS. 3a-d show schemes for the synthesis of representative maytansinoids of the present invention.

FIG. 3a shows the steps in the synthesis of maytansinoid DM4 (4b). Isobutylene sulfide (5) is reacted with the anion of acetonitrile to give the mercapto compound 6. Hydrolysis of 6 with base provided 4-mercapto-4-methylpentanoic acid (7). Conversion of 7 into disulfide 8 is achieved by reaction with methyl methanethiolsulfonate (MeSSO$_2$Me). Conversion of 8 into the N-hydroxysuccinimide ester 9 followed by reaction with N-methyl-L-alanine provided the carboxylic acid 10, which was purified by column chromatography over silica gel. Reaction of 10 with maytansinol (11) in the presence of N,N'-dicyclohexylcarbodiimide (DCC) and zinc chloride gave a mixture of the N-acyl-N-methyl-L-alanyl maytansinoid L-DM4SMe, (4e) and the N-acyl-N-methyl-D-alanyl maytansinoid D-DM4SMe (4f). The mixture of diastereomers was separated by HPLC, using a cyano-bonded column. The desired L-amino acid-containing isomer 4e was collected and reduced with dithiothreitol to give the thiol-containing L-aminoacyl maytansinoid DM4 (4b), which was again purified by HPLC, using a cyano-bonded column.

Figure 3B:
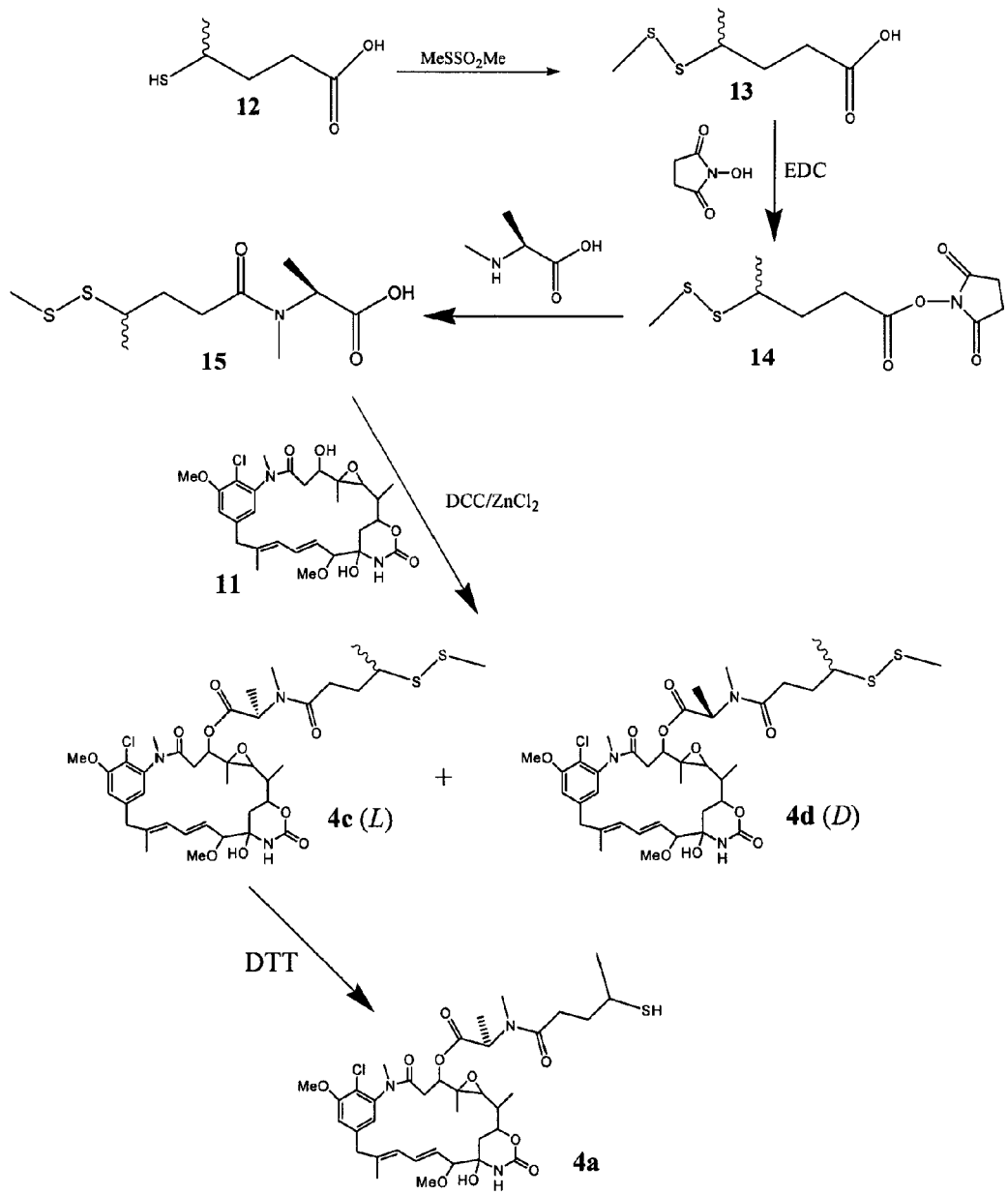

FIG. 3b shows the steps in the synthesis of maytansinoid DM3 (4a). 4-Mercaptopentanoic acid (12) was converted into the methyldisulfide by reaction with methyl methanethiolsulfonate to give 13. Conversion of 13 into the N-hydroxysuccinimide ester 14 followed by reaction with N-methyl-L-alanine provided the carboxylic acid 15, which was purified by column chromatography over silica gel. Reaction of 15 with maytansinol (11) in the presence of N,N'-dicyclohexylcarbodiimide (DCC) and zinc chloride gave a mixture of the N-acyl-N-methyl-L-alanyl maytansinoid L-DM3SSMe, (4c) and the N-acyl-N-methyl-D-alanyl maytansinoid D-DM3SSMe (4d). The mixture of diastereomers was separated by HPLC, using a cyano-bonded column. The desired L-amino acid-containing isomer was collected and reduced with dithiothreitol to give the mercapto-L-amino acid-containing maytansinoid DM3 (4a), which was again purified by HPLC, using a cyano-bonded column.

Figure 3C:
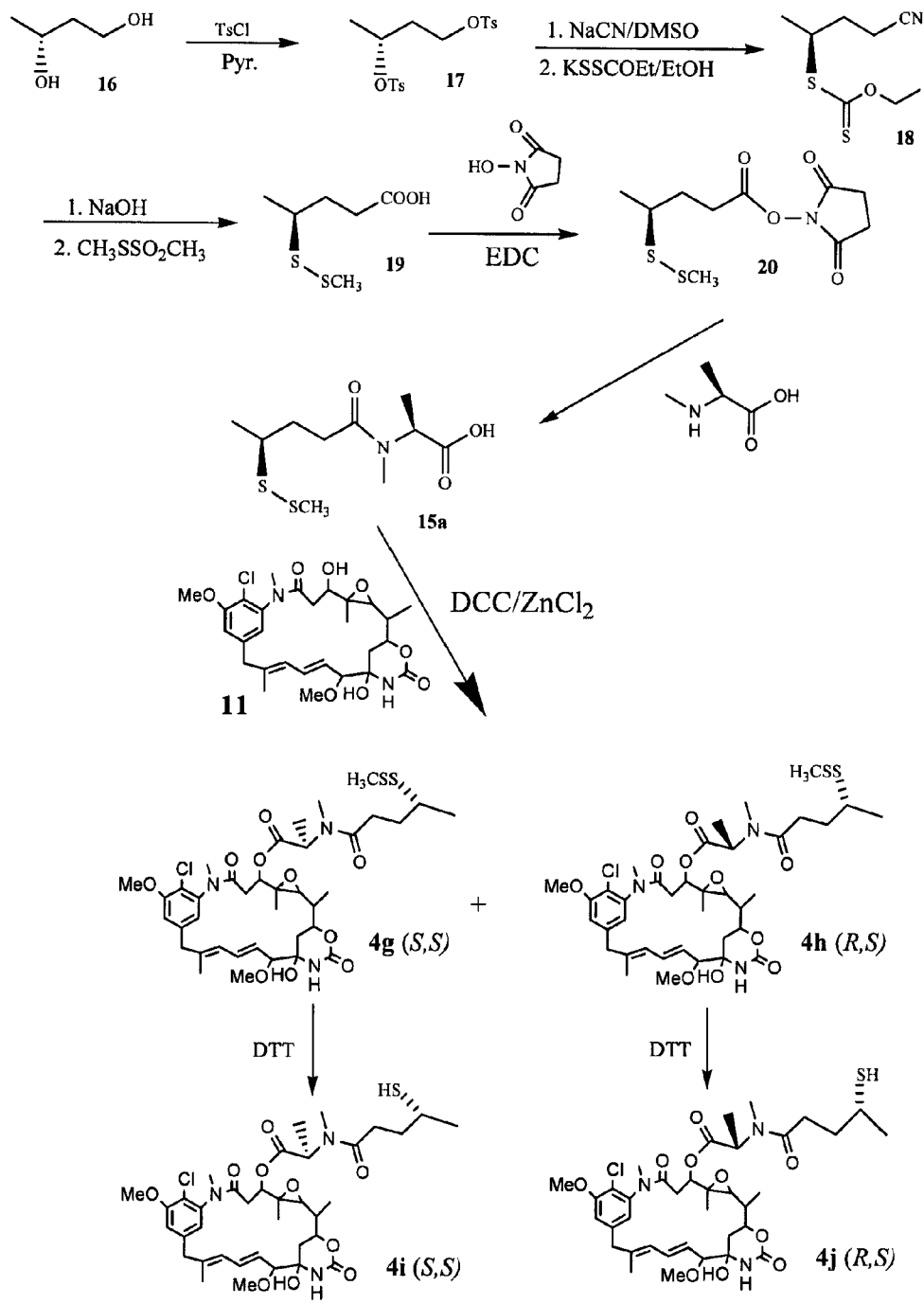

FIGS. 3c and d show the synthesis of DM3 bearing either the (S)-4-methyldithio-1-oxopentyl moiety or the (R)-4-methyldithio-1-oxo-pentyl moiety. Conversion or (R)-1,3-butanediol (16) into its ditosylate 17, followed by sequential reaction with sodium cyamide and potassium ethyl xanthate gave nitrile 18 (FIG. 3c). Base hydrolysis, followed by disulfide exchange gave (S)-4-methydithio-pentanoic acid 19. Conversion of 19 into the succinimidyl ester 20, followed by reaction with N-methyl-L-alanine gave N-methyl-N-[4-(S)-methyldithio-1-oxo-pentyl]-S-alanine (15a). Reaction with maytansinol, as described above for compound 15, gave the two diastereomers of L-DM3SMe 4g and 4h. Similarly, (S)-1,3-butanediol (21) was converted into (R)-4-methydithio-pentanoic acid 24 and then into 15b. Reaction with maytansinol, as described above, gave the two diastereomers of DM3SMe, 4k and 4l.

Thus the present invention provides a method of esterification of a maytansinoid at C-3, C-14 hydroxymethyl, C-15 hydroxy, or C-20 desmethyl, with an acylated amino acid side chain where the acyl group bears a protected sulfhydryl group, wherein the carbon atom of the acyl group bearing the protected thiol functionality has one or two substituents, said substituents being $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition one of the substituents can be H, and wherein the acyl group has a linear chain length of at least three carbon atoms between the carbonyl functionality and the sulfur atom, said method comprising reacting a maytansinoid at C-3, C-14 hydroxymethyl, C-15 hydroxy, or C-20 desmethyl, said method comprising reacting a maytansinoid at C-3, C-14 hydroxymethyl, C-15 hydroxy, or C-20 desmethyl, with the acylated amino acid where the acyl group bears a protected sulfhydryl group.

In a preferred embodiment, the present invention provides a method of esterification of maytansinol to give a maytansinoid of the formula $4_2'$:

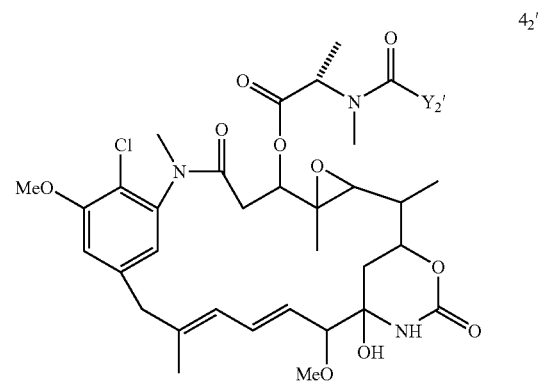

wherein:

$Y_2'$ represents $(CR_7R_8)_l(CR_9=CR_{10})_p(C\equiv C)_qA_o$ $(CR_5R_6)_mD_u(CR_{11}=CR_{12})_r(C\equiv C)_sB_t(CR_3R_4)_nCR_1R_2SZ_2$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

A, B, and D each independently is cycloalkyl or cycloalkenyl having 3-10 carbon atoms, simple or substituted aryl, or heterocyclic aromatic or heterocyclic radical;

$R_3$, $R_4$, $R_5$, $R_6$, $R_7$, $R_8$, $R_9$, $R_{10}$, $R_{11}$, and $R_{12}$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m, n, o, p, q, r, s, t and u are each independently 0 or an integer of from 1 to 5, provided that at least two of l, m, n, o, p, q, r, s, t and u are not zero at any one time; and $Z_2$ is SR or —COR, wherein R is linear alkyl or alkenyl having from 1 to 10 carbon atoms, branched or cyclic alkyl or alkenyl having from 3-10 carbon atoms, or simple or substituted aryl or heterocyclic aromatic or heterocyclic radical, said method comprising reacting maytansinol of the structure 11 at the C-3:

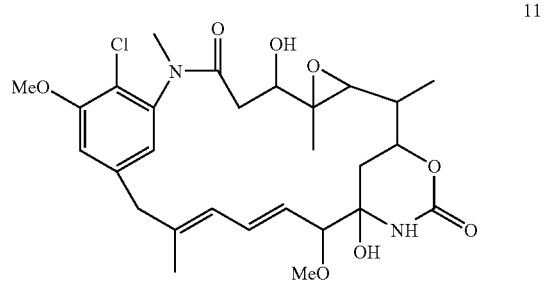

with a compound of formula (III'-L), (III'-D), or (III'-D, L):

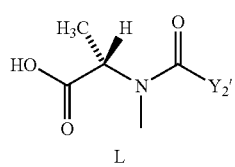

(III')

L

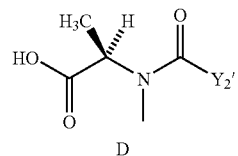

D

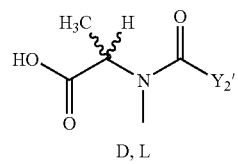

D, L wherein:

Y$_{2'}$ represents (CR$_7$R$_8$)$_l$(CR$_9$=CR$_{10}$)$_p$(C≡C)$_q$A$_o$(CR$_5$R$_6$)$_m$D$_u$(CR$_{11}$=CR$_{12}$)$_r$(C≡C)$_s$B$_t$(CR$_3$R$_4$)$_n$CR$_1$R$_2$SZ$_2$, wherein:

R$_1$ and R$_2$ are each independently CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition R$_2$ can be H;

A, B, and D each, independently is cycloalkyl or cycloalkenyl having 3-10 carbon atoms, simple or substituted aryl, or heterocyclic aromatic or heterocyclic radical;

R$_3$, R$_4$, R$_5$, R$_6$, R$_7$, R$_8$, R$_9$, R$_{10}$, R$_{11}$, and R$_{12}$ are each independently H, CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m, n, o, p, q, r, s, t and u are each independently 0 or an integer of from 1 to 5, provided that at least two of l, m, n, o, p, q, r, s, t and u are not zero at any one time; and Z$_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical.

Preferably, the compound of formula (I) is represented by formula (I-L) and, also preferable, R$_1$ is H and R$_2$ is methyl.

In a more preferred embodiment, the present invention provides A method of esterification of maytansinol to give a maytansinoid of the formula 4$_2$:

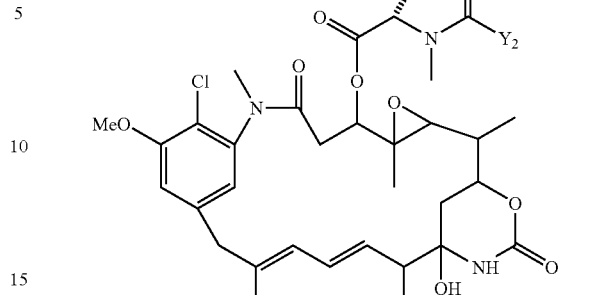

wherein:

Y$_2$ represents (CR$_7$R$_8$)$_l$(CR$_5$R$_6$)$_m$(CR$_3$R$_4$)$_n$CR$_1$R$_2$SZ$_2$, wherein:

R$_1$ and R$_2$ are each independently CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition R$_2$ can be H;

R$_3$, R$_4$, R$_5$, R$_6$, R$_7$ and R$_8$ are each independently H, CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0;

Z$_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical; said method comprising reacting maytansinol of the structure 11 at the C-3:

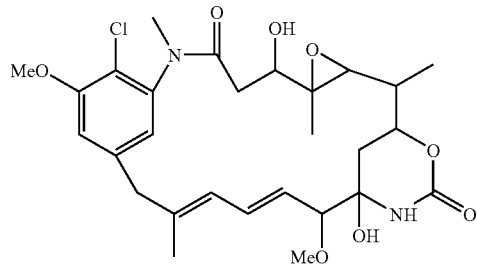

with a compound represented by formula (III-L), (III-D), or (III-D,L):

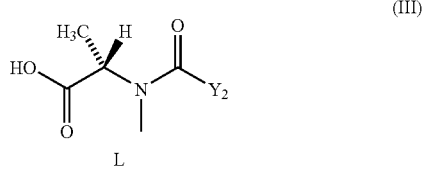

(III)

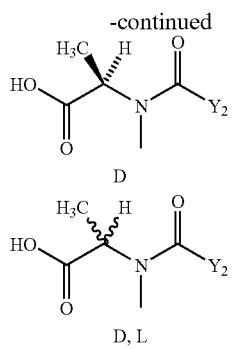

wherein:

Y$_2$ represents (CR$_7$R$_8$)$_l$(CR$_5$R$_6$)$_m$(CR$_3$R$_4$)$_n$CR$_1$R$_2$SZ$_2$, wherein:

R$_1$ and R$_2$ are each independently CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocyclic radical, and in addition R$_2$ can be H;

R$_3$, R$_4$, R$_5$, R$_6$, R$_7$ and R$_8$ are each independently H, CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0; and Z$_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical.

The diastereomers can be separated by HPLC on cyano-bonded silica.

In a more preferred embodiment, the present invention provides a method of esterification of a maytansinoid to produce a maytansinoid ester represented by formula (IV-L), (IV-D), or (IV-D,L):

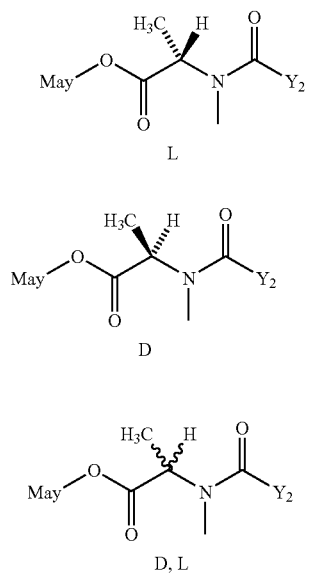

wherein:

Y$_2$ represents (CR$_7$R$_8$)$_l$(CR$_5$R$_6$)$_m$(CR$_3$R$_4$)$_n$CR$_1$R$_2$SZ$_2$, wherein:

R$_1$ and R$_2$ are each independently CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl, or heterocyclic aromatic or heterocyclic radical, and in addition R$_2$ can be H;

R$_3$, R$_4$, R$_5$, R$_6$, R$_7$ and R$_8$ are each independently H, CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0;

Z$_2$ is SR or COR, wherein R is linear alkyl or alkenyl having from 1 to 10 carbon atoms, branched or cyclic alkyl or alkenyl having from 3-10 carbon atoms, or simple or substituted aryl or heterocyclic aromatic or heterocyclic radical; and May is a maytansinoid; said method comprising reacting said may at C-3, C-14 hydroxymethyl, C-15 hydroxy, or C-20 desmethyl, with a compound of formula (III-L), (III-D), or (III-D,L):

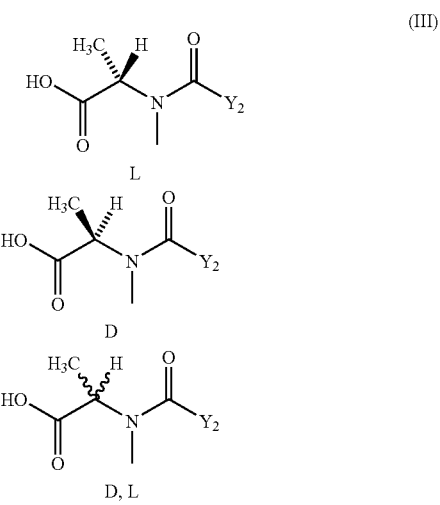

wherein:

Y$_2$ represents (CR$_7$R$_8$)$_l$(CR$_5$R$_6$)$_m$(CR$_3$R$_4$)$_n$CR$_1$R$_2$SZ$_2$, wherein:

R$_1$ and R$_2$ are each independently CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition R$_2$ can be H;

R$_3$, R$_4$, R$_5$, R$_6$, R$_7$ and R$_8$ are each independently H, CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0; and Z$_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical.

In an even more preferred embodiment the present invention provides a method of esterification of maytansinol to give a maytansinoid of the formula $4_2$:

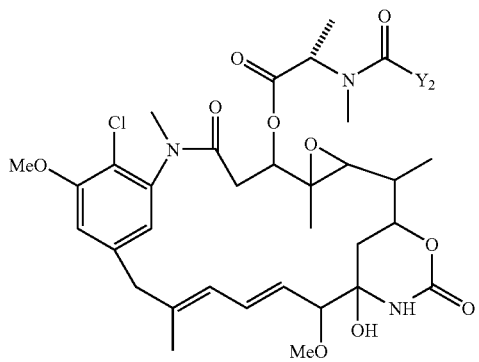

wherein:

$Y_2$ represents $(CR_7R_8)_l(CR_5R_6)_m(CR_3R_4)_nCR_1R_2SZ_2$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0;

$Z_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical, said method comprising reacting maytansinol at the C-3 with a compound of formula (III-L), (III-D), or (III-D, L):

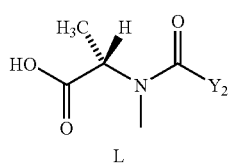

L

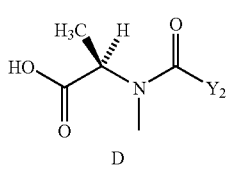

D

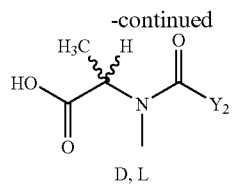

D, L wherein:

$Y_2$ represents $(CR_7R_8)_l(CR_5R_6)_m(CR_3R_4)_nCR_1R_2SZ_2$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0;

$Z_2$ is SR or —COR, wherein R is linear alkyl or alkenyl having from 1 to 10 carbon atoms, branched or cyclic alkyl or alkenyl having from 3 to 10 carbon atoms, or simple or substituted aryl or heterocyclic aromatic or heterocyclic radical.

Preferably, the compound represented by the formula (I) is the L stereoisomer.

For the above methods, it is preferred that $R_1$ is H, $R_2$ is methyl, $R_5$, $R_6$, $R_7$, and $R_8$ are each H, l and m are each 1, and n is 0; or that $R_1$ and $R_2$ are methyl, $R_5$, $R_6$, $R_7$ and $R_8$ are each H, l and m are 1, and n is 0.

When making DM3, the compound of formula (III-L) is 15a(S,S), 15b(S,R) or a mixture of 15a(S,S) and 15b(S,R); the compound of formula (III-D) is N-methyl-D-alanine acylated with the racemic acyl group or with the acyl group having either R or S chirality to give compounds 15; and the compound of formula (III-D,L) is racemic N-methylalanine acylated with a carboxylic group bearing a protected thiol functionality, in which the carbon center bearing the sulfur atom is either racemic or of the R or S chirality to give compounds of the structure of 15.

The mixture of 15a(S,S) and 15b(S,R) can be made by a process comprising:

(1) reacting 4-mercaptopentanoic acid (12) with methyl methanethiolsulfonate to give compound 13;

(2) converting compound 13 into its N-hydroxysuccinimide ester 14;

(3) reacting compound 14 with N-methyl-L-alanine to give said mixture of compounds 15a(S,S) and 15b(S,R).

Similarly, the mixture of compounds 15(R,S) and 15(R,R) can be made by a process comprising:

(1) reacting 4-mercaptopentanoic acid (12) with methyl methanethiolsulfonate to give compound 13;

(2) converting compound 13 into its N-hydroxysuccinimide ester 14;

(3) reacting compound 14 with N-methyl-D-alanine to give said mixture of compounds 15(R,S) and 15(R,R,).

Racemic N-methylalanine acylated with a carboxylic group bearing a protected thiol functionality, in which the carbon center bearing the sulfur atom is either racemic or of R or S chirality to give compounds of the structure 15 can be made by a process comprising:

(1) reacting 4-mercaptopentanoic acid (12) with methyl methanethiolsulfonate to give compound 13;

(2) converting compound 13 into its N-hydroxysuccinimide ester 14;

(3) reacting compound 14 with racemic N-methylalanine to give said racemic N-methylalanine acylated with a carboxylic group bearing a protected thiol functionality, in which the carbon center bearing the sulfur atom is either racemic or of the R or S chirality to give compounds of the structure 15.

The compound 15a(S,S) can be made by a process comprising:

(1) converting (R)-1,3-butanediol into (S)-4-(methydithio)pentanoic acid 19;

(2) converting compound 19 into its N-hydroxysuccinimide ester (20); and (3) reacting compound 20 with N-methyl-L-alanine to give said compound 15a(S,S).

The compound 15b(S,R) can be made by a process comprising:

(1) converting (S)-1,3-butanediol into (R)-4-(methydithio)pentanoic acid 24;

(2) converting compound 24 into its N-hydroxysuccinimide ester (25); and (3) reacting compound 25 with N-methyl-L-alanine to give said compound 15b(S,R).

When making DM4, the compound of formula (III-L) is a compound 10 containing N-methyl-L-alanine; the compound of formula (III-D) is compound 10 containing N-methyl-D-alanine, and the compound of formula (III-D,L) is compound 10 containing racemic N-methylalanine.

The compound 10 containing N-methyl-L-alanine, N-methyl-D-alanine, or racemic N-methylalanine is made by a process comprising:

(1) reacting isobutylene sulfide (5) with the anion of acetonitrile to give compound 6;

(2) hydrolyzing compound 6 to give 4-mercapto-4-methylpentanoic acid (7);

(3) converting compound 7 into disulfide 8 by reaction with methylmethanethiolsulfonate;

(4) converting compound 8 into its N-hydroxysuccinimide ester 9; and (5) reacting compound 9 with N-methyl-L-alanine, N-methyl-D-alanine, or racemic N-methylalanine to give compound 10 containing N-methyl-L-alanine, N-methyl-D-alanine, or racemic N-methylalanine.

According to the present invention, compounds of formula III are also new:

wherein:

$Y_2$ represents $(CR_7R_8)_l(CR_5R_6)_m(CR_3R_4)_nCR_1R_2SZ_2$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0; and $Z_2$ is SR or —COR, wherein R is linear alkyl, branched alkyl or cyclic alkyl having from 1 to 10 carbon atoms, or simple or substituted aryl or heterocyclic aromatic or heterocyclic radical.

The compounds of formula III can be made readily by one of ordinary skill in the art by methods analogous to those disclosed herein for making compounds 10 and 15.

In Vitro Cytotoxicity of Maytansinoids

The in vitro cytotoxicity of maytansinoids of the present invention is shown in FIG. 4. The new maytansinoids (4c, 4e) bearing a hindered disulfide bond are highly potent towards the cell lines tested. Thus 4c kills A-375 cells and SK-Br-3 cells with $IC_{50}$ values of $1.5\times10^{-11}$ M and $7.0\times10^{-12}$ M respectively. Similarly, maytansinoid 4e is also highly potent with $IC_{50}$ values of $3.2\times10^{-11}$ M and $9.0\times10^{-12}$ M towards A-375 and SK-Br-3 cells respectively. Comparison of the in vitro potency of the hindered thiol-containing maytansinoid 4a of the present invention with that of previously described maytansinoid 1 (FIG. 4c,d), indicates that the new maytansinoids are 20 to 50-fold more potent than the previous described ones.

Preparation of Cell-Binding Agents

The effectiveness of the compounds of the invention as therapeutic agents depends on the careful selection of an appropriate cell-binding agent. Cell-binding agents may be of any kind presently known, or that become known and include peptides and non-peptides. Generally, these can be antibodies (especially monoclonal antibodies), lymphokines, hormones, growth factors, vitamins, nutrient-transport molecules (such as transferrin), or any other cell-binding molecule or substance.

More specific examples of cell-binding agents that can be used include:

polyclonal antibodies;

monoclonal antibodies;

fragments of antibodies such as Fab, Fab', and F(ab')$_2$, Fv (Parham, *J. Immunol.* 131:2895-2902 (1983); Spring et al. *J. Immunol.* 113:470-478 (1974); Nisonoff et al. *Arch. Biochem. Biophys.* 89:230-244 (1960));

interferons (e.g. .alpha., .beta., .gamma.);

lymphokines such as IL-2, IL-3, IL-4, IL-6;

hormones such as insulin, TRH (thyrotropin releasing hormone), MSH (melanocyte-stimulating hormone), steroid hormones, such as androgens and estrogens;

growth factors and colony-stimulating factors such as EGF, TGF-alpha, FGF, VEGF, G-CSF, M-CSF and GM-CSF (Burgess, *Immunology Today* 5:155-158 (1984));

transferrin (O'Keefe et al. *J. Biol. Chem.* 260:932-937 (1985)); and vitamins, such as folate.

Monoclonal antibody techniques allow for the production of extremely specific cell-binding agents in the form of specific monoclonal antibodies. Particularly well known in the art are techniques for creating monoclonal antibodies produced by immunizing mice, rats, hamsters or any other mammal with the antigen of interest such as the intact target cell, antigens isolated from the target cell, whole virus, attenuated whole virus, and viral proteins such as viral coat proteins. Sensitized human cells can also be used. Another method of creating monoclonal antibodies is the use of phage libraries of scFv (single chain variable region), specifically human scFv (see e.g., Griffiths et al., U.S. Pat. Nos. 5,885,793 and 5,969, 108; McCafferty et al., WO 92/01047; Liming et al., WO 99/06587). In addition, resurfaced antibodies disclosed in U.S. Pat. No. 5,639,641 may also be used, as may humanized antibodies.

Selection of the appropriate cell-binding agent is a matter of choice that depends upon the particular cell population that is to be targeted, but in general human monoclonal antibodies are preferred if an appropriate one is available.

For example, the monoclonal antibody MY9 is a murine IgG$_1$ antibody that binds specifically to the CD33 Antigen {J. D. Griffin et al 8 Leukemia Res., 521 (1984)} and can be used if the target cells express CD33 as in the disease of acute myelogenous leukemia (AML). Similarly, the monoclonal antibody anti-B4 is a murine IgG$_1$, that binds to the CD19 antigen on B cells {Nadler et al, 131 J. Immunol. 244-250 (1983)} and can be used if the target cells are B cells or diseased cells that express this antigen such as in non-Hodgkin's lymphoma or chronic lymphoblastic leukemia. Similarly, the monoclonal antibody, C242, that binds to the CanAg antigen, (U.S. Pat. No. 5,552,293) can be used to treat CanAg expressing tumors, such us colorectal, pancreatic and gastric cancers.

Additionally, GM-CSF, which binds to myeloid cells can be used as a cell-binding agent to diseased cells from acute myelogenous leukemia. IL-2 which binds to activated T-cells can be used for prevention of transplant graft rejection, for therapy and prevention of graft-versus-host disease, and for treatment of acute T-cell leukemia. MSH, which binds to melanocytes, can be used for the treatment of melanoma. Folic acid can be used to target the folate receptor expressed on ovarian and other tumors. Epidermal growth factor can be used to target squamous cancers such as lung and head and neck. Somatostatin can be used to target neuroblastomas and other tumor types.

Cancers of the breast and testes can be successfully targeted with estrogen (or estrogen analogues) or androgen (or androgen analogues) respectively as cell-binding agents.

Production of Cytotoxic Conjugates

The present invention also provides a maytansinoid-cell-binding agent conjugate comprising at least one maytansinoid linked to the cell-binding agent, wherein the cell-binding agent is linked to the maytansinoid using the thiol or disulfide functionality that is present on the acyl group of an acylated amino acid side chain found at C-3, C-14 hydroxymethyl, C-15 hydroxy or C-20 desmethyl of the maytansinoid, and wherein the acyl group of the acylated amino acid side chain has its thiol or disulfide functionality located at a carbon atom that has one or two substituents, said substituents being CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition one of the substituents can be H, and wherein the acyl group has a linear chain length of at least three carbon atoms between the carbonyl functionality and the sulfur atom.

A preferred cell-binding agent conjugate comprises at least one maytansinoid linked to a cell-binding agent, wherein the maytansinoid is represented by formula 4$_1$':

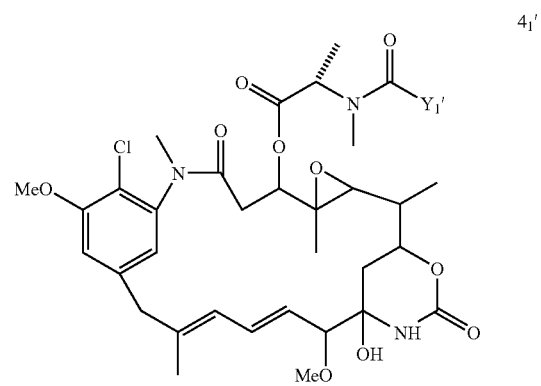

wherein:

Y$_1$' represents (CR$_7$R$_8$)$_l$(CR$_9$═CR$_{10}$)$_p$(C≡C)$_q$A$_o$ (CR$_5$R$_6$)$_m$D$_u$(CR$_{11}$═CR$_{12}$)$_r$(C≡C)$_s$B$_t$(CR$_3$R$_4$)$_n$CR$_1$R$_2$S—, wherein: R$_1$ and R$_2$ are each independently CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical, and in addition R$_2$ can be H;

A, B, and D, each independently is cycloalkyl or cycloalkenyl having 3-10 carbon atoms, simple or substituted aryl, or heterocyclic aromatic or heterocyclic radical;

R$_3$, R$_4$, R$_5$, R$_6$, R$_7$, R$_8$, R$_9$, R$_{10}$, R$_{11}$, and R$_{12}$ are each independently H, CH$_3$, C$_2$H$_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical; and l, m, n, o, p, q, r, s, t and u are each independently 0 or an integer of from 1 to 5, provided that at least two of l, m, n, o, p, q, r, s, t and u are non-not zero at any one time.

Preferably, R$_1$ is H and R$_2$ is methyl. or R$_1$ and R$_2$ are methyl.

An even more preferred cell-binding agent conjugate comprises at least one maytansinoid linked to the cell-binding agent, wherein the maytansinoid is represented by formula (II-L), (II-D), or (II-D,L):

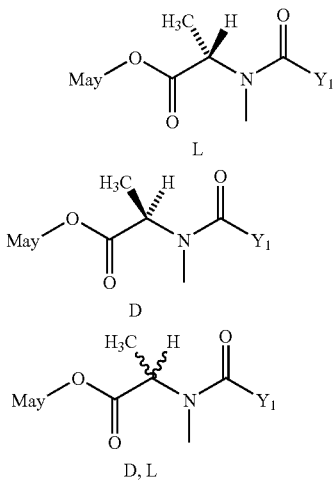

wherein:

$Y_1$ represents $(CR_7R_8)_l(CR_5R_6)_m(CR_3R_4)_nCR_1R_2S-$, wherein:

$R_1$ and $R_2$ are each independently $CH_3$, $C_2H_5$, linear alkyl or alkenyl having from 1 to 10 carbon atoms, branched or cyclic alkyl or alkenyl having from 3 to 10 carbon atoms, phenyl, substituted phenyl, heterocyclic aromatic or heterocyclic radical, and in addition $R_2$ can be H;

$R_3$, $R_4$, $R_5$, $R_6$, $R_7$ and $R_8$ are each independently H, $CH_3$, $C_2H_5$, linear alkyl or alkenyl having from 1 to 10 carbon atoms, branched or cyclic alkyl or alkenyl having from 3 to 10 carbon atoms, phenyl, substituted phenyl or heterocyclic aromatic or heterocyclic radical;

l, m and n are each independently an integer of from 1 to 5, and in addition n can be 0; and May represents a maytansinol which bears the side chain at C-3, C-14 hydroxymethyl, C-15 hydroxy or C-20 desmethyl.

Even more preferred is a maytansinoid-cell-binding agent conjugate, wherein the maytansinoid is represented by formula $4_1$:

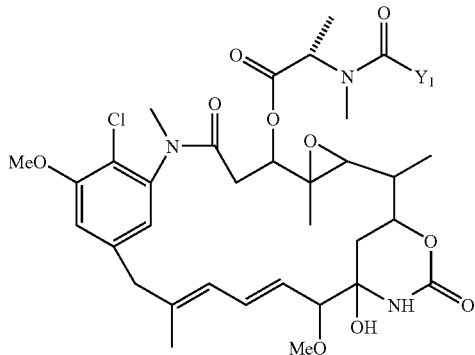

wherein the substituents are as defined for formula (II) above.

Especially preferred are any of the above-described compounds, wherein $R_1$ is H, $R_2$ is methyl, $R_5$, $R_6$, $R_7$ and $R_8$ are each H, l and m are each 1, and n is 0; and those wherein $R_1$ and $R_2$ are methyl, $R_5$, $R_6$, $R_7$, $R_8$ are each H, l and m are 1, and n is 0.

Further, the L-aminoacyl stereoisomer is preferred.

Representational cytotoxic conjugates of the invention are antibody/maytansinoid, antibody fragment/maytansinoid, epidermal growth factor (EGF)/maytansinoid, melanocyte stimulating hormone (MSH)/maytansinoid, thyroid stimulating hormone (TSH)/maytansinoid, somatostatin/maytansinoid, folate/maytansinoid, estrogen/maytansinoid, estrogen analogue/maytansinoid, androgen/maytansinoid, and androgen analogue/maytansinoid.

The thiol-containing maytansinoid is reacted with an appropriately modified cell-binding agent to produce cytotoxic conjugates. These conjugates may be purified by gel-filtration, ion exchange chromatography, or by HPLC.

Schemes for preparing conjugates from sulfhydryl group-containing maytansinoids are shown in FIG. 5. More specifically (FIGS. 5a, b), a solution of an antibody in aqueous buffer may be incubated with a molar excess of an antibody modifying agent such as N-succinimidyl-3-(2-pyridyldithio) propionate (SPDP, 3a) to introduce dithiopyridyl groups (FIG. 5a). or with N-succinimidyl-4-(2-pyridyldithio)butanoate (SPDB, 3b) to introduce dithiopyridyl groups (FIG. 5b). The modified antibody is then reacted with the thiol-containing maytansinoids (such as 4a or 4b) to produce a disulfide-linked antibody-maytansinoid conjugate. The maytansinoid-antibody conjugate may then be purified by gel-filtration.

Alternatively, the antibody may be incubated with a molar excess of an antibody modifying agent such as 2-iminothiolane to introduce sulfhydryl groups. The modified antibody is then reacted with the appropriate disulfide-containing maytansinoids to produce a disulfide-linked antibody-maytansinoid conjugate. The maytansinoid-antibody conjugate may then be purified by gel-filtration.

The number of maytansinoid molecules (denoted with w in FIGS. 5a to 5d) bound per antibody molecule can be determined by measuring spectrophotometrically the ratio of the absorbance at 252 nm and 280 nm. An average of 1-10 maytansinoid molecules/antibody molecule can be linked by this method. The preferred average number of linked maytansinoid molecules per antibody molecule is 2-5, and the most preferred is 3-4.5.

Figure 5A:
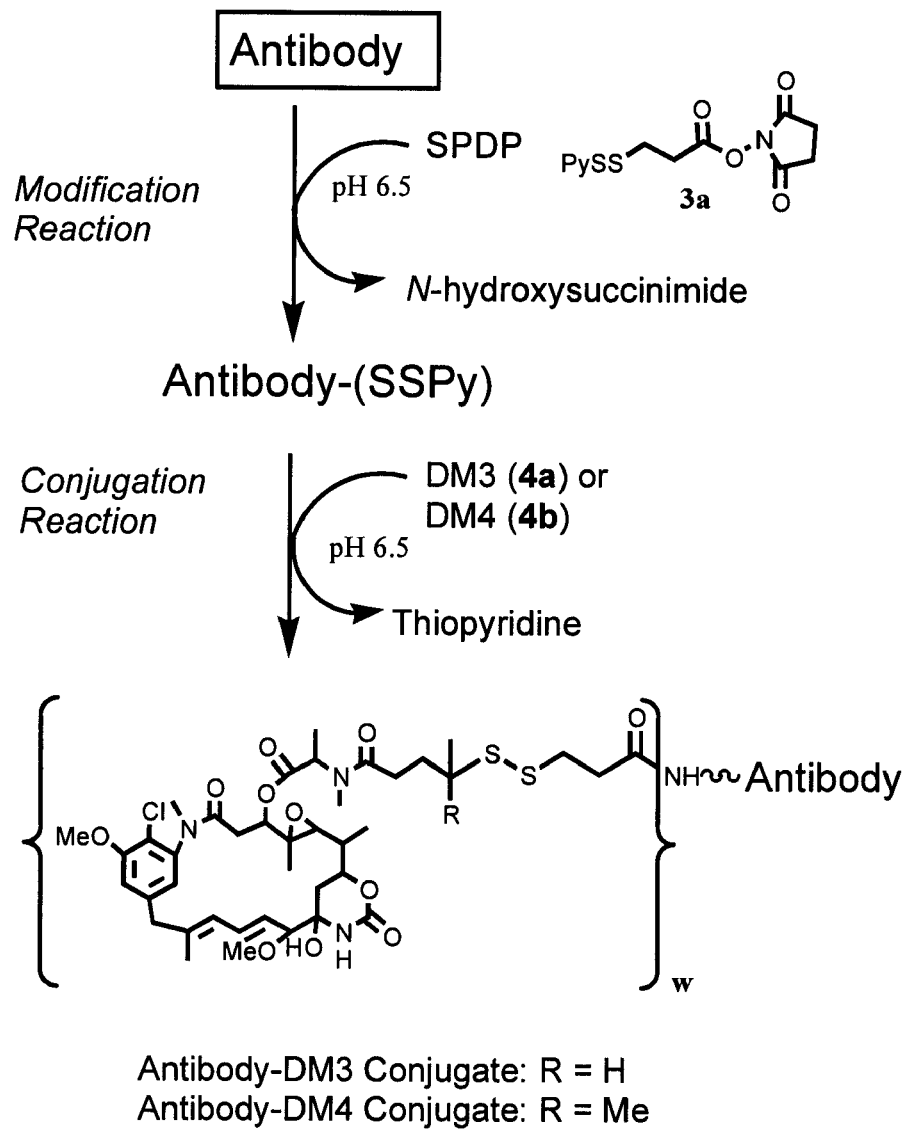
FIGS. 5a-d show schemes for the preparation of conjugates of cell-binding agents with maytansinoids of the present invention.
Figure 5B:
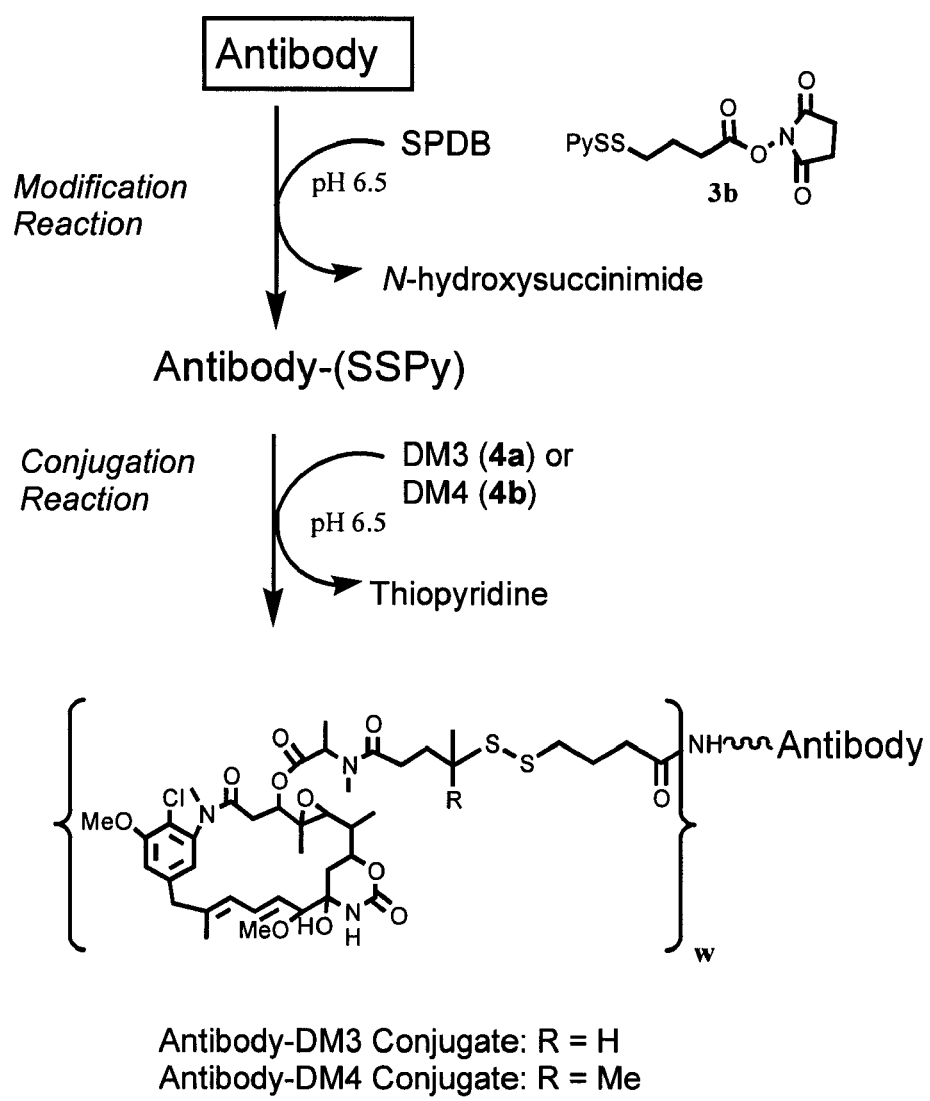
Figure 5C:
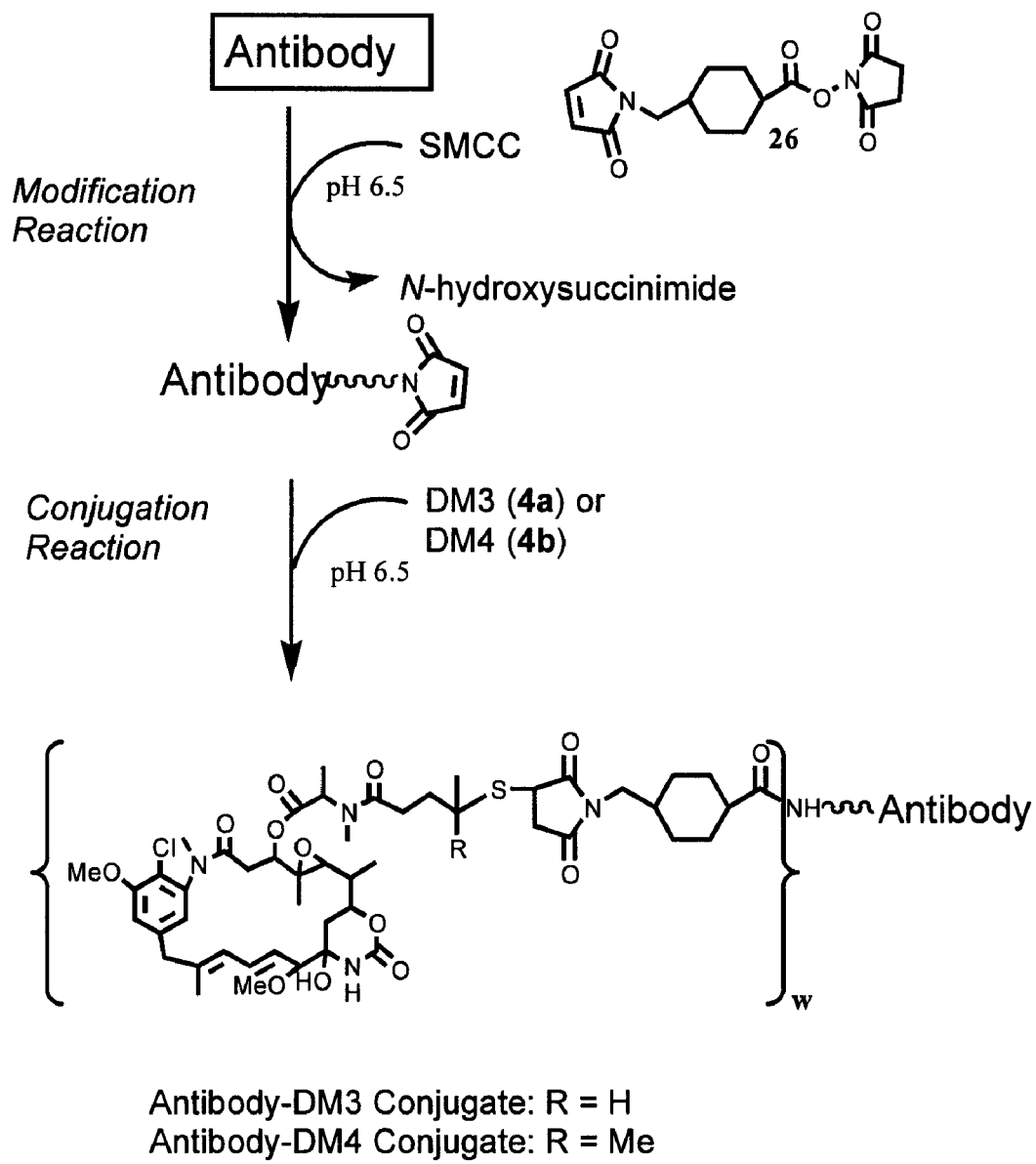
Figure 5D:
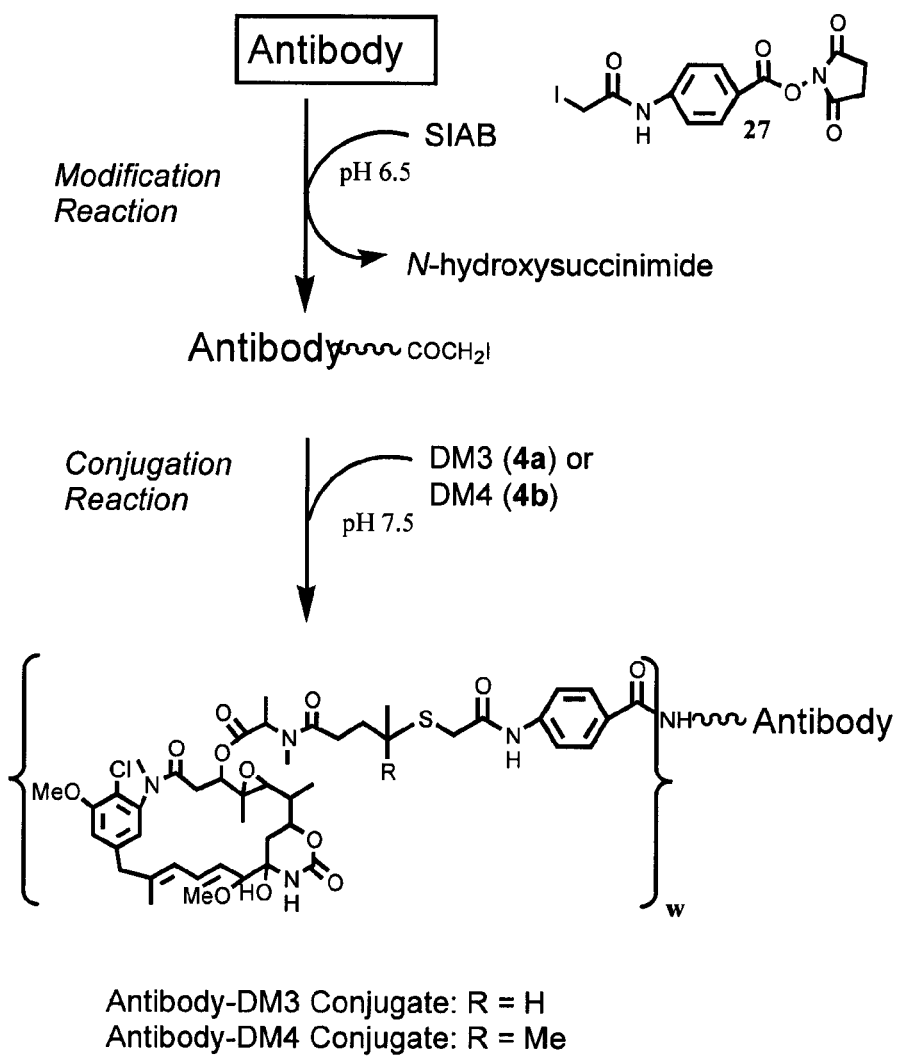

Alternatively, a solution of an antibody in aqueous buffer may be incubated with a molar excess of an antibody-modifying agent such as N-succinimidyl-4-(N-maleimidomethyl)-cyclohexane-1-carboxylate (SMCC, 26) to introduce maleimido groups (FIG. 5c), or with N-succinimidyl-4-(iodoacetyl)-aminobenzoate (SIAB, 27) to introduce iodoacetyl groups (FIG. 5d). The modified antibody is then reacted with the thiol-containing maytansinoids (such as 4a or 4b) to produce a thioether-linked antibody-maytansinoid conjugate. The maytansinoid-antibody conjugate may then be purified by gel-filtration.

The number of maytansinoid molecules bound per antibody molecule can be determined by spectrophotometric analysis as described above.

Thus, the present invention provides a method of making a maytansinoid-cell-binding agent conjugate comprising making a purified maytansinoid by one of the methods described above, and reacting the purified maytansinoid with a cell-binding agent comprising a reactive dithio or a sulfhydryl group. Preferably, the reactive dithio group is a dithiopyridyl group or a substituted dithiopyridyl group. Especially preferably, the reactive dithio group comprises a nitropyridyldithio or dinitropyridyldithio group.

In another method, the purified maytansinoid is reacted with a cell-binding agent comprising a maleimido group or a haloacetyl group.

Conjugates of cell-binding agents with maytansinoid drugs of the invention can be evaluated for their ability to suppress proliferation of various unwanted cell lines in vitro (FIG. 6). For example, cell lines such as the human colon carcinoma line COLO 205, the human melanoma cell line A-375, the human myeloid leukemia cell line HL60 can be used for the assessment of cytotoxicity of these conjugates. Cells to be evaluated can be exposed to the compounds for 24 hours and the surviving fractions of cells measured in direct assays by known methods. $IC_{50}$ values can then be calculated from the results of the assays.

The in vitro potency and target specificity of antibody-maytansinoid conjugates of the present invention are shown in FIGS. 6, 10 and 12. Thus, FIG. 6 shows that both huC242-DM3 and huC242-DM4 are highly potent in killing antigen positive COLO 205 cells, with $IC_{50}$ values of $1.3 \times 10^{-11}$ M and $1.1 \times 10^{-11}$ M respectively. In contrast, antigen negative A-375 cells are about 500-fold less sensitive demonstrating that maytansinoid conjugates of the present invention are highly potent and specific. Similarly, FIGS. 10 and 12 demonstrate the high potency and target specificity of conjugates of the maytansinoids of the present invention, with the antibodies MY9-6 and anti-B4 respectively.

The in vivo anti-tumor efficacy of conjugates of antibodies with the hindered thiol-containing maytansinoids of the present invention was compared with that of previously described maytansinoid conjugates in several different human tumor models in mice. In the first model (FIG. 7), SCID mice bearing established subcutaneous human colon tumor HT-29 xenografts were treated either with the antibody conjugate (huC242-DM1) of the previously described maytansinoid DM1, or with the two new maytansinoid conjugates (huC242-DM3, huC242-DM4). Treatment with huC242-DM1 resulted in a tumor growth delay of 18 days. In contrast, the new agents were significantly more efficacious, with tumor growth delays of 28 days for huC242-DM3 and 36 days for huC242-DM4.

In the second model (FIG. 8), mice bearing established subcutaneous human colon tumor COLO 205 xenografts were treated either with the antibody conjugate (huC242-DM1) of the previously described maytansinoid DM1, or with the two new maytansinoid conjugates (huC242-DM3, huC242-DM4). Treatment with huC242-DM1 did not result in tumor regression and gave a tumor growth delay of 20 days. In contrast, the new agents were significantly more efficacious. Complete tumor regression lasting 45 days was achieved in the group treated with huC242-DM3, huC242-DM4 was even more efficacious resulting in cures of all the treated mice.

In the third model (FIG. 9), mice bearing established subcutaneous human myeloid leukemia HL60 xenografts were treated either with the antibody conjugate (MY-9-6-DM1) of the previously described maytansinoid DM1, or with the two new maytansinoid conjugates (MY9-6-DM3, MY9-6-DM4). Treatment with MY9-6-DM1 did not result in tumor regression and gave a tumor growth delay of 5 days. In contrast, the new agents were significantly more efficacious. Resulting in tumor regression. Both MY-9-6-DM3 and MY-9-6-DM4 gave tumor growth delays of greater than 20 days.

In the fourth model (FIG. 11), a maytansinoid of the present invention (huMY9-6-DM4) was directly compared with that of a conjugate of the previously described maytansinoid (huMY9-6-DM1) in a subcutaneous xenograft model, established with HL-60 cells. At an equivalent dose, treatment with the conjugate of the current invention, MY9-6-DM4, results complete tumor regression lasting 85 days. In contrast, the conjugate of the previously described maytansinoid is much less active with a tumor growth delay of only about 48 days.

In the fifth model (FIG. 13a), a conjugate of a maytansinoid of the present invention with the huB4 antibody shows high anti-tumor activity in a dose-dependent manner in a subcutaneous Ramos tumor model. Complete tumor regressions and cures are achieved at doses that are non-toxic (FIG. 13a,b).

Results from the above five efficacy experiments demonstrate that the sterically hindered thiol-containing maytansinoids of the present invention give cell-binding agent conjugates with vastly improved anti-tumor activity compared to the previously described maytansinoid-cell-binding agent conjugates.

Compositions and Methods of Use

The present invention provides pharmaceutical compositions comprising an effective amount of any of the maytansinoid-cell-binding agents of the present invention, pharmaceutically acceptable a salt or solvate thereof, and a pharmaceutically acceptable carrier, diluent or excipient.

The present invention also provides methods of treatment comprising administering to a subject in need of treatment an effective amount of any of the conjugates described above.

Similarly, the present invention provides a method for inducing cell death in selected cell populations comprising contacting target cells or tissue containing target cells with an effective amount of a cytotoxic agent comprising any of the maytansinoid-cell-binding agents of the present invention, a salt or solvate thereof. The target cells are cells to which the cell-binding agent can bind.

If desired, other active agents, such as other anti-tumor agents, may be administered along with the conjugate.

Suitable pharmaceutically acceptable carriers, diluents, and excipients are well known and can be determined by those of ordinary skill in the art as the clinical situation warrants.

Examples of suitable carriers, diluents and/or excipients include: (1) Dulbecco's phosphate buffered saline, pH about 7.4, containing or not containing about 1 mg/ml to 25 mg/ml human serum albumin, (2) 0.9% saline (0.9% w/v NaCl), and (3) 5% (w/v) dextrose; and may also contain an antioxidant such as tryptamine and a stabilizing agent such as Tween 20.

The method for inducing cell death in selected cell populations can be practiced in vitro, in vivo, or ex vivo.

Examples of in vitro uses include treatments of autologous bone marrow prior to their transplant into the same patient in order to kill diseased or malignant cells: treatments of bone marrow prior to their transplantation in order to kill competent T cells and prevent graft-versus-host-disease (GVHD); treatments of cell cultures in order to kill all cells except for desired variants that do not express the target antigen; or to kill variants that express undesired antigen.

The conditions of non-clinical in vitro use are readily determined by one of ordinary skill in the art.

Examples of clinical ex vivo use are to remove tumor cells or lymphoid cells from bone marrow prior to autologous transplantation in cancer treatment or in treatment of autoimmune disease, or to remove T cells and other lymphoid cells from autologous or allogenic bone marrow or tissue prior to transplant in order to prevent GVHD. Treatment can be carried out as follows. Bone marrow is harvested from the patient or other individual and then incubated in medium containing serum to which is added the cytotoxic agent of the invention, concentrations range from about 10 μM to 1 pM, for about 30 minutes to about 48 hours at about 37° C. The exact conditions of concentration and time of incubation, i.e., the dose, are readily determined by one of ordinary skill in the art. After incubation the bone marrow cells are washed with medium containing serum and returned to the patient intravenously according to known methods. In circumstances where the patient receives other treatment such as a course of ablative chemotherapy or total-body irradiation between the time of harvest of the marrow and reinfusion of the treated cells, the treated marrow cells are stored frozen in liquid nitrogen using standard medical equipment.

For clinical in vivo use, the cytotoxic agent of the invention will be supplied as a solution or a lyophilized powder that are tested for sterility and for endotoxin levels. Examples of suitable protocols of conjugate administration are as follows. Conjugates are given weekly for 4 weeks as an intravenous bolus each week. Bolus doses are given in 50 to 1000 ml of normal saline to which 5 to 10 ml of human serum albumin can be added. Dosages will be 10 μg to 2000 mg per administration, intravenously (range of 100 ng to 20 mg/kg per day). After four weeks of treatment, the patient can continue to receive treatment on a weekly basis. Specific clinical protocols with regard to route of administration, excipients, diluents, dosages, times, etc., can be determined by one of ordinary skill in the art as the clinical situation warrants.

Examples of medical conditions that can be treated according to the in vivo or ex vivo methods of inducing cell death in selected cell populations include malignancy of any type including, for example, cancer of the lung, breast, colon, prostate, kidney, pancreas, ovary, and lymphatic organs; autoimmune diseases, such as systemic lupus, rheumatoid arthritis, and multiple sclerosis; graft rejections, such as renal transplant rejection, liver transplant rejection, lung transplant rejection, cardiac transplant rejection, and bone marrow transplant rejection; graft versus host disease; viral infections, such as CMV infection, HIV infection, AIDS, etc.; and parasite infections, such as giardiasis, amoebiasis, schistosomiasis, and others as determined by one of ordinary skill in the art.

EXAMPLES

The invention will now be illustrated by reference to non-limiting examples. Unless otherwise stated, all percents, ratios, parts, etc. are by weight. The examples described below are for compounds where $R_1$ is $CH_3$, $R_2$ is H, $R_5$, $R_6$, $R_7$, $R_8$ are each H, l and m are each 1, and n is 0. Similar synthesis can be carried out for other compounds of the invention where $R_1$ and $R_2$ are each independently H, $CH_3$, $C_2H_5$, or higher alkyl, alkenyl, having from 1 to 10 carbon atoms, or phenyl, substituted phenyl or heterocyclic aromatic or heterocyclic radical; and where l, m and n are each integers from 1 to 5, and in addition, n can also be 0.

All reagents were purchased from the Aldrich Chemical Co., New Jersey, or other commercial sources. Maytansinol (11) was prepared as described previously (U.S. Pat. No. 6,333,410). Nuclear Magnetic Resonance ($^1$H NMR) spectra were acquired on a Bruker 400 MHz instrument and mass spectra were acquired on a Bruker Daltonics Esquire 3000 instrument using electrospray ionization.

Example 1

Synthesis of Maytansinoid 4b

4-Mercapto-4-methylpentanoic acid (7): A 500 mL flask was equipped with a stir bar and a 150 mL addition funnel. The system was placed under an argon atmosphere. 150 mL of anhydrous tetrahydrofurane (THF) and 75 mL of 2.5 M n-BuLi in hexanes (18.7 mmol) were added via a cannula and the solution was cooled in a −78° C. dry ice/acetone bath. Acetonitrile (7.3 g, 9.4 mL, 18 mmol) was added drop-wise via a syringe over approximately 5 min. The reaction was stirred for 30 min, while white lithium-acetonitrile precipitate was formed. Isobutylene sulfide (15 g, 17 mmol) was dissolved in 100 mL of anhydrous THF and added drop wise over approximately 30 min via the addition funnel. The cooling bath was removed and the reaction was allowed to stir for 3 hours. The flask was cooled in an ice/water bath as 38 mL of 0.5 M HCl was added drop-wise. The THF layer was retained and the aqueous layer was washed twice with 75 mL of ethyl acetate. The THF and ethyl acetate layers were combined, dried over approximately 20 g of anhydrous sodium sulfate and transferred to a 250 mL flask. Solvent was removed by rotary evaporation under vacuum to give crude 6. Ethanol (30 mL) and a stir bar were added. The contents were stirred as a solution of 8.0 g NaOH in 30 mL deionized water was slowly added. The flask was equipped with a reflux condenser and placed under an argon atmosphere. The reaction was refluxed overnight then cooled to room temperature. Deionized water (60 mL) was added and the mixture was extracted twice with 25 mL portions of a 2:1 mixture of ethyl acetate and hexane. The aqueous layer was acidified to pH 2 with concentrated HCl then extracted three times with 75 mL portions of ethyl acetate. The organic layers were dried over anhydrous $Na_2SO_4$ and solvent was removed by rotary evaporation under vacuum to give 10 g of product 7 (39% yield). Material was used without further purification. $^1$H NMR ($CDCl_3$): δ1.38 (6H, s), 1.87-1.93 (2H, m), 2.08 (1H, s), 2.51-2.57 (2H, m).

4-Methyl-4-(methyldithio)pentanoic acid (8): A solution of mercaptopentanoic acid 7 (6.0 mL, 40 mmol) was dissolved in 50 mL of deionized water in a 250 mL flask. The solution was magnetically stirred as sodium carbonate (6.4 g, 60 mmol) was added to the acid at a rate that would not cause excessive frothing. The flask was equipped with a 100 mL addition funnel, which was charged with a solution of methyl methanethiolsulfonate (7.5 g, 60 mmol) dissolved in 30 mL of glass-distilled 100% ethanol. The flask was cooled in an ice/water bath and the system was maintained under an argon atmosphere. The methyl methanethiolsulfonate solution was added drop-wise to the flask as rapidly as possible but without causing excessive frothing. The cooling bath was removed and the reaction mixture was allowed to stir for an additional 3 hours. Solvent was removed by rotary evaporation under vacuum, until approximately 20 mL remained. After which 10 mL of saturated sodium bicarbonate and 30 mL of deionized water were added. The mixture was washed three times with 25 mL portions of ethyl acetate in a separatory funnel. The aqueous layer was adjusted to approximately pH 2 with 5 M HCl and was extracted twice with 120 mL portions of ethyl acetate. The organic layers were combined and washed with 20 mL of a solution composed of saturated NaCl and 1M HCl at a ratio of 4:1. The organic layer was then dried over 14 g of anhydrous sodium sulfate and solvent was removed by rotary evaporation under vacuum to give 5.4 g of product 8 (70% yield). The material can be taken to the next step without further purification. $^1$H NMR ($CDCl_3$): δ1.54 (6H, s), 2.15-2.21 (2H, m), 2.64 (3H, s), 2.69-2.72 (2H, m). MS (M+Na$^+$) calc.: 217.0, found: 217.1.

N-Hydroxysuccinimidyl 4-methyl-4-(methyldithio)pentanoate (9): Methyldithiopentanoic acid 8 (3.0 g, 15 mmol) was dissolved in 20 mL of methylene chloride and stirred magnetically as N-hydroxysuccinimide (2.65 g, 23 mmol) was added followed by 1-[3-(dimethylamino)propyl]-3-ethylcarbodiimide hydrochloride (EDC, 4.4 g, 23 mmol). The mixture was stirred under an argon atmosphere for 2 hours.

The reaction mixture was poured into a 125 mL separatory funnel, 40 mL of ethyl acetate was added and the solution was washed twice with 20 mL portions of 50 mM potassium phosphate buffer, pH 6.0, and once with 12 mL of saturated sodium chloride. The organic layer was dried over 14 g of anhydrous $Na_2SO_4$ and solvent was removed by rotary evaporation under vacuum to give 4.0 g of product 9 (90% yield), which was used without further purification. $^1$H NMR ($CDCl_3$): δ1.30 (6H, s), 2.00-2.05 (2H, m), 2.39 (3H, s), 2.68-2.72 (2H, m), 2.73-2.83 (4H, m). MS ($M+Na^+$) calc.: 314.0, found: 314.1.

N-methyl-N-(4-methyl-4-methyldithio-1-oxopentyl)-L-alanine (10): N-Methyl-L-alanine (2.85 g, 18.0 mmol) was dissolved in 50 mL of a 1:1 solution of dimethoxyethane and deionized water in a 125 mL flask equipped with a magnetic stir bar. Triethylamine (6.9 g, 36 mmol) was added and the solution was vigorously stirred as 9 (5.44 g, 18 mmol) dissolved in 40 mL of the same solvent mixture was added drop-wise over approximately 5 min. After 2 hours the reaction mixture was concentrated to approximately 40 mL by rotary evaporation under vacuum, then 10 mL of deionized water and 1 M HCl were added to give a pH of approximately 2. The mixture was poured into a separatory funnel and extracted twice with 50 mL portions of ethyl acetate. The organic layers were combined and then washed with 7 mL of saturated sodium chloride solution. The organic layer was dried over 8.0 g of anhydrous $Na_2SO_4$ and the solvent was removed by rotary evaporation under vacuum. The residue was taken up in a minimum volume of ethyl acetate and purified by chromatography on silica (silica: 40 micron flash grade, silica bed: 24×3.0 cm, mobile phase: hexanes:ethyl acetate:acetic acid 50:48:2). Fractions containing desired product were combined and solvent was removed under vacuum. Residual acetic acid was removed by dissolving the residue in a minimum volume of ethyl acetate and precipitating product by the rapid but drop-wise addition of hexane with stirring. Hexane was added until product was no longer detected in the supernatant by TLC analysis. The precipitate was vacuum dried for 4 hours to give 2.2 g of product 10 (51% yield). $^1$H NMR ($CDCl_3$): δ1.32 (6H, s), 1.42 (3H, d, J=7 Hz), 1.90-97 (2H, m), 2.40 (3H, s), 2.42-2.49 (2H, m), 2.9 (3H, s), 5.15 (1H, q, J=7 Hz). MS ($M+Na^+$) calc.: 302.1, found: 302.0.

$N^{2'}$-deacetyl-$N^{2'}$-(4-methyl-4-methyldithio-1-oxopentyl) maytansine (L-DM4-SMe, 4e). A solution of maytansinol (11, 25 mg, 0.44 mmol) and N-methyl-N-(4-methyl-4-methyldithio-1-oxopentyl)-L-alanine (10, 42.0 mg, 0.177 mmol) in 3 mL dichloromethane was magnetically stirred under an argon atmosphere as a solution of dicyclohexylcarbodiimide (DCC, 57.1 mg, 0.277 mmol) in 0.67 mL dichloromethane was added. After 1 min a solution of 1 M $ZnCl_2$ in diethyl ether (0.03 mL, 0.03 mmol) was added. The mixture was stirred at room temperature for 2 hours then 5 mL of ethyl acetate was added and the mixture was vacuum filtered through course filter paper. The filtrate was washed with 2 mL of saturated sodium bicarbonate solution followed by 1 mL of saturated sodium chloride solution. The organic layer was dried over 2 g of anhydrous sodium sulfate. And solvent was removed under vacuum and the residue was purified by silica chromatography using a mixture of dichloromethane and methanol to remove unreacted maytansinol. Fractions containing desired product were combined and solvent was removed under vacuum to give a mixture of diastereomers 4e and 4f. The residue was taken up in a minimum volume of ethyl acetate and purified on a 50 cm by 250 cm, 10 micron Diazem™ CN column using as mobile phase a mixture of hexane, 2-propanol and ethyl acetate at a ratio of 68:8:24. The flow rate was 118 mL/min. Under these conditions the desired product 4e eluted with a retention time of 11 min and the undesired diastereomer 4f had a retention time of 19 min. Fractions containing desired product were combined and solvent was removed under vacuum to give 12.0 mg of product 4e (36% yield). $^1$H NMR ($CDCl_3$): δ0.80 (3H, s), 1.28-1.36 (13H, m), 1.42-1.46 (2H, m), 1.53-1.63 (2H, m), 1.64 (3H, s), 1.75-1.85 (1H, m), 1.90-2.10 (1H, m), 2.18 (1H, dd, J=3 Hz and 14 Hz), 2.31 (3H, s), 2.40-2.49 (1H, m), 2.50-2.65 (1H, m), 2.85 (3H, s), 3.04 (1H, d, J=9 Hz), 3.11 (1H, d, J=11 Hz), 3.23 (3H, s), 3.35 (3H, s), 3.49 (1H, d, J=9 Hz), 3.63 (1H, d, J=12 Hz), 3.98 (3H, s), 4.27 (1H, t, J=10 Hz), 4.79 (1H, dd, J=3 Hz and 12 Hz), 5.41 (1H, q, J=7 Hz), 5.66 (1H, dd J=9 Hz and 15 Hz), 6.21 (1H, s), 6.42 (1H, dd, J=11 Hz and 15 Hz), 6.65 (1H, d, J=1.5 Hz), 6.73 (1H, d, J=11 Hz), 6.81 (1H, d, J=1.5 Hz). High resolution MS ($M+H^+$) calc.: 826.3174, found: 826.3150.

$N^{2'}$-deacetyl-$N^{2'}$-(4-mercapto-4-methyl-1-oxopentyl) maytansine (L-DM4, 4b). The disulfide 4e from above (12 mg, 0.015 mmol) was dissolved in 1.0 mL of 1:1 ethyl acetate: methanol. A solution of dithiothreitol (18 mg, 0.117 mmol) in 0.50 mL of 50 mM phosphate buffer, pH 7.5, was then added. The solution was magnetically stirred under an argon atmosphere for 3 hours, then 1 mL of 200 mM phosphate buffer, pH 6.0, was added and the mixture was extracted three times with 2 mL portions of ethyl acetate. The organic layers were combined and washed with 1 mL of saturated sodium chloride solution, then dried over 1 g of anhydrous sodium sulfate. The solvent was removed under vacuum and the residue was taken up in a minimum of ethyl acetate and purified on a 50 cm×250 cm, 10 micron Diazem™ CN column using as mobile phase a mixture of hexane, 2-propanol and ethyl acetate at a ratio of 70:8:22. The flow rate was 22 mL/min. The desired product 4b eluted with a retention time of 10 min. Fractions containing pure 4b were combined and the solvent was removed under vacuum to give 11 mg of 4b (97% yield). $^1$H NMR ($CDCl_3$): δ0.80 (3H, s), 1.19-1.23 (1H, m), 1.28-1.36 (12H, m), 1.42-1.46 (2H, m), 1.53-1.63 (2H, m), 1.64 (3H, s), 1.75-1.85 (1H, m), 1.90-2.10 (1H, m), 2.18 (1H, dd, J=3 Hz and 14 Hz), 2.40-2.49 (1H, m), 2.50-2.65 (2H, m), 2.88 (3H, s), 3.04 (1H, d, J=9 Hz), 3.11 (1H, d, J=11 Hz), 3.23 (3H, s), 3.35 (3H, s), 3.49 (1H, d, J=9 Hz), 3.63 (1H, d, J=12 Hz), 3.98 (3H, s), 4.27 (1H, t, J=10 Hz), 4.79 (1H, dd, J=3 Hz and 12 Hz), 5.41 (1H, q, J=7 Hz), 5.66 (1H, dd J=9 Hz and 15 Hz), 6.21 (1H, s), 6.42 (1H, dd, J=11 Hz and 15 Hz), 6.65 (1H, d, J=1.5 Hz), 6.73 (1H, d, J=11 Hz), 6.81 (1H, d, J=1.5 Hz). High resolution MS ($M+Na^+$) calc.: 802.3101, found: 802.3116.

Example 2

Synthesis of Maytansinoid 4a

4-Methyldithio-pentanoic acid (13): A solution of 4-mercaptopentanoic acid (12, 16.6 g, 124 mmol) was dissolved in 350 mL of deionized water in a 500 mL flask. The solution was magnetically stirred as sodium carbonate (19.7 g, 186 mmol) was added to the acid at a rate that would not cause excessive frothing. The flask was equipped with a 250 mL addition funnel, which was charged with a solution of methyl methanethiolsulfonate (23.4 g, 186 mmol) dissolved in 220 mL of glass-distilled 100% ethanol. The flask was cooled in an ice/water bath and the system was maintained under an argon atmosphere. The methyl methanethiolsulfonate solution was added drop-wise to the flask as rapidly as possible but at such a speed as to prevent excessive frothing. The cooling bath was removed and the reaction mixture was allowed to stir for an additional 2 hours. Solvent was removed by rotary evaporation under vacuum, until approximately 250 mL remained. After which 30 mL of saturated sodium bicarbonate solution and 50 mL of deionized water were added. The mixture was washed three times with 200 mL portions of ethyl acetate in a separatory funnel. The aqueous layer was adjusted to approximately pH 2 with 5 M HCl and was extracted twice with 400 mL portions of ethyl acetate. The organic layers were combined, then washed with 60 mL of a 4:1 mixture of saturated NaCl solution and 1M HCl, then dried over 50 g of anhydrous sodium sulfate, and finally, the solvent was removed by rotary evaporation under vacuum to give 10.2 g of product 13 (45% yield). The material was used in the next reaction without further purification. $H^1$ NMR δ1.36 (3H, d, J=7 Hz), 1.84-1.95 (H, m), 1.85-2.56 (1H, m), 2.42 (3H, s), 2.53 (2H, t, J=7 Hz), 2.85-2.95 (1H, m), MS (M+Na$^+$) calc.: 203.3, found: 203.2.

N-Hydroxysuccinimidyl 4-methyldithio-pentanoate (14): 4-methyldithio-pentanoic acid (13, 0.75 g, 4.16 mmol) was dissolved in 7.0 mL of methylene chloride and stirred magnetically while N-hydroxysuccinimide (0.526 g, 4.57 mmol) was added followed by 1-[3-(dimethylamino)propyl]-3-ethylcarbodiimide hydrochloride (0.877 g, 4.57 mmol). The mixture was stirred under an argon atmosphere for 2.5 hours, then poured into a 60 mL separatory funnel containing 20 mL of ethyl acetate. The resulting solution was washed twice with 15 mL portions of 50 mM potassium phosphate buffer, pH 6.0, and once with 5 mL of saturated sodium chloride. The organic layer was dried over 8 g of anhydrous $Na_2SO_4$ and the solvent was removed by rotary evaporation under vacuum to give 1.15 g of product 14 (87% yield), which was used for the next reaction without further purification. $H^1$ NMR δ1.48 (3H, d, J=7), 2.06 (1H, m), 2.17 (1H, m), 2.55 (3H, s), 2.93 (2H, t, J=7), 2.98 (4H, s), 3.15 (1H, m). MS (M+Na$^+$) calc.: 304.1, found: 304.0.

N-methyl-N-(4-methyldithio-1-oxopentyl)-L-alanine (15): N-Methyl-L-alanine (0.64 g, 6.2 mmol) was dissolved in 8 mL of a 1:1 mixture of dimethoxyethane and deionized water in a 125 mL flask equipped with a magnetic stir bar. Triethylamine (0.841 g, 8.3 mmol) was added and the flask was vigorously stirred as a solution of 14 (1.0 g, 3.6 mmol) in 8 mL of the same solvent mixture was added drop-wise over approximately 5 min. After 2 hours, the reaction mixture was concentrated to approximately 3 mL by rotary evaporation under vacuum, then 15 mL of deionized water and 1 M HCl were added to give a pH of approximately 2. The mixture was poured into a 60 mL separatory funnel and extracted twice with 15 mL portions of ethyl acetate. The organic layers were combined, washed with 3 mL of saturated sodium chloride solution, then dried over 8.0 g of anhydrous $Na_2SO_4$, and finally, the solvent was removed by rotary evaporation under vacuum. The residue was taken up in a minimum volume of ethyl acetate and purified by silica chromatography (silica: 40 micron flash grade, silica bed 24×3.0 cm, mobile phase hexanes:ethyl acetate:acetic acid 50:48:2). Fractions containing desired product 15 were combined and the solvent was removed under vacuum. Residual acetic acid was removed by dissolving the residue in a minimum volume of ethyl acetate and precipitating product by the rapid but drop-wise addition of hexane with stirring. Hexane was added until product was no longer detected in the supernatant by TLC analysis. The precipitate was vacuum dried to give 0.60 g of product 15 (62% yield). $H^1$ NMR δ1.35 (3H, d, J=7), 1.41 (3H, d, J=7), 1.94-2.03 (2H, m), 2.43 (3H, s), 2.50-2.55 (2H, m), 2.83-2.93 (1H, m), 2.98 (3H, s), 5.14 (1H, q, J=7). MS (M+Na$^+$) calc.: 288.1, found: 288.1.

$N^{2'}$-deacetyl-$N^{2'}$-(4-methyldithio-1-oxopentyl)maytansine (L-DM3-SMe, 4c): A solution of Maytansinol (25 mg, 0.44 mmol) and 15 (42.0, 0.177 mmol) in 3 mL dichloromethane was magnetically stirred under an argon atmosphere as a solution of dicyclohexylcarbodiimide (DCC, 57.1 mg, 0.277 mmol) in 0.67 mL dichloromethane was added. After 1 min, a solution of 1 M $ZnCl_2$ in diethyl ether (0.03 mL, 0.03 mmol) was added. The mixture was stirred at room temperature for 2 hours, then 5 mL of ethyl acetate was added and the mixture was vacuum filtered through course filter paper. The filtrate was washed with 2 mL of saturated sodium bicarbonate solution followed by 1 mL of saturated sodium chloride solution. The organic layer was dried over 2 g of anhydrous sodium sulfate, then the solvent was removed under vacuum. The residue was purified by silica chromatography using a mixture of dichloromethane and methanol to remove unreacted maytansinol. Fractions containing desired product were combined and solvent was removed under vacuum to give a mixture of the diastereomers 4c and 4d. The residue was taken up in a minimum volume of ethyl acetate and purified on a 50 cm by 250 cm, 10 micron Diazem™ CN column using as mobile phase a 68:8:24 mixture of hexane, 2-propanol and ethyl acetate. The flow rate was 118 mL/min. The desired product 4c eluted with a retention time of 11 min, the undesired diastereomer 4d had a retention time of 19 min. Fractions containing the desired product were combined and stripped of the solvent under vacuum to give 12.0 mg of product 4c (36% yield). $^1$H NMR (CDCl$_3$): δ0.80 (3H, s), 1.19-1.23 (1H, m), 1.28-1.36 (9H, m), 1.42-1.46 (1H, m), 1.53-1.63 (2H, m), 1.64 (3H, s), 1.80-1.89 (1H, m), 1.90-2.09 (1H, m), 2.18 (1H, dd, J=3 Hz and 14 Hz), 2.32 (3H, s), 2.33-2.42 (1H, m), 2.49-2.62 (2H, m), 2.88 (3H, s), 3.04 (1H, d, J=9 Hz), 3.11 (1H, d, J=11 Hz), 3.23 (3H, s), 3.35 (3H, s), 3.49 (1H, d, J=9 Hz), 3.63 (1H, d, J=12 Hz), 3.98 (3H, s), 4.27 (1H, t, J=10 Hz), 4.79 (1H, dd, J=3 Hz and 12 Hz), 5.41 (1H, q, J=7 Hz), 5.66 (1H, dd J=9 Hz and 15 Hz), 6.21 (1H, s), 6.42 (1H, dd, J=11 Hz and 15 Hz), 6.65 (1H, d, J=1.5 Hz), 6.73 (1H, d, J=11 Hz), 6.81 (1H, d, J=1.5 Hz). MS (M+Na$^+$) calc.: 834.3, found: 834.3.

$N^{2'}$-deacetyl-$N^{2'}$-(4-mercapto-1-oxopentyl)maytansine (L-DM3, 4a): L-DM3-SMe (4c, 12 mg, 0.015 mmol) was dissolved in 1.0 mL of a 1:1 mixture of ethyl acetate and methanol. A solution of dithiothreitol (18 mg, 0.117 mmol) in 0.50 mL of 50 mM phosphate buffer, pH 7.5, was then added. The reaction solution was magnetically stirred under an argon atmosphere for 3 hours, then 1 mL of 200 mM phosphate buffer pH 6.0 was added and the mixture was extracted three times with 2 mL portions of ethyl acetate. The organic layers were combined and washed with 1 mL of saturated sodium chloride solution, then dried over 1 g of anhydrous sodium sulfate. Solvent was removed under vacuum and the residue was taken up in a minimum of ethyl acetate and purified on a 50 cm×250 cm, 10 micron Diazem™ CN column using as mobile phase a 70:8:22 mixture of hexane, 2-propanol and ethyl acetate. The flow rate was 22 mL/min. The desired product eluted with a retention time of 10 min. Fractions containing pure product were combined and the solvent was removed under vacuum to give 11 mg of product 4a (97% yield). $^1$H NMR (CDCl$_3$): δ0.80 (3H, s), 1.19-1.23 (1H, m), 1.28-1.36 (9H, m), 1.42-1.46 (1H, m), 1.53-1.63 (2H, m), 1.64 (3H, s), 1.80-1.89 (1H, m), 1.90-2.09 (1H, m), 2.18 (1H, dd, J=3 Hz and 14 Hz), 2.33-2.42 (1H, m), 2.49-2.62 (2H, m), 2.88 (3H, s), 3.04 (1H, d, J=9 Hz), 3.11 (1H, d, J=11 Hz), 3.23 (3H, s), 3.35 (3H, s), 3.49 (1H, d, J=9 Hz), 3.63 (1H, d, J=12 Hz), 3.98 (3H, s), 4.27 (1H, t, J=10 Hz), 4.79 (1H, dd, J=3 Hz and 12 Hz), 5.41 (1H, q, J=7 Hz), 5.66 (1H, dd J=9 Hz and 15

Hz), 6.21 (1H, s), 6.42 (1H, dd, J=11 Hz and 15 Hz), 6.65 (1H, d, J=1.5 Hz), 6.73 (1H, d, J=11 Hz), 6.81 (1H, d, J=1.5 Hz). MS: (M+Na$^+$) calc.: 788.3, found: 788.3.

Example 3

Synthesis of Maytansinoid 4g,h (FIG. 3c)

R-1,3-Di-O-p-toluenesulfonyl-butane (17): A solution of R-(−)-1,3-butanediol (16, 2.00 g, 22.22 mmol) in a mixture of dry pyridine (40 mL) and dry toluene (60 mL), was treated with p-toluenesulfonyl chloride (12.70 g, 66.84 mmol) under argon at 0° C. After stirring at 0° C. for 5 min. followed by stirring at room temperature for 2 h, the mixture was evaporated under vacuum, redissolved in ethyl acetate, and washed with 0.1 M aqueous NaHCO$_3$, followed by saturated NaCl. The organic layer was dried over MgSO$_4$, filtered, and the solvent was evaporated. Purification by chromatography on silica gel, eluting with 1:2 (v/v) ethyl acetate/hexane gave 6.51 g (74%) of the title product 17. R$_f$=0.40 (1:1 EtOAc/hexane); $^1$H NMR (CDCl$_3$) 7.76 (dd, 4H, J=1.0, 8.0 Hz), 7.35 (dt, 4H, J=0.4, 8.0+8.0 Hz), 4.70 (m, 1H), 4.03 (m, 1H), 3.94 (m, 1H), 2.46 (s, 6H), 1.92 (m, 2H), 1.26 (d, 3H, J=6.3 Hz); $^{13}$C NMR 145.17, 133.00, 130.11, 128.12, 127.91, 76.28, 66.21, 36.08, 21.86, 21.06; MS: 420.99 (M+Na)$^+$, 421.93 (M+1+Na)$^+$.

S-4-O-Ethylxanthic-pentanenitrile (18): A solution of R-1,3-di-O-p-toluenesulfonyl-butane (17, 4.80 g, 12.06 mmol) in dry DMSO (50 mL) was treated with NaCN (0.65). After stirring at RT under argon for 18 h, the reaction mixture was diluted with ethyl acetate, washed successively with cold 1.0 M of NaH$_2$PO$_4$ pH 7.5, water and 1.0 M of NaH$_2$PO$_4$ pH 4.0. The organic layer was separated and dried over MgSO$_4$, filtered, and then evaporated to give 2.63 g crude of R-3-O-p-toluenesulfonyl-pentanenitrile. MS 275.80 (M+Na)$^+$, 276.75 (M+1+Na)$^+$. The product was used directly without further purification.

To the solution of crude of R-3-O-p-toluenesulfonyl-pentanenitrile (2.63 g) in ethanol (15 mL) was added potassium O-ethylxanthate (4.55 g) in ethanol (50 mL). After stirring overnight under argon, the mixture was concentrated, diluted with ethyl acetate, and filtered through a short silica column. The eluant was concentrated and purified by chromatography on silica gel, eluting with 1:4 (v/v) EtOAc/hexane, to give 1.54 g (63%, 2 steps) of the title product 18. R$_f$=0.40 (1:4 EtAc/hexane). $^1$H NMR (CDCl$_3$) 4.67 (dd, 2H, J=7.1, 14.2 Hz), 3.86 (ddd, 1H, J=7.0, 14.0, 21.9 Hz), 2.50 (t, 2H J=7.3+7.6 Hz), 2.06 (m, 2H), 1.44 (m, 6H); $^{13}$C NMR 213.04, 119.16, 70.28, 44.57, 32.10, 20.20, 15.21, 13.93; MS: 226.51 (M+Na)$^+$, 242.51 (M+K)$^+$.

S-(+)-4-Methyldithio-pentanoic acid (19): To a solution of S-4-O-Ethylxanthic-pentanenitrile (18, 1.95 g (9.61 mmol) in a mixture of ethanol (10 mL) and water (150 mL) was added 5.0 g of NaOH. The reaction mixture was refluxed overnight under argon. The mixture was cooled to room temperature and diluted with water (150 ml) and extracted with 1:1 EtOAc/hexane (2×100 ml). The aqueous layer was acidified with H$_3$PO$_4$ to pH 2.5~3.0 and extracted with EtOAc (6×75 ml). The organic layers were combined, dried over MgSO$_4$, filtered and evaporated to dryness to give the crude S-4-mercaptopentanoic acid. This crude product was used directly for next step without further purification.

To a solution of crude S-4-mercaptopentanoic acid (1.2 g) in a mixture of ethanol (10 mL) and 0.5 M NaH$_2$PO$_3$, pH 7.0 (75 mL), was added dropwise methyl methanethiolsulfonate (1.47 g, 11.65 mmol) in 5 dry THF (5 mL) over 45 min at 0° C. After stirring under argon at 0° C. for 30 min, followed by stirring at room temperature for 2 h, the mixture was concentrated and extracted with dichloromethane (2×50 ml). The aqueous layer was acidified with H$_3$PO$_4$ to pH 2.5~3.0 and extracted with EtOAc (4×100 ml). The organic layers were combined, dried over MgSO$_4$, filtered and evaporated. The residue was purified by chromatography over silica gel, eluting with (1:100:400 HOAc/EtOAc/hexane) to give 1.43 g (83%) of the title product 19. R$_f$=0.32 (1:100:400 HOAc/EtAc/hexane); $^1$H NMR (CDCl$_3$) 2.91 (ddd, 1H, J=6.8, 13.7, 20.5 Hz), 2.53 (t, 2H, J=7.7+7.4 Hz), 2.42 (s, 3H), 1.94 (m, 2H), 1.36 (d, 3H, J=6.8 Hz); $^{13}$C NMR 179.18, 45.35, 31.58, 30.73, 24.70, 21.05; MS: 202.92 (M+Na)$^+$, 203.91 (M+Na)$^+$; [α]=41.35 (c=2, CH$_3$OH).

N-methyl-N-[4-(S)-methyldithio-1-oxopentyl]-S-alanine (15a): S-(+)-4-(Methyldithio)-pentanoic acid (19) was converted into the N-hydroxysuccinimdyl ester 20, by the method described above for compound 14. Reaction with N-methyl-L-alanine by the procedure described above for compound 15 gave 15a, (62% yield). H$^1$ NMR δ1.36 (3H, d, J=7), 1.42 (3H, d, J=7), 1.93-1.98 (2H, m), 2.40 (3H, s), 2.50-2.53 (2H, m), 2.90-2.95 (1H, m), 2.99 (3H, s), 5.14 (1H, q, J=7), MS: (M+Na) calc.: 288.1, found: 288.1.

N$^{2'}$-deacetyl-N$^{2'}$-(4-(S)-methyldithio-1-oxopentyl)maytansine (DM3-SMe, 4g,h): Maytansinol (11) was coupled with 15a, using DCC and zinc chloride in dichloromethane, as described above for the synthesis of 4c. A mixture of 2 diastereomers bearing the N-methyl-S-alanyl moiety (4g, S,S) and the N-methyl-R-alanyl moiety (4h, R,S) were obtained. The diastereomers were separated by HPLC on a Kromasil cyano column (4.6 mm×250 mm), using an isocratic elution at a flow rate of 1 mL/min, with hexane:ethyl acetate:2-propanol (68:24:8, v/v/v). Under these conditions, the isomer 4g (S.S) eluted at 24.5 min. Mass spectrum: m/z 834.2 (M+Na)$^+$. The peak for the other isomer 4h (R,S) was well separated and eluted at 34.6 min. MS: m/z 834.2 (M+Na)$^+$.

Example 4

Figure 3D:
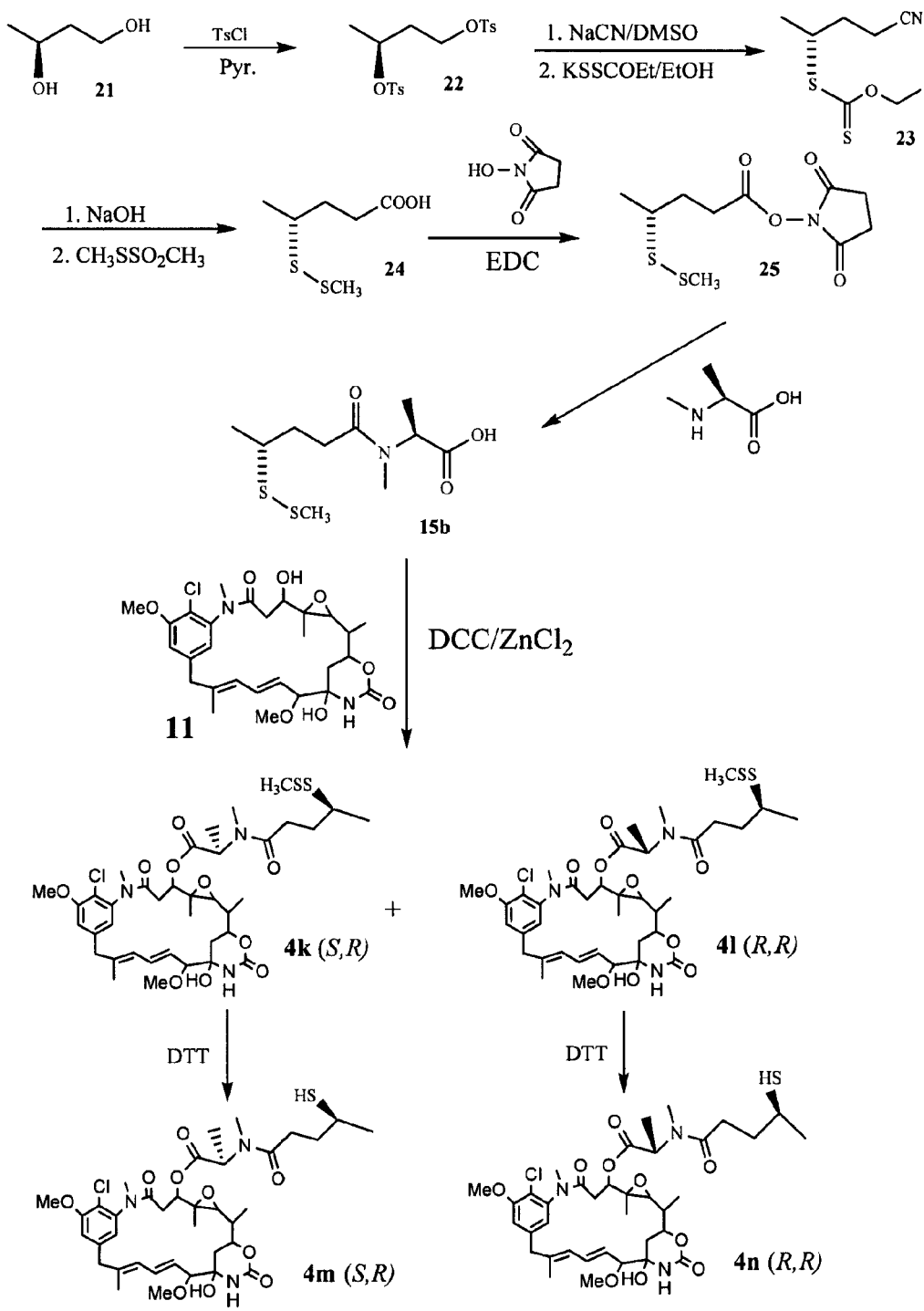

Synthesis of Maytansinoid 4k,l (FIG. 3d)

S-1,3-Di-O-p-toluenesulfonyl-butane 22: A solution of S-(−)-1,3-butanediol (21, 2.00 g (22.22 mmol) in a mixture of dry pyridine (40 mL) and dry toluene (60 mL) was treated with p-toluenesulfonyl chloride (12.70 g, 66.84 mmol) under argon at 0° C. After stirring at 0° C. for 5 min. followed by stirring at room temperature for 2 h, the mixture was evaporated under vacuum. The residue was redissolved in ethyl acetate, washed with 0.1 M aqueous NaHCO$_3$, and saturated NaCl. The organic layer was separated, dried over MgSO$_4$, filtered and evaporated. The residue was purified by chromatography over silica gel, eluting with 1:2 ethyl acetate/hexane to give 6.25 g (71%) of the title product 22 R$_f$=0.40 (1:1 EtOAc/hexane); $^1$H NMR (CDCl$_3$) 7.76 (dd, 4H, J=1.0, 8.0 Hz), 7.35 (dt, 4H, J=0.4, 8.0+8.0 Hz), 4.70 (m, 1H), 4.03 (m, 1H), 3.94 (m, 1H), 2.46 (s, 6H), 1.92 (m, 2H), 1.26 (d, 3H, J=6.3 Hz); $^{13}$C NMR 145.17, 133.00, 130.11, 128.12, 127.91, 76.28, 66.21, 36.08, 21.86, 21.06; MS: 420.99 (M+Na)$^+$.

R-4-O-Ethylxanthic-pentanenitrile (23): A solution of S-1,3-di-O-p-toluenesulfonyl-butane (22, 6.25 g (15.70 mmol) in dry DMSO (50 mL) was treated with NaCN (0.85 g). The reaction mixture was stirred under argon for 18 h at RT. The reaction mixture was then diluted with ethyl acetate, washed sequentially with cold 1.0 M of NaH$_2$PO$_4$ pH 7.5, water and 1.0 M of NaH$_2$PO$_4$ pH 4.0. The organic layer was dried over MgSO$_4$, filtered, evaporated to give 3.62 g crude of S-3-O-p-toluenesulfonyl-pentanenitrile. The product was used directly without further purification.

To a solution of crude S-3-O-p-toluenesulfonyl-pentanenitrile (3.62 g) in ethanol (50 mL), was added potassium O-ethylxanthate (5.72 g) in ethanol (100 mL). After stirring under argon overnight, the mixture was concentrated, diluted with ethyl acetate and filtered through a short column of silica gel. The eluant was concentrated, and the residue was purified by chromatography over silica gel, eluting with 1:4 EtOAc/hexane to give 2.0 g (62%, 2 steps) of the title product 23. $R_f$=0.40 (1:4 EtAc/hexane). $^1$H NMR (CDCl$_3$) 4.67 (dd, 2H, J=7.1, 14.2 Hz), 3.86 (ddd, 1H, J=7.0, 14.0, 21.9 Hz), 2.50 (t, 2H J=7.3+7.6 Hz), 2.06 (m, 2H), 1.44 (m, 6H); $^{13}$C NMR 213.04, 119.16, 70.28, 44.57, 32.10, 20.20, 15.21, 13.93; MS: 226.51 (M+Na)$^+$, 242.51 (M+K)$^+$.

R-(−)-4-Methyldithio-pentanoic acid (24): A solution of R-4-O-Ethylxanthic-pentanenitrile (23, 2.0 g, 9.85 mmol) in a mixture of ethanol (10 mL) and 200 ml of water was treated with NaOH (6.0 g). The reaction mixture was refluxed overnight under argon. The mixture was diluted with water (150 ml) and extracted with 1:1 EtOAc/hexane (2×100 ml). The aqueous layer was acidified with H$_3$PO$_4$ to pH 2.5~3.0 and extracted with EtAc (6×75 ml). The organic layers were combined, dried over MgSO$_4$, filtered and evaporated to dryness to give the crude R-4-mercaptopentanoic acid. This crude product was used directly for next step without further purification.

To a solution of 1.60 g of the crude R-4-mercaptopentanoic acid in a mixture of ethanol (50 mL) and 0.5 M NaH$_2$PO$_4$, pH 7.0 (75 mL) was added dropwise methyl methanethiolsulfonate (1.96 g, 15.53 mmol) in dry THF (7 mL) over 45 min at 0° C. The reaction mixture was stirred under argon at 0° C. for 30 min and then at room temperature for 2 h. The mixture was concentrated and extracted with dichloromethane (2×50 ml). The aqueous layer was acidified with H$_3$PO$_4$ to pH 2.5~3.0 and extracted with EtOAc (4×100 ml). The organic layers were combined, dried over MgSO$_4$, filtered and evaporated. The residue was purified by chromatography over silica gel, eluting with 1:100:400 HOAc/EtOAc/hexane to give 1.65 g (93%) of the title product 24. $R_f$=0.32 (1:100:400 HOAc/EtOAc/hexane); $^1$H NMR (CDCl$_3$) 2.91 (ddd, 1H, J=6.8, 13.7, 20.4 Hz), 2.53 (t, 2H, J=7.7+7.4 Hz), 2.42 (s, 3H), 1.96 (m, 2H), 1.36 (d, 3H, J=6.8 Hz); $^{13}$C NMR 179.46, 45.67, 31.91, 31.07, 25.02, 21.36; MS: 202.9 (M+Na)$^+$, 203.9 (M+Na)$^+$; [α]=−39.16 (c=2, CH$_3$OH).

N-methyl-N-[4-(R)-methyldithio-1-oxopentyl]-S-alanine (15b): R-(+)-4-Methyldithio-pentanoic acid (24) was converted into the N-hydroxysuccinimdyl ester 25, by the method described above for compound 14. Reaction with N-methyl-L-alanine by the procedure described above for compound 15 gave 15b. MS: m/z (M+Na): calc.: 288.1, found: 288.1.

N$^{2'}$-deacetyl-N$^{2'}$-(4-(R)-methyldithio-1-oxopentyl)maytansine (DM3-SMe, 4k,l): Maytansinol (11) was coupled with 15b, using DCC and zinc chloride in dichloromethane, as described above for the synthesis of 4c. A mixture of 2 diastereomers bearing the N-methyl-S-alanyl moiety (4k, S,R) and the N-methyl-R-alanyl moiety (4l, R,R) were obtained. The diastereomers were separated by HPLC on a Kromasil cyano column (4.6 mm×250 mm), using an isocratic elution at a flow rate of 1 mL/min, with hexane:ethyl acetate:2-propanol (68:24:8, v/v/v). Under these conditions, the isomer 4k (S.R) eluted at 23.9 min. Mass spectrum: m/z 834.2 (M+Na)$^+$. The peak for the other isomer 4l (R,R) was well separated and eluted at 33.7 min. MS: m/z 834.2 (M+Na)$^+$.

Example 5a

In Vitro Cytotoxicity of Maytansinoids and Antibody-Maytansinoid Conjugates

The KB (ATCC CCl-17) cell line is of human epithelial origin. The SK-BR-3 (ATCC HTB-30) cell line was established from a human breast adenocarcinoma. The human colon tumor cell lines COLO 205 (ATCC CCL-222) and HT-29 (ATCC HTB 38), the human melanoma cell line A-375 (ATCC CRL 1619), the human Burkitts lymphoma cell line Ramos (ATCC CRL-1596) and the human myeloid leukemia cell line HL-60 (ATCC CCL-240) were all obtained from ATCC, Maryland. Cell lines were grown in Dulbecco's modified Eagles Medium (DMEM, Biowhittaker, Walkersville, Md.) with L-glutamine supplemented with 10% fetal bovine serum (Hyclone, Logan, Utah) and 50 μg/mL gentamycin sulfate (Life Technologies, Rockville, Md.). Cells were maintained at 36-37.5° C. in a humidified atmosphere that contained 6% CO$_2$.

The cytotoxicity study performed used a clonogenic assay. The test cell lines were plated into 6-well culture dishes at a constant number of 1000 cells per well. Cells were incubated with varying concentrations (0 to 3 nM) of the various maytansinoids (free or conjugated to antibodies) for 72 hours. The medium was then aspirated from the plates and replaced with fresh medium. Cultures were allowed to grow, and form colonies, for a total of 7-10 days after plating. The cultures were then fixed and stained with 0.2% crystal violet in 10% formalin/PBS and colonies were counted. Plating efficiency of non-treated cells (medium alone) was determined by dividing the number of colonies counted by the number of cells plated. Surviving fraction of cells exposed to the drugs was determined by dividing the number of colonies in wells that were exposed to the drug by the number of colonies in the control wells.

The results of the in vitro cytotoxicity measurements of the new maytansinoids of the present invention are shown in FIG. 4. The new maytansinoids 4c,e bearing hindered disulfide bonds are highly cytotoxic towards both cell lines tested, SK-BR-3 and A-375, with IC$_{50}$ values ranging from 7×10$^{-12}$ M to 2.5×10$^{-11}$ M. Thus, incorporation of alkyl substituents on the carbon bearing the disulfide moiety has preserved high cytotoxic potency. The sterically hindered thiol-containing maytansinoid 4a of the present invention is 30 to 50-fold more potent than the previously described corresponding unhindered maytansinoid 1. Thus, incorporation of alkyl substituents on the carbon atom bearing the thiol moiety greatly enhances potency.

The results of in vitro testing of antibody conjugates of the maytansinoids of the present invention are shown in FIGS. 4c and 4d. The linkage of the two new maytansinoids, 4a or 4b, to the huC242 antibody directed against human colon tumors, resulted in antigen-specific killing of target cells. Thus, the conjugates are highly potent towards antigen-positive COLO 205 cells, with IC$_{50}$ values ranging from 1.1 to 1.3×10$^{-11}$M. In contrast, the conjugates are 100 to 200-fold less cytotoxic towards antigen-negative A-375 cells, demonstrating that the new maytansinoids of the present invention produce conjugates that possess sterically hindered disulfide bonds, and display high target specific cytotoxicity.

Example 5b

Preparation of Cytotoxic Conjugates of huC242 Antibody Using Maytansinoids 4a or 4b (Method A, FIG. 5 a,b)

A solution of huC242 antibody (8 mg/mL) in aqueous buffer (50 mM potassium phosphate, 50 mM sodium chloride, 2 mM ethylenediaminetetraacetic acid disodium salt), pH 6.5, was incubated for 2 h with a 7 to 10-fold molar excess of SPDP [succinimidyl 3-(2-pyridyldithio)propionate, 3a), or with N-succinimidyl-4-(2-pyridyldithio)butanoate (SPDB, 3b). The reaction mixture was purified by passage through a Sephadex G25 gel filtration column. The concentration of the antibody was determined spectrophotometrically using the known extinction coefficients for the antibody $\epsilon_{280nm}$=217,560 M−1cm−1.

The modified antibody was diluted to 2.5 mg/mL in aqueous buffer (50 mM potassium phosphate, 50 mM sodium chloride, 2 mM ethylenediaminetetraacetic acid disodium salt), pH 6.5, and then treated with a 1.5 to 2.5 molar excess of either DM3 or DM4 in dimethylacetamide (final concentration of DMA was 3% v/v). The reaction mixture was incubated for 18 h at room temperature. The reaction mixture was purified by passage through a Sephadex G25 gel filtration column. The concentration of the conjugate was determined spectrophotometrically using the known extinction coefficients for the antibody $\epsilon_{280nm}$=217,560 M$^{-1}$cm$^{-}$ and $\epsilon_{252nm}$=80,062 M$^{-1}$cm$^{-1}$; for DM3 or DM4, $\epsilon_{280nm}$=5,700 M$^{-1}$cm$^{-1}$ and $\epsilon_{252nM}$=26,790 M$^{-1}$cm$^{-1}$). The resulting conjugate was monomeric and contained, on the average, 3.2-3.5 DM3 or DM4 molecules linked per antibody molecule.

Example 5c

Preparation of Cytotoxic Conjugates of huC242 Antibody Using Maytansinoids 4a or 4b (Method B, FIG. 5c)

A solution of huC242 antibody (8 mg/mL) in aqueous buffer (50 mM potassium phosphate, 50 mM sodium chloride, 2 mM ethylenediaminetetraacetic acid disodium salt), pH 6.5, was incubated for 2 h with a 7 to 10-fold molar excess of SMCC [succinimidyl 4-(N-maleimidomethyl)-cyclohexane-1-carboxylate, 26). The reaction mixture was purified by passage through a Sephadex G25 gel filtration column. The concentration of the antibody was determined spectrophotometrically using the known extinction coefficients for the antibody $\epsilon_{280nm}$=217,560 M$^{-1}$cm$^{-1}$.

The modified antibody was diluted to 2.5 mg/mL in aqueous buffer (50 mM potassium phosphate, 50 mM sodium chloride, 2 mM ethylenediaminetetraacetic acid disodium salt), pH 6.5, and then treated with a 1.5 to 2.5 molar excess of either DM3 or DM4 in dimethylacetamide (final concentration of DMA was 3% v/v). The reaction mixture was incubated for 18 h at room temperature. The reaction mixture was purified by passage through a Sephadex G25 gel filtration column. The concentration of the conjugate was determined spectrophotometrically using the known extinction coefficients (for the antibody $\epsilon_{280nm}$=217,560 M$^{-1}$cm$^{-1}$ and $\epsilon_{252nm}$=80,062 M$^{-1}$cm$^{-1}$; for DM3 or DM4, $\epsilon_{280nm}$=5,700 M$^{-1}$cm$^{-1}$ and $\epsilon_{252nM}$=26,790 M$^{-1}$cm$^{-1}$). The resulting conjugate was monomeric and contained, on the average, 3.2-3.5 DM3 or DM4 molecules linked per antibody molecule.

Example 5d

Preparation of Cytotoxic Conjugates of huC242 Antibody Using Maytansinoids 4a or 4b (Method C, FIG. 5d)

A solution of huC242 antibody (8 mg/mL) in aqueous buffer (50 mM potassium phosphate, 50 mM sodium chloride, 2 mM ethylenediaminetetraacetic acid disodium salt), pH 6.5, was incubated for 2 h with a 7 to 10-fold molar excess of SIAB [N-succinimidyl (4-iodoacetyl)aminobenzoate, 27). The reaction mixture was purified by passage through a Sephadex G25 gel filtration column. The concentration of the antibody was determined spectrophotometrically using the known extinction coefficients for the antibody $\epsilon_{280nm}$=217,560 M$^{-1}$cm$^{-1}$.

Example 6

In Vivo Efficacy of huC242-Maytansinoid Conjugates Against HT-29 Xenografts

Five-week-old female SCID mice (20 animals) were inoculated subcutaneously in the right flank with HT-29 human colon carcinoma cells (1.5×10$^6$ cells/mouse) in 0.1 mL of serum-free medium. The tumors were grown for 11 days to an average size of 100 mm$^3$. The animals were then randomly divided into four groups (5 animals per group). The first group received huC242-DM1 conjugate (DM1 dose of 75 μg/kg, qd×5) administered intravenously. The second group received huC242-DM3 conjugate (DM3 dose of 75 μg/kg, qd×5) administered intravenously. The third group received huC242-DM4 conjugate (DM4 dose of 75 μg/kg, qd×5), while a fourth group of animals served as controls and received PBS using the same treatment schedule as in groups 1-3.

The sizes of the tumors were measured twice weekly and the tumor volumes were calculated with the formula: tumor volume=½(length×width×height). The weight of the animals was also measured twice per week. The results are shown in FIG. 7. The tumors in the control group of mice grew to a size of nearly 1000 mm$^3$ in 35 days. Treatment with huC242-DM1 resulted in a tumor growth delay of 18 days, while conjugates made with the maytansinoids 4a and 4b of the present invention were significantly more efficacious and prolonged the tumor growth delay to 28 days and 36 days, respectively.

Example 7

In Vivo Efficacy of huC242-Maytansinoid Conjugates Against COLO 205 Xenografts

Five-week-old female SCID mice (20 animals) were inoculated subcutaneously in the right flank with COLO 205 human colon carcinoma cells (1.5×10$^6$ cells/mouse) in 0.1 mL of serum-free medium. The tumors were grown for 11 days to an average size of 100 mm$^3$. The animals were then randomly divided into four groups (5 animals per group). The first group received huC242-DM1 conjugate (DM1 dose of 75 μg/kg, qd×5) administered intravenously. The second group received huC242-DM3 conjugate (DM3 dose of 75 μg/kg, qd×5) administered intravenously. The third group received huC242-DM4 conjugate (DM4 dose of 75 μg/kg, qd×5), while a fourth group of animals served as controls and received PBS using the same treatment schedule as in groups 1-3.

The sizes of the tumors were measured twice weekly and the tumor volumes were calculated with the formula: tumor volume=½(length×width×height). The weight of the animals was also measured twice per week. The results are shown in FIG. 8. The tumors in the control group of mice grew to a size of nearly 900 mm³ in 24 days. Treatment with huC242-DM1 resulted in a tumor growth delay of 20 days, while the conjugate made with the maytansinoid 4a of the present invention was considerably more efficacious and caused complete tumor regressions lasting 45 days. Treatment with the conjugate made with the maytansinoid 4b of the present invention was even more efficacious, resulting in cures of all the treated animals.

Example 8

In Vivo Efficacy of MY9-6-Maytansinoid Conjugates Against HL-60 Xenografts

Five-week-old female SCID mice (20 animals) were inoculated subcutaneously in the right flank with HL-60 human myeloid leukemia cells (1.5×10⁶ cells/mouse) in 0.1 mL of serum-free medium. The tumors were grown for 12 days to an average size of 100 mm³. The animals were then randomly divided into four groups (5 animals per group). The first group received MY9-6-DM1 conjugate (DM1 dose of 200 µg/kg, qd×5) administered intravenously. The second group received MY9-6-DM3 conjugate (DM3 dose of 200 µg/kg, qd×5) administered intravenously. The third group received MY9-6-DM4 conjugate (DM4 dose of 200 µg/kg, qd×5) administered intravenously, while a fourth group of animals served as controls and received PBS using the same treatment schedule as in groups 1-3.

The sizes of the tumors were measured twice weekly and the tumor volumes were calculated with the formula: tumor volume=½(length×width×height). The weight of the animals was also measured twice per week. The results are shown in FIG. 9. The tumors in the control group of mice grew rapidly to a size of nearly 1600 mm³ in 21 days. Treatment with MY9-6-DM1 resulted in a tumor growth delay of about 5 days, while conjugates made with the maytansinoids 4a and 4b of the present invention were significantly more efficacious prolonging the tumor growth delay to greater than 20 days.

Example 9

Preparation of a Cytotoxic Conjugate of huMy9-6 Antibody Using Maytansinoid DM4 (4b)

A solution of huMy9-6 antibody at a concentration of 8 mg/mL was incubated for 2 h with a 6.5 molar excess of SSNPB [sulfosuccinimidyl 4-(5'-nitro-2'-pyridyldithio)butyrate] in 50 mM potassium phosphate buffer, pH 6.5, containing 2 mM ethylenediaminetetraacetic acid (buffer A) with 5% ethanol. The modified antibody was purified by passage through a Sephadex G25 gel filtration column equilibrated in buffer A and the concentration of the purified antibody was determined spectrophotometrically using the extinction coefficient for the antibody at 280 nm. The modified antibody was diluted to 4.9 mg/mL with buffer A and incubated for 18 h at room temperature with 1.7-fold molar excess of DM4, which was added to the reaction mixture as a stock solution in dimethylacetamide (final concentration of dimethylacetamide was 3% v/v). The antibody-drug conjugate was purified by passage through a Sephadex G25 column equilibrated in PBS, pH 6.5. The concentration of conjugate was determined spectrophotometrically using the know extinction coefficients for antibody and DM4 (for the antibody, $\epsilon_{280nm}$=206,460 M⁻¹cm⁻¹, $\epsilon_{252nm}$=72,261 M⁻¹cm⁻¹; for DM4, $\epsilon_{280nm}$=5,700 M⁻¹cm⁻¹, $\epsilon_{252nM}$=26,790 M⁻¹cm⁻¹). The resulting antibody-drug conjugate contained an average of 3.6 DM4 molecules per antibody molecule. Biochemical analysis demonstrated that the antibody remained greater than 94% monomeric following conjugation and had a binding affinity comparable to the unmodified antibody as determined by flow cytometry. The amount of drug associated with the antibody that was not linked covalently (free drug) was determined by HPLC analysis and found to be less than 1% of the total linked drug.

Example 10

In Vitro Selectivity and Efficacy of huMy9-6-DM4 Conjugate

The cytotoxicity of huMy9-6-DM4 toward CD33 expressing cells (HL-60) and CD33-negative Namalwa cells was tested using a clonogenic assay, where cell killing activity is determined by quantifying the number of colonies that can grow following treatment. huMy9-6-DM4 exhibits potent cell killing activity toward CD33-positive HL-60 human tumor cells in vitro (FIG. 10). No significant toxicity toward CD33-negative human Namalwa cells was observed, indicating that the CD33-dependent cytotoxicity was due to specific targeting by the anti-CD33 antibody, huMy9-6 of the conjugate.

Example 11

In Vivo Efficacy of huMy9-6-DM4 Conjugates Against HL60 Human Tumor Xenografts in SCID Mice The efficacy of huMy9-6-DM4 in vivo was determined in SCID mice bearing human HL-60 tumor xenografts. HL-60 cells were injected subcutaneously and tumors were allowed to grow to an average size of 100 mm³. HuMy9-6-DM4 conjugate was delivered i.v. once a day for 5 days at the dose indicated in FIG. 11. Dosage is expressed as µg DM4 in the conjugate, which corresponds to an antibody dose of approximately 67 µg antibody per µg of DM4. Tumor volume was measured as an indication of treatment efficacy and mouse body weight was monitored to indicate toxicity due to treatment. huMy9-6-DM4 induces prolonged tumor growth delay of human HL-60 cell xenografts at doses that cause little toxicity (FIG. 11). The efficacy of huMy9-6-DM4 was also compared with that of huMy9-6-DM1. Unexpectedly, it was found that huMy9-6-DM4 was more effective than huMy9-6-DM1. HuMy9-6-DM4 maintained the animals in complete remission (CR) for nearly sixty days, whereas animals treated with huMy9-6-DM1 relapsed after about 20 days in CR.

Example 12

Preparation of a Cytotoxic Conjugate of huB4 Antibody Using Maytansinoid DM4 (4b)

A solution of huB4 antibody at a concentration of 20 mg/mL was incubated for 1.5 h with an 8-fold molar excess of SSNPB [sulfosuccinimidyl 4-(5'-nitro-2'-pyridyldithio)butyrate] in 50 mM potassium phosphate buffer, pH 6.5 containing 2 mM ethylenediaminetetraacetic acid (buffer A) with 5% dimethylacetamide. The modified antibody was purified by passage through a Sephadex G25 gel filtration column equilibrated in buffer A and the concentration of the purified antibody was determined spectrophotometrically using the extinction coefficient for the antibody at 280 nm (199,560 $M^{-1}cm^{-1}$). The modified antibody was diluted to 8 mg/mL with buffer A and incubated for 3 h at ambient temperature with a 1.7-fold molar excess of DM4, which was added to the reaction mixture as a stock solution in dimethylacetamide (final concentration of dimethylacetamide was 3% v/v). The antibody-drug conjugate was purified by passage through a Sephadex G25 column and a Sephadex S300 column, both equilibrated in PBS buffer, pH 6.5. The concentration of conjugate was determined spectrophotometrically using the know extinction coefficients for antibody ($\epsilon_{280nm}$: 199,560 $M^{-1}cm^{-1}$; $\epsilon_{252nm}$: 67,850 $M^{-1}cm^{-1}$) and DM4 ($\epsilon_{280nm}$=5,700 $M^{-1}cm^{-1}$, $\epsilon_{252nM}$=26,790 $M^{-1}cm^{-1}$). The resulting antibody-drug conjugate contained an average of 4.0 DM4 molecules per antibody molecule. Biochemical analysis demonstrated that the antibody remained greater than 98% monomeric following conjugation and had a binding affinity comparable to the unmodified antibody as determined by flow cytometry. The amount of drug associated with the antibody that was not linked covalently (free drug) was determined by HPLC analysis and was approximately 2% of the total linked drug.

Example 13

In Vitro Selectivity and Efficacy of huB4-DM4 Conjugate

The cytotoxicity of huB4-DM4 toward CD19-expressing cells (Ramos) compared to a CD19-negative cell line (Colo 205) was tested using an MTT-based assay, where cell killing activity is determined by quantifying the number of viable cells that remain following treatment with conjugate. Viable cell number is determined by spectrophotometric quantitation following incubation of the cells with the vital dye MTT. HuB4-DM4 exhibits potent cell killing activity toward CD19-positive Ramos human tumor cells in vitro (FIG. 12). No significant toxicity toward CD19-negative cells was observed, indicating that the CD19-dependent cytotoxicity was due to specific targeting by the anti-CD19 antibody, huB4.

Example 14

In Vivo Efficacy of huB4-DM4 Conjugate Against Ramos Human Tumor Xenografts in SCID Mice The efficacy of huB-DM4 in vivo was determined using SCID mice bearing established human Ramos tumor xenografts. Ramos cells were injected subcutaneously and tumors were allowed to grow to an average size of 100 mm³. HuB4-DM4 conjugate was delivered i.v. as a single injection at the doses indicated in FIG. 13*a*. Dosage is expressed as μg DM4 in the conjugate, which corresponds to an antibody dose of approximately 44 μg antibody per μg of DM4. Tumor volume was measured as an indication of treatment efficacy and mouse body weight was monitored to indicate toxicity due to treatment. At doses above 50 μg/kg, HuB4-DM4 causes complete regression of the tumors in all animals. Animals remain without measurable disease for about 35 days in the 100 mg/kg treatment group, and for more than 55 days in the two highest dose groups. These treatments caused very little if any toxicity (FIG. 13*b*) as judged by changes in the body weight of the treated animals.

What is claimed is:

1. A compound of formula III:

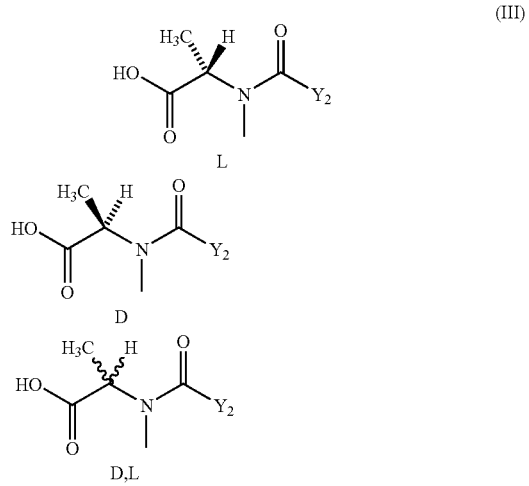

wherein:

$Y_2$ represents $(CR_7R_8)_l(CR_5R_6)_m(CR_3R_4)_nCR_1R_2SZ_2$, wherein:

$R_1$ and $R_2$ are each independently linear alkyl or alkenyl having from 1 to 10 carbon atoms, branched or cyclic alkyl or alkenyl having from 3 to 10 carbon atoms, phenyl, phenyl substituted with at least one alkyl containing from 1-4 carbon atoms, or an alkoxy, halogen or nitro, or heterocyclic aromatic or heterocyclic radical, and in addition $R_2$ can be H;

$R_3$, $R_4$, $R_5$, $R_6$, $R_7$ and $R_8$ are each independently H, linear alkyl or alkenyl having from 1 to 10 carbon atoms, branched or cyclic alkyl or alkenyl having from 3 to 10 carbon atoms, phenyl, phenyl substituted with at least one alkyl containing from 1-4 carbon atoms, or an alkoxy, halogen or nitro, or heterocyclic aromatic or heterocyclic radical;

l, m and n are each independently an integer of from 1 to 5, and in addition n can be 0; and $Z_2$ is SR or —COR, wherein R is linear alkyl, branched alkyl or cyclic alkyl having from 1 to 10 carbon atoms, or simple aryl or aryl substituted with at least one alkyl containing from 1-4 carbon atoms, or heterocyclic aromatic or heterocyclic radical, wherein said heterocyclic aromatic radical or said heterocyclic radical is a 3-10 membered ring containing one or two heteroatoms selected from N, O or S.

2. N-methyl-N-(4-methyl-4-methyldithio-1-oxopentyl)-alanine, N-methyl-N-[4-(R)-methyldithio-1-oxopentyl]-alanine, N-methyl-N-[4-(S)-methyldithio-1-oxopentyl]-alanine or racemic N-methyl-N-(4-methyldithio-1-oxopentyl)-alanine containing N-methyl-L-alanine, N-methyl-D-alanine, or racemic N-methylalanine.

3. A method of making N-methyl-N-(4-methyl-4-methyldithio-1-oxopentyl)-alanine containing N-methyl-L-alanine, N-methyl-D-alanine, or racemic N-methylalanine comprising:

(1) reacting isobutylene sulfide (5) with the anion of acetonitrile to give 4-mercapto-4-methyl-pentanenitrile (6);

(2) hydrolyzing (6) to give 4-mercapto-4-methylpentanoic acid (7);

US 7,473,796 B2

57

(3) converting (7) into 4-methyl-4-(methyldithio)pentanoic acid (8) by reaction with methylmethanethiolsulfonate;

(4) converting (8) into N-hydroxysuccinimidyl 4-methyl-4-(methyldithio)pentanoate (9); and (5) reacting (9) with N-methyl-L-alanine, N-methyl-D-alanine, or racemic N-methylalanine to give said N-methyl-N-(4-methyl-4-methyldithio-1-oxopentyl)-alanine containing N-methyl-L-alanine, N-methyl-D-alanine, or racemic N-methylalanine.

4. A mixture of N-methyl-N-[4-(S)-methyldithio-1-oxopentyl]-S-alanine and N-methyl-N-[4-(R)-methyldithio-1-oxopentyl]-S-alanine.

5. A method of making a mixture of N-methyl-N-[4-(S)-methyldithio-1-oxopentyl]-S-alanine and N-methyl-N-[4-(R)-methyldithio-1-oxopentyl]-S-alanine, comprising:

(1) reacting 4-mercaptopentanoic acid (12) with methylmethanethiolsulfonate to give 4-methyldithio-pentanoic acid (13);

(2) converting (13) into N-hydroxysuccinimidyl 4-methyldithio-pentanoate (14); and (3) reacting (14) with N-methyl-L-alanine to give said mixture of N-methyl-N-[4-(S)-methyldithio-1-oxopentyl]-S-alanine and N-methyl-N-[4-(R)-methyldithio-1-oxopentyl]-S-alanine.

6. A mixture of N-methyl-N-[4-(S)-methyldithio-1-oxopentyl]-R-alanine and N-methyl-N-[4-(R)-methyldithio-1-oxopentyl]-R-alanine.

7. A method of making a mixture of N-methyl-N-[4-(R)-methyldithio-1-oxopentyl]-R-alanine and N-methyl-N-[4-(S)-methyldithio-1-oxopentyl]-R-alanine comprising:

(1) reacting 4-mercaptopentanoic acid (12) with methyl methanethiolsulfonate to give 4-methyldithio-pentanoic acid (13);

(2) converting (13) into N-hydroxysuccinimidyl 4-methyldithio-pentanoate (14); and (3) reacting (14) with N-methyl-D-alanine to give said mixture of N-methyl-N-[4-(R)-methyldithio-1-oxopentyl]-R-alanine and N-methyl-N-[4-(S)-methyldithio-1-oxopentyl]-R-alanine.

8. Racemic N-methylalanine acylated with a carboxylic group bearing a protected thiol functionality, in which the

58 carbon center bearing the sulfur atom is either racemic or of the R or S chirality to give N-methyl-N-(4-methyldithio-1-oxopentyl)-L-alanine.

9. A method of making racemic N-methylalanine acylated with a carboxylic group bearing a protected thiol functionality, in which the carbon center bearing the sulfur atom is either racemic or of the R or S chirality to give N-methyl-N-(4-methyldithio-1-oxopentyl)-alanine, comprising:

(1) reacting 4-mercaptopentanoic acid (12) with methyl methanethiolsulfonate to give 4-methyldithio-pentanoic acid (13);

(2) converting (13) into N-hydroxysuccinimidyl 4-methyldithio-pentanoate (14);

(3) reacting (14) with racemic N-methylalanine to give said racemic N-methylalanine acylated with a carboxylic group bearing a protected thiol functionality, in which the carbon center bearing the sulfur atom is either racemic or of the R or S chirality to give N-methyl-N-(4-methyldithio-1-oxopentyl)-alanine containing N-methyl-L-alanine and N-methyl-D-alanine.

10. N-methyl-N-[4-(S)-methyldithio-1-oxopentyl]-S-alanine.

11. A method of making N-methyl-N-[4-(S)-methyldithio-1-oxopentyl]-S-alanine (15a) comprising:

(1) converting (R)-1,3-butanediol into (S)-4-(methydithio) pentanoic acid (19);

(2) converting (19) into its N-hydroxysuccinimidyl (S)-4-(methydithio)pentanoate (20); and (3) reacting compound (20) with N-methyl-L-alanine to give said N-methyl-N-[4-(S)-methyldithio-1-oxopentyl]-S-alanine.

12. N-methyl-N-[4-(R)-methyldithio-1-oxopentyl]-S-alanine.

13. A method of making N-methyl-N-[4-(R)-methyldithio-1-oxopentyl]-S-alanine (15b) comprising:

(1) converting (S)-1,3-butanediol into (R)-4-(methydithio) pentanoic acid (24);

(2) converting (24) into its hydroxysuccinimidyl (R)-4-(methydithio)pentanoate (25); and (3) reacting (25) with N-methyl-L-alanine to give said N-methyl-N-[4-(R)-methyldithio-1-oxopentyl]-S-alanine.

* * * * *